United States Patent
Mukhopadhyay et al.

(10) Patent No.: US 12,400,739 B2
(45) Date of Patent: *Aug. 26, 2025

(54) OLIGONUCLEOTIDE-BASED MACHINE LEARNING

(71) Applicant: Creyon Bio, Inc., Carlsbad, CA (US)

(72) Inventors: Swagatam Mukhopadhyay, Oceanside, CA (US); Christopher E. Hart, Carlsbad, CA (US)

(73) Assignee: Creyon Bio, Inc., Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/664,821

(22) Filed: May 15, 2024

(65) Prior Publication Data

US 2024/0404636 A1 Dec. 5, 2024

Related U.S. Application Data

(63) Continuation of application No. 17/220,725, filed on Apr. 1, 2021, now Pat. No. 12,057,197.

(60) Provisional application No. 63/005,015, filed on Apr. 3, 2020.

(51) Int. Cl.
*G16B 35/20* (2019.01)
*G16B 40/00* (2019.01)

(52) U.S. Cl.
CPC .............. *G16B 35/20* (2019.02); *G16B 40/00* (2019.02)

(58) Field of Classification Search
CPC ......... G16B 35/20; G16B 40/00; G16B 40/20
See application file for complete search history.

(56) References Cited

U.S. PATENT DOCUMENTS

| | | |
|---|---|---|
| 8,697,359 B1 | 4/2014 | Zhang |
| 8,771,945 B1 | 7/2014 | Zhang |
| 2005/0075492 A1 | 4/2005 | Chen et al. |
| 2005/0142581 A1 | 6/2005 | Griffey et al. |
| 2005/0266552 A1 | 12/2005 | Doench et al. |
| 2005/0272923 A1 | 12/2005 | Zhang et al. |
| 2009/0082975 A1 | 3/2009 | Balac Sipes et al. |
| 2010/0100331 A1 | 4/2010 | Gustafsson et al. |
| 2014/0068797 A1 | 3/2014 | Doudna et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2020/0020420 A1 | 1/2020 | Cai et al. |

FOREIGN PATENT DOCUMENTS

| | | |
|---|---|---|
| WO | WO 2013/141680 A1 | 9/2013 |
| WO | WO 2013/142578 A1 | 9/2013 |
| WO | WO 2013/176772 A1 | 11/2013 |
| WO | WO 2014/065596 A1 | 5/2014 |
| WO | WO 2014/089290 A1 | 6/2014 |
| WO | WO 2014/093595 A1 | 6/2014 |
| WO | WO 2014/093622 A2 | 6/2014 |
| WO | WO 2014/093635 A1 | 6/2014 |
| WO | WO 2014/093655 A2 | 6/2014 |
| WO | WO 2014/093661 A2 | 6/2014 |
| WO | WO 2014/093694 A1 | 6/2014 |
| WO | WO 2014/093701 A1 | 6/2014 |
| WO | WO 2014/093712 A1 | 6/2014 |
| WO | WO 2014/093718 A1 | 6/2014 |
| WO | WO 2014/099744 A1 | 6/2014 |
| WO | WO 2014/099750 A2 | 6/2014 |
| WO | WO 2014/104878 A1 | 7/2014 |
| WO | WO 2019/236548 A1 | 12/2019 |

OTHER PUBLICATIONS

Shieh, K.R., 2016. Computational studies of de novo motif discovery in aptamer selections (Doctoral dissertation, Yeshiva University). (Year: 2016).*

Abdelsayed, M. M. et al., "Multiplex Aptamer Discovery through Apta-Seq and Its Application to ATP Aptamers Derived from Human-Genomic Selex," ACS Chemical Biology, 2017, pp. 2149-2156, vol. 12, No. 8.

Abelson, J. N. et al., "Computer Methods for Macromolecular Sequence Analysis," Methods in Enzymology, 1996, seven pages, vol. 266, 1st Edition (with title page, abstract and table of contents).

Altschul, S. F. et al., "Basic Local Alignment Search Tool," Journal of Molecular Biology, 1990, pp. 403-410, vol. 215.

(Continued)

*Primary Examiner* — Karlheinz R. Skowronek
*Assistant Examiner* — Nidhi Dharithreesan
(74) *Attorney, Agent, or Firm* — Fenwick & West LLP

(57) ABSTRACT

A machine-learned model can be trained on and applied to oligonucleotide data. The machine-learned model can be, for example, a neural network, a random forest classifier, or a regression model, and can be trained in one or more stages. The machine-learned model can be applied in design settings, for instance by being configured to predict biophysical effects corresponding to oligonucleotides, by processing real-world experimental or laboratory data, and by retraining the machine-learned model in response to the processed data.

29 Claims, 18 Drawing Sheets
Specification includes a Sequence Listing.

(56) References Cited

OTHER PUBLICATIONS

Amberger, J. S. et al, "OMIM.org: leveraging knowledge across phenotype-gene relationships." Nucleic Acids Research, 2019, pp. D1038-D1043, vol. 47.

Ämmälä, C. et al., "Targeted delivery of antisense oligonucleotides to pancreatic β-cells," Science Advances, 2018, 11 pages, vol. 4, No. 10, eaat3386.

Bick, D. et al., "Case for genome sequencing in infants and children with rare, undiagnosed or genetic diseases," Journal of Medical Genetics, 2019, pp. 783-791, vol. 56, No. 12.

Catuogno, S. et al., "Nucleic acids delivering nucleic acids," Advanced Drug Delivery Reviews, 2018, pp. 79-93, vol. 134.

Cheng, C. Y. et al., "RNA structure interference through chemical mapping after accidental or intentional mutations," PNAS, Sep. 12, 2017, pp. 9876-9881, vol. 114, No. 37.

Clark, M. M., et al., "Diagnosis of genetic diseases in seriously ill children by rapid whole-genome sequencing and automated phenotyping and interpretation," Science Translational Medicine, 2019, 13 pages, vol. 11, No. 489, eaat6177.

Cole, K. H. et al., "Chapter Eighteen—High-throughput methods in aptamer discovery and analysis," Methods in Enzymology, Elsevier Inc., 2019, pp. 329-346, vol. 621.

Crooke, S. T. et al., "Integrated Assessment of the Clinical Performance of GalNAc$_3$-Conjugated 2'-O-Methoxyethyl Chimeric Antisense Oligonucleotides: I. Human Volunteer Experience," Nucleic Acid Therapeutics, 2019, pp. 16-32, vol. 29, No. 1.

Das, R. et al., "Automated de novo prediction of native-like RNA tertiary structures," Proceedings of the National Academy of Sciences of the United States of America (PNAS), Sep. 11, 2007, pp. 14664-14669, vol. 104, No. 37.

Flynn, R. A. et al., "Transcriptome-wide interrogation of RNA secondary structure in living cells with icSHAPE," Nature Protocols, 2016, pp. 273-290, vol. 11, No. 2.

Hastie, T. et al. "Statistical Learning with Sparsity: The Lasso and Generalizations." Monographs on Statistics and Applied Probability, CRC Press, May 7, 2015, pp. 1-363.

Hastie, T. et al. "The Elements of Statistical Learning: Data Mining, Inference, and Prediction." Springer Series on Statistics, Second Edition, Aug. 26, 2009, pp. 1-765.

Helman, G. et al., "Genome sequencing in persistently unsolved white matter disorders," Annals of Clinical and Translational Neurology, 2020, pp. 144-152, vol. 7, No. 1.

Huang, L. et al., "LinearFold: linear-time approximate RNA folding by 5'-to-3' dynamic programming and beam search," Bioinformatics, 2019, pp. i295-i304, vol. 35, No. 14.

Hung, G. et al., "Characterization of Target mRNA Reduction through in Situ RNA Hybridization in Multiple Organ Systems Following Systemic Antisense Treatment in Animals," Nucleic Acid Therapeutics, 2013, pp. 369-378, vol. 23, No. 6.

Janas, M. M. et al., "Safety evaluation of 2'-deoxy-2'-fluoro nucleotides in GalNAc-siRNA conjugates," Nucleic Acids Research, 2019, pp. 3306-3320, vol. 47, No. 7.

Kesselheim, A. S. et al., "The High Cost of Prescription Drugs in the United States: Origins and Prospects for Reform," JAMA: The Journal of the American Medical Association, 2016, pp. 858-871, vol. 316, No. 8.

Khvorova, A. et al., "The chemical evolution of oligonucleotide therapies of clinical utility," Nature Biotechnology, Mar. 2017, pp. 238-248, vol. 35, No. 3.

Kim, J. et al., "Patient-Customized Oligonucleotide Therapy for a Rare Genetic Disease," The New England Journal of Medicine, 2019, pp. 1644-1652, vol. 381, No. 17.

Lagos-Quintana, M. et al., "Identification of Novel Genes Coding for Small Expressed RNAs," Science, Oct. 26, 2001, pp. 853-857, vol. 294.

Lagos-Quintana, M. et al., "Identification of Tissue-Specific MicroRNAs from Mouse," Current Biology, 2002, pp. 735-739, vol. 12.

Lagos-Quintana, M. et al., "New microRNAs from mouse and human," RNA, 2003, pp. 175-179, vol. 9.

Lau, N. C. et al., "An Abundant Class of Tiny RNAs with Probable Regulatory Roles in Caenorhabditis elegans," Science, Oct. 26, 2001, pp. 858-862, vol. 294.

Lee, B. et al., "Comparison of SHAPE reagents for mapping RNA structures inside living cells," RNA, 2017, pp. 169-174, vol. 23, No. 2.

Lee, R.C. et al., "An Extensive Class of Small RNAs in Caenorhabditis elegans," Science, Oct. 26, 2001, pp. 862, vol. 294, No. 5543.

Lim, L. P. et al., "The microRNAs of Caenorhabditis elegans," Genes & Development, 2003, pp. 991-1008, vol. 17.

Lim, L. P. et al., "Vertebrate MicroRNA Genes," Science, 2003, pp. 1540, vol. 299.

Liu, H. et al. "Challenges of SELEX and Demerits of Aptamer-Based Methods: Affinity Acquisition and Method Design." Aptamers for Analytical Applications: Affinity Acquisition and Method Design, Chapter 12, Editor: Yiyang Dong, Oct. 1, 2018, pp. 345-364.

Loughrey, D. et al., "SHAPE—Seq 2.0: systematic optimization and extension of high-throughput chemical probing of RNA secondary structure with next generation sequencing," Nucleic Acids Research, 2014, 10 pages, vol. 42, No. 21 e165.

Martinovich, K. M. et al., "The potential of antisense oligonucleotide therapies for inherited childhood lung diseases," Molecular and Cellular Pediatrics, 2018, 10 pages, vol. 5, No. 3.

Mathews, D. H., "Revolutions in RNA Secondary Structure Prediction," Journal of Molecular Biology, 2006, pp. 526-532, vol. 359, No. 3.

Mccaskill, J. S., "The Equilibrium Partition Function and Base Pair Binding Probabilities for RNA Secondary Structure," Biopolymers, 1990, pp. 1105-1119, vol. 29, No. 6-7.

Mustoe, A. M. et al. "RNA base-pairing complexity in living cells visualized by correlated chemical probing," PNAS, Dec. 3, 2019, pp. 24574-24582, vol. 116, No. 49.

National Center for Biotechnology Information, "Basic Local Alignment Search Tool," U.S. National Library of Medicine, undated, three pages, [Online] [Retrieved on Jun. 2, 2021], Retrieved from the Internet <URL:https://blast.ncbi.nlm.nih.gov/Blast.cgi>.

Needleman, S. B. et al., "A General Method Applicable to the Search for Similarities in the Amino Acid Sequence of Two Proteins," Journal of Molecular Biology, 1970, pp. 443-453, vol. 48.

Nikam, R. R. et al., "Journey of siRNA: Clinical Developments and Targeted Delivery," Nucleic Acid Therapeutics, Mar. 2018, 17 pages.

Panigaj, M. et al., "Aptamers as Modular Components of Therapeutic Nucleic Acid Nanotechnology," ACS Nano, 2019, p. 12301-12321, vol. 13.

Papargyri, N. et al., "Chemical Diversity of Locked Nucleic Acid-Modified Antisense Oligonucleotides Allows Optimization of Pharmaceutical Properties," Molecular Therapy: Nucleic Acids, Mar. 2020, pp. 706-717, vol. 19.

PCT International Search Report and Written Opinion, PCT Application No. PCT/US2021/025471, Jul. 5, 2021, 16 pages.

Peek, A. S. "Improving Model Predictions for RNA Interference Activities that use Support Vector Machine Regression by Combining and Filtering Features." BMC Bioinformatics, vol. 8, Jun. 6, 2007, pp. 1-29.

Prakash, T. P. et al., "Targeted delivery of antisense oligonucleotides to hepatocytes using triantennary N-acetyl galactosamine improves potency 10-fold in mice," Nucleic Acids Research, 2014, pp. 8796-8807, vol. 42, No. 13.

Ran, F. A. et al., "Double Nicking by RNA-Guided CRISPR Cas9 for Enhanced Genome Editing Specificity," Cell, Sep. 12, 2013, pp. 1380-1389, vol. 154, No. 6.

Reuter, M. S. et al., "The Cardiac Genome Clinic: implementing genome sequencing in pediatric heart disease," Genetics in Medicine, Jun. 2020, pp. 1015-1024, vol. 22, No. 6.

Rivas, E. et al., "A Dynamic Programming Algorithm for RNA Structure Prediction Including Pseudoknots," Journal of Molecular Biology, 1999, pp. 2053-2068, vol. 285.

Rivas, E. et al., "The language of RNA: a formal grammar that includes pseudoknots," Bioinformatics, 2000, pp. 334-340, vol. 16, No. 4.

(56) References Cited

OTHER PUBLICATIONS

Sambrook, J. et al., "Molecular Cloning: A Laboratory Manual," Cold Spring Harbor Laboratory Press, 2001, 23 pages, vol. 1, Third Edition (with title page, table of contents and preface).

Sambrook, J. et al., "Molecular Cloning: A Laboratory Manual," Cold Spring Harbor Laboratory Press, 1989, 30 pages, vol. 1, Second Edition (with title page and table of contents).

Scocchia, A. et al., "Clinical whole genome sequencing as a first-tier test at a resource-limited dysmorphology clinic in Mexico," npj Genomic Medicine, 2019, 12 pages, vol. 4, No. 5.

Shen, W. et al., "Chemical modification of PS-ASO therapeutics reduces cellular protein-binding and improves the therapeutic index," Nature Biotechnology, Jun. 2019, pp. 640-650, vol. 37.

Shpaer, E. G., "GeneAssist, Smith-Waterman and Other Database Similarity Searches and Identification of Motifs," Methods in Molecular Biology, Sequence Data Analysis Guidebook, 1997, pp. 173-187, vol. 70.

Siegfried, N. A. et al., "RNA motif discovery by SHAPE and mutational profiling (SHAPE-MaP)," Nature Methods, Sep. 2014, pp. 959-965, vol. 11, No. 9.

Smith, T. F. et al., "Comparison of Biosequences," Advances in Applied Mathematics, Dec. 1981, pp. 482-489, vol. 2, No. 4.

Wouters, O. J. et al., "Estimated Research and Development Investment Needed to Bring a New Medicine to Market, 2009-2018," JAMA: The Journal of the American Medical Association, 2020, pp. 844-853, vol. 323, No. 9.

Yoon, S. et al., "Aptamers: Uptake mechanisms and intracellular applications," Advanced Drug Delivery Reviews, Sep. 2018, pp. 22-35, vol. 134.

Zhang, J. et al., "PowerBLAST: A New Network BLAST Application for Interactive or Automated Sequence Analysis and Annotation," Genome Research, 1997, pp. 649-656, vol. 7.

Zhou, J. et al., "Aptamers as targeted therapeutics: current potential and challenges," Nature Reviews Drug Discovery, Mar. 2017, pp. 181-202, vol. 16.

United States Office Action, U.S. Appl. No. 17/220,725, filed Aug. 17, 2021, 16 pages.

United States Office Action, U.S. Appl. No. 17/220,725, filed Oct. 22, 2021, 18 pages.

United States Office Action, U.S. Appl. No. 17/220,725, filed Jan. 26, 2022, 17 pages.

United States Office Action, U.S. Appl. No. 17/220,725, filed Apr. 25, 2022, 21 pages.

United States Office Action, U.S. Appl. No. 17/220,725, filed Mar. 14, 2023, 27 pages.

* cited by examiner

OLIGONUCLEOTIDE-BASED MACHINE LEARNING

CROSS REFERENCE TO RELATED APPLICATIONS

This application is a continuation of U.S. application Ser. No. 17/220,725, filed Apr. 1, 2021, now U.S. Pat. No. 12,057,197, which application claims the benefit of U.S. Provisional Application No. 63/005,015, filed Apr. 3, 2020, which is incorporated by reference in its entirety.

SEQUENCE LISTING

The instant application contains a Sequence Listing which has been submitted via Patent Center and is hereby incorporated by reference in its entirety. Said XML copy, created on Aug. 22, 2024, is named 37219-59187US Sequencelisting, and is 52.6 kilobytes in size.

BACKGROUND

Diagnostic genome sequencing is capable of revealing the genetic basis for rare, ultra-rare, and even genetic diseases affecting single individuals. As the cost decreases and availability increases of diagnostic genome sequencing along with other enhanced diagnostic tools, the precise molecular intervention that would provide therapeutic benefit can be known. This is true across therapeutic areas and disease demographics. However, traditional drug discovery processes typically require over a decade of effort and tens to hundreds of millions of dollars to go from therapeutic idea to new approved medicine. This fundamental inefficiency is ultimately what drives the paucity of new drugs being approved in the US and globally, and the increasingly exorbitant pricing of new precision medicines.

Oligonucleotide-based medicines (OBMs) are short nucleic acid polymers, such as DNA or RNA, that are chemically synthesized and modified to confer them with better drug-like properties in living tissues or to modify chemistries or other modifications for diagnostic use. OBMs are designed to engage with native DNA or RNA sequences in the cell by Watson Crick hybridization, and may lead to enzymatic recruitment post-hybridization to achieve the critical mechanism-of-action or elicit biological effect through hybridization alone. In addition, aptamers can be selected or designed to interact with proteins, nucleic acids or other cellular structures through non-hybridization based mechanisms.

The traditional manner of identifying OBMs with desirable pharmacology or chemistries is by trial-and-error screening of a large library of sequences designed against a transcript sequence. The current process is both resource- and time-inefficient, and often lead to sporadic failures at every stage of pre-clinical drug development, clinical drug development, or diagnostic development, where late state failures contributed disproportionately to the cost of creating novel medicines or diagnostic modalities.

There are two foundational barriers preventing the rapid creation of new OBMs that can be affordably engineered and provided to patients with the understanding that they will be safe and effective. Currently, there are no methods that can adequately predict the pharmacology of newly designed OBMs. This forces drug developers to rely on onerous screening processes which are slow and expensive. Secondly, OBMs have limited capacity to reach several cell-types, tissues and organ systems. OBMs have excellent pharmacology throughout a handful of tissues such as the liver and kidney when systemically delivered, and some tissues such as the brain and eye when direct local delivery is an option. However, many pathologies require gene expression modulation in tissues and cells outside these ones.

There is a need for a cost-efficient method of engineering OBMs that are safe and effective with high certainty, and a need to precisely target OBMs to specific tissues or cells. There is also a need for cost-efficient and effective OBMs that can provide precise nucleic acid interactions that underlay many foundational diagnostic instruments.

SUMMARY

Oligonucleotide-based medicine can be designed and tested in silico using a machine-learned model trained on data representative of OBM structure, pharmacology, and effectiveness.

Aspects of the present disclosure include methods for training a machine learned model. Aspects of the present disclosure include methods for generating oligonucleotide-based medicines. Aspects of the present disclosure include systems for carrying out the methods of the present disclosure. Aspects of the present disclosure include a computer readable medium, comprising instructions, that cause a processor to carry out the methods of the present disclosure.

Aspects of the present disclosure include a method for training a machined learned model, comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

Aspects of the present disclosure include a method for generating oligonucleotide-based medicines, comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

In some embodiments, the initial oligonucleotide comprises an oligonucleotide that causes the biophysical effect.

In some embodiments, the biophysical effect comprises one or more of: a biological effect, a chemical effect, and a pharmacological effect.

In some embodiments, the biophysical effect is tolerability.

In some embodiments, the tolerability comprises membrane toxicity.

In some embodiments, tolerability comprises cytotoxicity.

In some embodiments, tolerability comprises immunotoxicity.

In some embodiments, tolerability comprises membrane toxicity. In some embodiments, tolerability comprises an effect that inhibits membrane fluidity. In some embodiments, tolerability comprises a membrane fusion and fission event. In some embodiments, the membrane fusion and fission event result in loss of cellular signaling activity. In some embodiments, the biophysical effect is one or more of: an effect that inhibits the normal flux of ions and an effect that inhibits membrane fluidity. In some embodiments, the biophysical effect is a membrane fusion and fission event that results in loss of cellular signaling activity.

In some embodiments, the biophysical effect is an immune response.

In some embodiments, the biophysical effect is a biological activity of the oligonucleotide and comprises an on-target engagement of the oligonucleotide to a target.

In some embodiments, the biophysical effect is one of inactivity of the oligonucleotide.

In some embodiments, the biophysical effect comprises an off-target engagement of the oligonucleotide to non-target molecules. In some cases, the non-target is a non-target gene.

In some embodiments, the on-target engagement causes the oligonucleotide to perform an effective amount of one or more of: gene expression knock-down, RNA splicing modulatory behavior, gene expression upregulation, gene-editing, RNA-editing, protein specific targeting, receptor specific targeting, enzymatic substrate specific targeting, distribution and uptake into tissues or cells, and interaction with a specific protein or receptor. In some embodiments, the off-target engagement causes the oligonucleotide to perform an effective amount of one or more of: non-target gene expression knock-down, non-target RNA splicing modulatory behavior, non-target gene expression upregulation, non-target gene-editing, non-target RNA-editing, non-target protein specific targeting, non-target receptor specific targeting, non-target enzymatic substrate specific targeting, non-target distribution and uptake into tissues or cells, and non-target interaction with a specific protein or receptor.

In some embodiments, the biophysical effect is a measure of absorption, distribution, metabolism, or excretion of the oligonucleotide.

In some embodiments, the biophysical effect is a measure of pharmacokinetics or pharmacodynamics, and comprises one or more of: substrate-target processing, dynamics, accessibility, inter-cellular distribution, intra-cellular distribution, and time-dependent availability.

In some embodiments, initializing the machine-learned model comprises initializing a set of coefficients each representative of a correlation between n-grams of an oligonucleotide sequence and a presence of the biophysical effect.

In some embodiments, at least one coefficient of the set of coefficients is representative of a correlation between consecutive n-grams within the oligonucleotide and the presence of the biophysical effect.

In some embodiments, the machine-learned model comprises one of: an Ising model, a Potts model, a hidden Markov model, a continuous random field model, and a directed acyclic graphical model.

In some embodiments, the machine-learned model comprises one of: a random forest classifier, a logistic regression, a linear regression, a neural network, a sparsity-driven convex optimization fit, and a support vector machine.

In some embodiments, the first set of oligonucleotides comprise n-gram mutations of the initial oligonucleotide.

In some embodiments, the first set of oligonucleotides comprise gapped n-gram mutations.

In some embodiments, each of the first set of oligonucleotides comprises a single or double n-gram or gapped n-gram mutation of the initial oligonucleotide.

In some embodiments, the first set of oligonucleotides comprise a subset of all single or double n-gram mutations of the initial oligonucleotide.

In some embodiments, the first set of oligonucleotides, when fitted by the initialized machine-learned model, represent a range of probabilities of the biophysical effect.

In some embodiments, determining whether an oligonucleotide corresponds to the biophysical effect comprises performing one or more of: in vitro, in vivo, ex vivo, in situ, and in silico assays on the oligonucleotide.

In some embodiments, determining whether an oligonucleotide corresponds to the biophysical effect comprises simulating, in silico, one or more of: in vitro, in vivo, ex vivo, and in situ assays on the oligonucleotide.

In some embodiments, determining whether an oligonucleotide corresponds to the biophysical effect comprises classifying the oligonucleotide using a synthetic model configured to predict whether the oligonucleotide corresponds to the biophysical effect.

In some embodiments, generating the refined machine-learned model comprises retraining the initialized machine-learned model using the first set of oligonucleotides and whether each of the first set of oligonucleotides corresponds to the biophysical effect.

In some embodiments, generating the refined machine-learned model comprises performing a sparsity-constrained fit on the first set of oligonucleotides and whether each of the first set of oligonucleotides corresponds to the biophysical effect.

In some embodiments, generating the refined machine-learned model comprises generating a new machine-learned model using the first set of oligonucleotides and whether each of the first set of oligonucleotides corresponds to the biophysical effect.

In some embodiments, generating the refined machine-learned model comprises: generating a first updated machine-learned model using the first set of oligonucleotides and whether each of the first set of oligonucleotides corresponds to the biophysical effect; generating a second set of oligonucleotides based on the first updated machine-learned model, each of the second set of oligonucleotides comprising a mutation of the initial oligonucleotide; determining, for each oligonucleotide of the second set of oligonucleotides, whether the oligonucleotide corresponds to the biophysical effect; and generating a second updated machine-learned model using the second set of oligonucleotides and whether each of the second set of oligonucleotides corresponds to the biophysical effect.

In some embodiments, generating the refined machine-learned model further comprises: generating a third set of oligonucleotides, each of the third set of oligonucleotides comprising a generated oligonucleotide; determining, for each oligonucleotide of the third set of oligonucleotides, whether the oligonucleotide corresponds to the biophysical effect; and modifying the second updated machine-learned model using the third set of oligonucleotides and whether each of the third set of oligonucleotides corresponds to the biophysical effect. In some embodiments, the third set of oligonucleotides comprise a randomly or non-randomly generated oligonucleotide.

In some embodiments, the third set of oligonucleotides further comprises approximately equal portions of oligonucleotides predicted to correspond to the biophysical effect and predicted to not correspond to the biophysical effect by the second updated machine-learned model.

In some embodiments, generating an oligonucleotide in the second set of oligonucleotides or the third set of oligonucleotides comprises: identifying an n-gram of an oligonucleotide sequence that strongly corresponds to the biophysical effect; and generating an oligonucleotide comprising a mutation of the identified n-gram of the oligonucleotide sequence.

In some embodiments, generating a refined machine-learned model further comprises iteratively refining the machine-learned model using additional sets of oligonucleotides until a stop condition is satisfied. In some embodiments, the stop condition comprises one or more of: a number of iterations, a threshold predictive performance of the machine-learned model, and a below-threshold increase in predictive performance of the machine-learned model after a refining iteration.

In some embodiments, generating the final set of oligonucleotides using the refined machine-learned model comprises: receiving an identification of a biophysical function to be performed by an oligonucleotide-based medicine (OBM) and an identification of a measure of the biophysical effect; identifying a set of characteristics of an oligonucleotide associated with the biophysical function; and generating, using the refined machine-learned model, a set of oligonucleotides having one or more of the identified set of characteristics and corresponding to the measure of the biophysical effect.

In some embodiments, the biophysical effect comprises one or more of: a biological effect, a chemical effect, and a pharmacological effect.

In some embodiments, the biophysical effect is tolerability. In some embodiments, tolerability comprises one or more of: cytotoxicity, membrane toxicity, and immunotoxicity. In some embodiments, tolerability is cytotoxicity. In some embodiments, tolerability is membrane toxicity. In some embodiments, tolerability is immunotoxicity.

In some embodiments, the biophysical effect is an immune response.

In some embodiments, the biophysical function is a reduction of immune-mediated inflammation.

In some embodiments, the biophysical function is increasing immune-mediated responses.

In some embodiments, the biophysical function is an on-target engagement of the oligonucleotide to a target.

In some embodiments, the on-target engagement causes the oligonucleotide to perform an effective amount of one or more of: gene expression knock-down, RNA splicing modulatory behavior, gene expression upregulation, gene-editing, RNA-editing, protein specific targeting, receptor specific targeting, enzymatic substrate specific targeting, and distribution and uptake into tissues or cells.

In some embodiments, the target is a gene product. In some embodiments, the gene product is an mRNA, a splicing site on a pre-mRNA, a truncated transcript, an aborted transcription product, or an antisense transcript.

In some embodiments, the biophysical effect is a measure of absorption, distribution, metabolism, or excretion of the oligonucleotide within one or more of: a tissue, cell, intracellular spaces, and extracellular spaces.

In some embodiments, the intracellular space comprises blood or cerebrospinal fluid (CSF).

In some embodiments, the measure of the biophysical effect comprises one or more of: a threshold toxicity, a threshold biological activity or biological activity range, a threshold of absorption or absorption range, a threshold distribution, a threshold metabolism, a threshold excretion, a threshold measure of pharmacokinetics, and a threshold measure of pharmacodynamics.

In some embodiments, the biophysical effect is selected to be beneficial for an individual based on the individual's genetics. In some embodiments, generating the set of oligonucleotides comprises selecting one or more of: antisense oligonucleotides (ASO), anti-gene oligonucleotides, CpG oligonucleotides, single-guide RNAs, dual-guide RNAs, targeter RNAs, activator RNAs, and ribozymes.

In some embodiments, the threshold level of hepatotoxicity includes a threshold of ALT and/or AST levels ≤100 U/L at 72 hours after administration of dosing can be trained as "safe" and ALT and/or AST levels ≥200 U/L as "toxic".

In some embodiments, the final set of oligonucleotides comprises a set antisense oligonucleotides (ASO).

In some embodiments, the final set of oligonucleotides comprises a set of anti-gene oligonucleotides.

In some embodiments, the final set of oligonucleotides comprises a set CpG oligonucleotides.

In some embodiments, the final set of oligonucleotides comprises a set single-guide RNAs.

In some embodiments, the final set of oligonucleotides comprises a set dual-guide RNAs.

In some embodiments, the final set of oligonucleotides comprises a set targeter RNAs.

In some embodiments, the final set of oligonucleotides comprises a set activator RNAs.

In some embodiments, the final set of oligonucleotides comprises a set of aptamers.

In some embodiments, the final set of oligonucleotides comprises a set of steric-blocking oligonucleotides.

In some embodiments, the final set of oligonucleotides comprises a set of ASOs to harness RNase H.

In some embodiments, the final set of oligonucleotides comprises a set of tracr RNAs.

In some embodiments, the final set of oligonucleotides comprises a set of RNA interference (RNAi)-based oligonucleotides.

In some embodiments, the final set of oligonucleotides comprises a set of RNA (ADAR)-guiding RNA (AD-gRNAs).

In some embodiments, the final set of oligonucleotides comprises a set of double stranded RNA (dsRNA).

In some embodiments, the final set of oligonucleotides comprises a set of CRISPR RNA (crRNA).

In some embodiments, the biophysical effect is one or more of: cellular uptake and trafficking of the aptamer, binding affinity to the OBM, OBM-aptamer interactions, folded structures of the aptamer, electrostatic interactions, and hybridization energetics and biophysics.

In some embodiments, the folded structure comprises one or more of a bulge, an apical loop, a stem-loop, a 3-way junction, a form helix, an internal loop, a pseudoknot, and a hairpin.

In some embodiments, the final set of oligonucleotides comprises a set of oligonucleotide-aptamer conjugates.

Aspects of the present disclosure include a method for generating oligonucleotide-based medicines, comprising: initializing a probabilistic machine-learned model configured to map an oligonucleotide sequence to a probability of a biophysical effect using an initial oligonucleotide corresponding to the biophysical effect; generating a first set of oligonucleotides by performing single n-gram mutations on the initial oligonucleotide to obtain oligonucleotides mapped to a distributed range of probabilities by the initialized probabilistic machine-learned model; determining, for each oligonucleotide of the first set of oligonucleotides, a first measure of correlation between the oligonucleotide and the biophysical effect based on real-world experimental determination; generating a first refined probabilistic machine-learned model based on the first set of oligonucleotides and the determined first measures of correlation; generating a second set of oligonucleotides, each of the second set of oligonucleotides generated and mapped to a distributed range of probabilities by the first refined probabilistic machine-learned model; determining, for each oligonucleotide of the second set of oligonucleotides, a second measure of correlation between the oligonucleotide and the biophysical effect based on real-world experimental determination; generating a second refined probabilistic machine-learned model based on the second set of oligonucleotides and the determined second measures of correlation; and generating a final set of oligonucleotides using the second refined probabilistic machine-learned model. In some embodiments, each of the second set of oligonucleotides is randomly or non-randomly generated.

In some embodiments, the method further comprises: receiving a set of biophysical requirements for an oligonucleotide-based medicine from a designer; and selecting a subset of the generated final set of oligonucleotides that satisfy the set of biophysical requirements.

In some embodiments, the first set of oligonucleotides comprises 50 or fewer oligonucleotides, between 50 and 100 oligonucleotides, between 100 and 150 oligonucleotides, between 150 and 200 oligonucleotides, between 200 and 300 oligonucleotides, between 300 and 400 oligonucleotides, between 400 and 500 oligonucleotides, between 500 and 750 oligonucleotides, between 750 and 1000 oligonucleotides, between 1000 and 1500 oligonucleotides, between 1500 and 2000 oligonucleotides, between 2000 and 2500 oligonucleotides, between 2500 to 5000 oligonucleotides, or between 5000 to 10000 oligonucleotides.

Aspects of the present disclosure include a method for training a machine learned model, comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a set of oligonucleotides, 2) selecting a subset of the generated set of oligonucleotides such that approximately equal portions of the subset of the generated set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model. In some embodiments, said generating comprises generating a random set of oligonucleotides.

Aspects of the present disclosure include a method for generating a oligonucleotide-based medicines, comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a set of oligonucleotides, 2) selecting a subset of the generated set of oligonucleotides such that approximately equal portions of the subset of the generated set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model. In some embodiments, said generating comprises generating a random set of oligonucleotides.

Aspects of the present disclosure include a system for training a machine learned model, comprising: a hardware processor; and a non-transitory computer-readable storage medium storing executable instructions that, when executed by the hardware processor, cause the system to perform steps comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

Aspects of the present disclosure include a system for generating oligonucleotide-based medicines, comprising: a hardware processor; and a non-transitory computer-readable storage medium storing executable instructions that, when executed by the hardware processor, cause the system to perform steps comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

Aspects of the present disclosure include a system for generating a machine learned model, comprising: a hardware processor; and a non-transitory computer-readable storage medium storing executable instructions that, when executed by the hardware processor, cause the system to perform steps comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

Aspects of the present disclosure include a non-transitory computer-readable storage medium storing executable instructions that, when executed by a hardware processor, cause the hardware processor to perform steps for generating oligonucleotide-based medicines, the steps comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

Aspects of the present disclosure include a system for training a machine learned model, comprising: a hardware processor; and a non-transitory computer-readable storage medium storing executable instructions that, when executed by the hardware processor, cause the system to perform steps comprising: initializing a probabilistic machine-learned model configured to map an oligonucleotide sequence to a probability of a biophysical effect using an initial oligonucleotide corresponding to the biophysical effect; generating a first set of oligonucleotides by performing n-gram mutations on the initial oligonucleotide to obtain oligonucleotides mapped to a distributed range of probabilities by the initialized probabilistic machine-learned model; determining, for each oligonucleotide of the first set of oligonucleotides, a first measure of correlation between the oligonucleotide and the biophysical effect based on real-world experimental determination; generating a first refined probabilistic machine-learned model based on the first set of oligonucleotides and the determined first measures of correlation; generating a second set of oligonucleotides, each of the second set of oligonucleotides generated and mapped to a distributed range of probabilities by the first refined probabilistic machine-learned model; determining, for each oligonucleotide of the second set of oligonucleotides, a second measure of correlation between the oligonucleotide and the biophysical effect based on real-world experimental determination; generating a second refined probabilistic machine-learned model based on the second set of oligonucleotides and the determined second measures of correlation; and generating a final set of oligonucleotides using the second refined probabilistic machine-learned model. In some embodiments, each of the second set of oligonucleotides is randomly or non-randomly generated. For example, when randomly generated, the oligonucleotides can be selected randomly in a way that maps the oligonucleotides to the distribution expected by the first iteration of the model.

Aspects of the present disclosure include a system for generating oligonucleotide-based medicines, comprising: a hardware processor; and a non-transitory computer-readable storage medium storing executable instructions that, when executed by the hardware processor, cause the system to perform steps comprising: initializing a probabilistic machine-learned model configured to map an oligonucleotide sequence to a probability of a biophysical effect using an initial oligonucleotide corresponding to the biophysical effect; generating a first set of oligonucleotides by performing n-gram mutations on the initial oligonucleotide to obtain oligonucleotides mapped to a distributed range of probabilities by the initialized probabilistic machine-learned model; determining, for each oligonucleotide of the first set of oligonucleotides, a first measure of correlation between the oligonucleotide and the biophysical effect based on real-world experimental determination; generating a first refined probabilistic machine-learned model based on the first set of oligonucleotides and the determined first measures of correlation; generating a second set of oligonucleotides, each of the second set of oligonucleotides generated and mapped to a distributed range of probabilities by the first refined probabilistic machine-learned model; determining, for each oligonucleotide of the second set of oligonucleotides, a second measure of correlation between the oligonucleotide and the biophysical effect based on real-world experimental determination; generating a second refined probabilistic machine-learned model based on the second set of oligonucleotides and the determined second measures of correlation; and generating a final set of oligonucleotides using the second refined probabilistic machine-learned model. In some embodiments, each of the second set of oligonucleotides is randomly or non-randomly generated.

Aspects of the present disclosure include a non-transitory computer-readable storage medium storing executable instructions that, when executed by a hardware processor, cause the hardware processor to perform steps for generating oligonucleotide-based medicines, the steps comprising: initializing a probabilistic machine-learned model configured to map an oligonucleotide sequence to a probability of a biophysical effect using an initial oligonucleotide corresponding to the biophysical effect; generating a first set of oligonucleotides by performing n-gram mutations (e.g., single, double, etc.) on the initial oligonucleotide to obtain oligonucleotides mapped to a distributed range of probabilities by the initialized probabilistic machine-learned model; determining, for each oligonucleotide of the first set of oligonucleotides, a first measure of correlation between the oligonucleotide and the biophysical effect based on real-world experimental determination; generating a first refined probabilistic machine-learned model based on the first set of oligonucleotides and the determined first measures of correlation; generating a second set of oligonucleotides, each of the second set of oligonucleotides generated and mapped to a distributed range of probabilities by the first refined probabilistic machine-learned model; determining, for each oligonucleotide of the second set of oligonucleotides, a second measure of correlation between the oligonucleotide and the biophysical effect based on real-world experimental determination; generating a second refined probabilistic machine-learned model based on the second set of oligonucleotides and the determined second measures of correlation; and generating a final set of oligonucleotides using the second refined probabilistic machine-learned model. In some embodiments, each of the second set of oligonucleotides are randomly or non-randomly generated.

Aspects of the present disclosure include a system for training a machine learned model, comprising: a hardware processor; and a non-transitory computer-readable storage medium storing executable instructions that, when executed by the hardware processor, cause the system to perform steps comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a set of oligonucleotides, 2) selecting a subset of the generated set of oligonucleotides such that approximately equal portions of the subset of the generated set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model. In some embodiments, said generating comprises generating a random set of oligonucleotides.

Aspects of the present disclosure include a system for generating oligonucleotide-based medicines, comprising: a hardware processor; and a non-transitory computer-readable storage medium storing executable instructions that, when executed by the hardware processor, cause the system to perform steps comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a set of oligonucleotides, 2) selecting a subset of the generated set of oligonucleotides such that approximately equal portions of the subset of the generated set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model. In some embodiments, said generating comprises generating a random set of oligonucleotides.

Aspects of the present disclosure include a non-transitory computer-readable storage medium storing executable instructions that, when executed by a hardware processor, cause the hardware processor to perform steps for generating oligonucleotide-based medicines, the steps comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a set of oligonucleotides, 2) selecting a subset of the generated set of oligonucleotides such that approximately equal portions of the subset of the generated set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model. In some embodiments, said generating comprises generating a random set of oligonucleotides.

Aspects of the present disclosure include a method for training a machine-learned model, comprising: generating a first set of oligonucleotides by performing n-gram mutations on an initial oligonucleotide to obtain oligonucleotides mapped to a distributed range of probabilities; creating a first training set comprising, for each oligonucleotide of the first set of oligonucleotides, a first measure of correlation between the oligonucleotide and a biophysical effect determined based on real-world experimental determination; training a machine-learned model in a first stage using the first training set, the machine-learned model configured to map an oligonucleotide sequence to a probability of a biophysical effect; generating a second set of oligonucleotides mapped to a distributed range of probabilities by the machine-learned model; creating a second training set comprising, for each oligonucleotide of the second set of oligonucleotides, a second measure of correlation between the oligonucleotide and a biophysical effect determined based on real-world experimental determination; and training the machine-learned model in a second stage using the second training set.

Aspects of the present disclosure include an oligonucleotide, generated according to the methods described herein.

Aspects of the present disclosure include an oligonucleotide-based medicine, generated according to the methods described herein.

BRIEF DESCRIPTION OF THE DRAWINGS

FIG. 10A is an exemplary depiction that reconfirms the separability of off-target driven toxicity (RNase H mediated) vs the far more common OBM sequence-interaction driven toxicities (protein-mediated).

DETAILED DESCRIPTION

Figure 1:
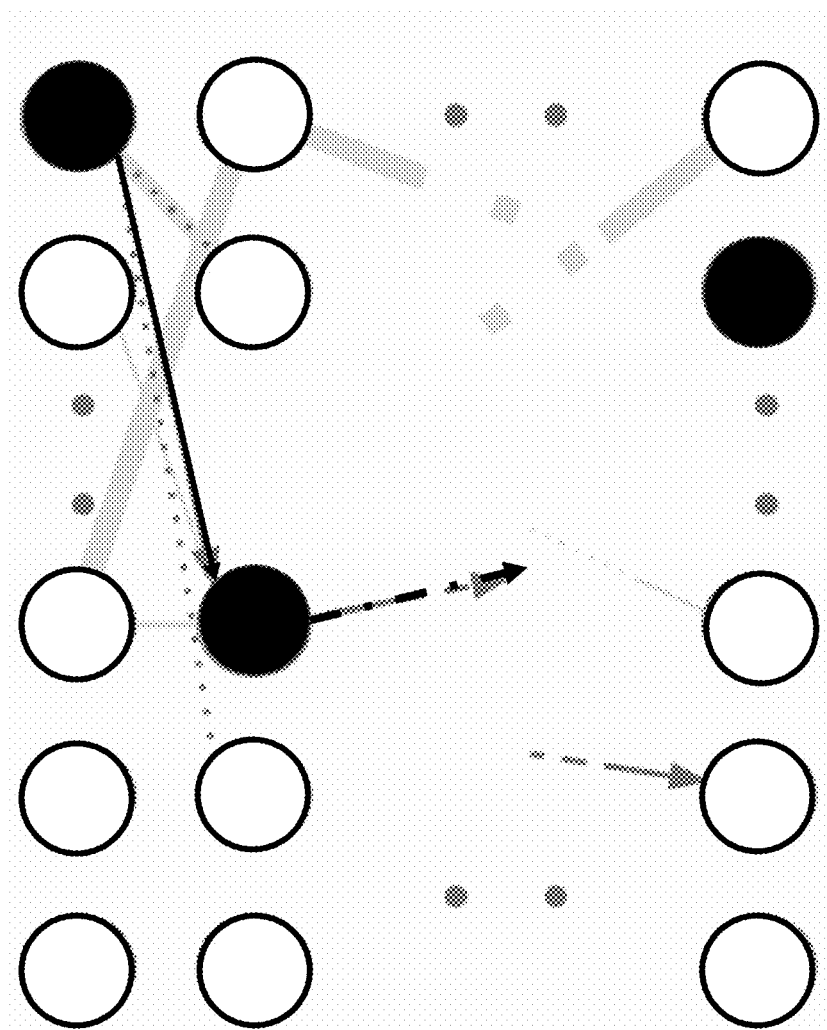
FIG. 1 shows a graphical representation of all possible OBMs. The white circles in each column are the full alphabet space, i.e., all possibilities at each position (row), where the position is along the OBM. For example, for a DNA sequence of length 16 represented in dimer space, there are 15 columns in this graph corresponding to the start position of the dimer in the sequence. There are 16 rows, for 4×4 possible dimer "alphabet" composed of A; C; G; T, namely, [AA; AC; : : : ; GT; TT]. A particular realization of a sequence is a unique set of black nodes, connected by solid black directed edges (arrows). Every node can connect to a subset of all possible nodes in the next row, and these edges are represented by dashed black lines, and for clarity only shown for one node (the black node in the top left corner) in the above graph. The constraint in edge connection is simply consistency in composition of units—in the sequence example, AC dimer can only connect to a dimer starting with C because the dimer representation is overlapping by one base. In general, the representation is not limited to sequences, and can include arbitrary finite chemical space. The solid gray edges are weighted and represent "desirable" paths in this graph to emulate a desirable pharmacology, such as "safe" OBMs.

Aspects of the present disclosure include in silico methods for training a machine learned model. Aspects of the present disclosure include in silico methods for generating oligonucleotide-based medicines (OBMs).

Aspects of the present disclosure include methods for training a machine learned model. Aspects of the present disclosure include methods for generating oligonucleotide-based medicines, e.g., for use in therapeutic applications and/or diagnostic applications. Aspects of the present disclosure include systems for carrying out the methods of the present disclosure. Aspects of the present disclosure include a computer readable medium, comprising instructions, that cause a processor to carry out the methods of the present disclosure.

Oligonucleotide-Based Medicines/Drugs are polymeric molecules comprising natural and synthetic derivatives of nucleic acids. Oligonucleotide-based medicines can be used for, for example, therapeutic applications, personalized medicine, and/or diagnostic applications.

Reference will now be made in detail to several embodiments, examples of which are illustrated in the accompanying figures. It is noted that wherever practicable similar or like reference numbers may be used in the figures and may indicate similar or like functionality.

I. Definitions

Unless defined otherwise, all technical and scientific terms used herein have the meaning commonly understood by a person skilled in the art to which this description belongs. As used herein, the following terms have the meanings ascribed to them below.

As used herein, the term "individual" refers to a human or animal individual. As used herein, the term "healthy individual" refers to an individual presumed to not have a disease or disorder.

The terms "biophysical", "biophysical effect", and "biophysical function" generally refer to biological, chemical, and physical properties of an oligonucleotide that determine its tolerability, functionality, activity, and effects within a living organism, cell or cell extract.

As used herein, the term "pharmacology" refers to studying how of an oligonucleotide-based medicine affects a biological system, for example, by studying its tolerability, functionality, activity, pharmacokinetics, pharmacodynamics, absorption, distribution, metabolism, and extraction (ADME), and its tolerability in in-vitro and in-vitro.

As used herein, the term "oligonucleotide-based medicine" refers to an oligonucleotide-based therapeutic for treatment of diseases, such as genetic diseases.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. "Oligonucleotide" generally refers to polynucleotides of between about 5 and about 100 nucleotides of single- or double-stranded DNA or RNA. For the purposes of this disclosure, there is no upper limit to the length of an oligonucleotide. Oligonucleotides are also known as oligomers or oligos. In some embodiments, oligonucleotides of the present disclosure comprise base modifications, chemical modifications, or combinations thereof. In some embodiments, oligonucleotides of the present disclosure comprise computer representation of the molecules in formats including but not limited to hierarchical editing language for macromolecules (HELM) or simplified molecular-input-line entry system (SMILES) strings.

As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as, Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179, which are incorporated herein by reference. Examples of microRNAs include any RNA that is a fragment of a larger RNA or is a miRNA, siRNA, stRNA, sncRNA, tncRNA, snoRNA, smRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

A "small interfering" or "short interfering RNA" or siRNA is a RNA duplex of nucleotides that is targeted to a gene of interest (a "target gene"). An "RNA duplex" refers to the structure formed by the complementary pairing between two regions of a RNA molecule. siRNA is "targeted" to a gene in that the nucleotide sequence of the duplex portion of the siRNA is complementary to a nucleotide sequence of the targeted gene. In some embodiments, the length of the duplex of siRNAs is less than 30 nucleotides. In some embodiments, the duplex can be 29, 28, 27, 26, 25, 24, 23, 22, 21, 20, 19, 18, 17, 16, 15, 14, 13, 12, 11 or 10 nucleotides in length. In some embodiments, the length of the duplex is 19-25 nucleotides in length. The RNA duplex portion of the siRNA can be part of a hairpin structure. In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some embodiments, the overhang is a 3' or a 5' overhang 0, 1, 2, 3, 4 or 5 nucleotides in length.

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moeity. Preferred alkyl (e.g., alkyl, caboxyalkyl, etc.) moieties comprise of about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like. Other examples are well known to those of skill in the art.

A nucleobase may be composed in a nucleoside or nucleotide, using any chemical or natural synthesis method described herein or known to one of ordinary skill in the art. Such nucleobase may be labeled or it may be part of a molecule that is labeled and contains the nucleobase.

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar.

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Hybridization conditions and post-hybridization washes are useful to obtain the desired determined stringency conditions of the hybridization. One set of illustrative post-hybridization washes is a series of washes starting with 6.times.SSC (where SSC is 0.15 M NaCl and 15 mM citrate buffer), 0.5% SDS at room temperature for 15 minutes, then repeated with 2.times.SSC, 0.5% SDS at 45° C. for 30 minutes, and then repeated twice with 0.2.times.SSC, 0.5% SDS at 50° C. for 30 minutes. Other stringent conditions are obtained by using higher temperatures in which the washes are identical to those above except for the temperature of the final two 30 minute washes in 0.2.times.SSC, 0.5% SDS, which is increased to 60° C. Another set of highly stringent conditions uses two final washes in 0.1.times.SSC, 0.1% SDS at 65° C. Another example of stringent hybridization conditions is hybridization at 50° C. or higher and 0.1.times.SSC (15 mM sodium chloride/1.5 mM sodium citrate). Another example of stringent hybridization conditions is overnight incubation at 42° C. in a solution: 50% formamide, 5.times.SSC (150 mM NaCl, 15 mM trisodium citrate), 50 mM sodium phosphate (pH 7.6), 5.times.Denhardt's solution, 10% dextran sulfate, and 20 mug/ml denatured, sheared salmon sperm DNA, followed by washing the filters in 0.1.times.SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), J. Mol. Biol. 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See Meth. Mol. Biol. 70: 173-187 (1997). Also, the GAP program using the Needleman and Wunsch alignment method can be utilized to align sequences. See J. Mol. Biol. 48: 443-453 (1970).

"Complementary," as used herein, refers to the capacity for precise pairing between two nucleotides of a polynucleotide (e.g., an antisense polynucleotide) and its corresponding target polynucleotide. For example, if a nucleotide at a particular position of a polynucleotide is capable of hydrogen bonding with a nucleotide at a particular position of a target nucleic acid (e.g., a microRNA), then the position of hydrogen bonding between the polynucleotide and the target polynucleotide is considered to be a complementary position. The polynucleotide and the target polynucleotide are complementary to each other when a sufficient number of complementary positions in each molecule are occupied by nucleotides that can hydrogen bond with each other. Thus, "specifically hybridizable" and "complementary" are terms which are used to indicate a sufficient degree of precise pairing or complementarity over a sufficient number of nucleotides such that stable and specific binding occurs between the polynucleotide and a target polynucleotide.

It is understood in the art that the sequence of a polynucleotide need not be 100% complementary to that of its target nucleic acid to be specifically hybridizable or hybridizable. Moreover, a polynucleotide may hybridize over one or more segments such that intervening or adjacent segments are not involved in the hybridization event (e.g., a loop structure or hairpin structure). A subject polynucleotide can comprise at least 70%, at least 80%, at least 90%, at least 95%, at least 99%, or 100% sequence complementarity to a target region within the target nucleic acid sequence to which they are targeted. For example, an antisense nucleic acid in which 18 of 20 nucleotides of the antisense compound are complementary to a target region, and would therefore specifically hybridize, would represent 90 percent complementarity. In this example, the remaining non-complementary nucleotides may be clustered or interspersed with complementary nucleotides and need not be contiguous to each other or to complementary nucleotides. As such, an antisense polynucleotide which is 18 nucleotides in length having 4 (four) noncomplementary nucleotides which are flanked by two regions of complete complementarity with the target nucleic acid would have 77.8% overall complementarity with the target nucleic acid. Percent complementarity of an oligomeric compound with a region of a target nucleic acid can be determined routinely using BLAST programs (basic local alignment search tools) and Power-BLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a biophysical effect" includes a plurality of such biophysical effects and reference to "the oligonucleotide" includes reference to one or more oligonucleotides and equivalents thereof known to those skilled in the art, and so forth. It is further noted that the claims may be drafted to exclude any optional element. As such, this statement is intended to serve as an antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

II. Overview of Method

Aspects of the present disclosure provide methods of training a machine learned model, generating OBMs, and characterizing OBM sequence-pharmacology mapping for engineering safe and effective OBMs. Aspects of the present disclosure include initializing and training a machine-learned model for mapping OBM sequence pharmacology, including mapping the sequence of base and other nucleotide chemistries, and biochemical properties, and biophysical properties to the pharmacological effects.

In some embodiments, the methods of the present disclosure are based on the observation that OBMs have limited monomeric diversity overall, are linear polymers with (possibly distinct) diversity of (possibly overlapping) monomers at each position along the polymer, and can, without loss of generality, be represented as a novel mathematical graph providing a probabilistic language to quantify its pharmacological readout as (multi-) monomeric contributions (e.g. factors).

In some embodiments, the methods of the present disclosure are based on the assumption that OBM pharmacology is driven by interaction with enzymes and proteins, which primarily interact with the OBM in motifs and is modulated by the three-dimensional conformations of the OBM and base-pairing interactions.

Aspects of the present disclosure include methods for generating oligonucleotide-based medicines (OBMs), comprising: initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

In some embodiments, the methods described in the present disclosure quantitatively map OBM sequence and chemistry features to pharmacology. In some embodiments, pharmacological endpoints comprise tissue distribution and productive uptake (ADME, subcellular localization, etc.), targetability of RNA (accessibility, (co-)transcriptional dynamics of RNA, etc.), hybridization, specificity and enzymatic rules (edit tolerance and sequence preference). In some embodiments, pharmacological endpoints comprise cytotoxicity including hepato, renal, cardio and neurotoxicity. In some embodiments, pharmacological endpoints comprise immunogenicity and/or immunostimulatory effects. In some embodiments, pharmacological endpoints comprise membrane toxicity, including acute neurotoxicity and cardiotoxicity. In some embodiments, neurotoxicity is acute or delayed neurotoxicity.

In another embodiment, methods provided herein create in silico datasets. In some embodiments, in silico data sets comprise biophysical models parameterizing RNA dynamics. In some embodiments, in silico data sets comprise quantitative models of pharmacology. In some embodiments, in silico data sets comprise quantitative models of mechanism-of-action. In some embodiments, in silico data sets comprise ML/AI for molecular design. In some embodiments, ML/AI models are specific to the biophysics and mechanisms of polymeric nucleic acids. In some embodiments, in silico data sets comprise quantum chemistry of nucleic acids.

In another embodiment, methods described herein provide the capability to design and engineer optimal (safe and efficacious) OBMs in days, for multiple gene-modulatory mechanisms of OBMs, delivering best-in-industry efficacy and safety profiles unattainable by traditional screening campaigns. In another embodiment, methods described herein provide novel tissue targeting using nucleic acid building blocks.

Methods provided herein can be used to predict and engineer optimal precise nucleic acid interactions that underlay many foundational diagnostic instruments. In some embodiments, provided methods predict, engineer or optimize nucleic acid interactions of any DNA nanotechnology.

In some embodiments, diagnostic instruments amenable to provided methods comprise microarrays that directly measure hybridization events. In some embodiments, methods of the present disclosure can be used to predict, design, or modify for optimization of nucleic acids used in microarray platforms. In some embodiments, the oligonucleotides used in an oligonucleotide-based array can be designed to provide broad genome coverage with higher probe density in regions associated with specific disorders or can include large-scale genomic coverage for identifying many diseases or disorders. In some embodiments, the methods of the present disclosure can be used to predict, modify, or design exon-level oligonucleotide probe coverage for specific genes.

In some embodiments, provided methods predict and engineer custom micropatterned surfaces that leverage hybridization to trap nucleic acid-tagged macromolecules (including but not limited to proteins, antibodies, sugars and lipids), to specific coordinates on a plate (e.g., DNA technology to engineer the nucleic acid topology of micron-sized ELISA beads).

By way of another example, specific nucleic acid structures needed to be formed to facilitate sequencing readouts on nanopore and other sequencing platforms (e.g., PacBio, Illumina, Ion Torrent (Thermo Fisher Scientific), BGI Genomics, PacBio and Oxford Nanopore Technologies) are predicted or engineered by the provided methods. For example, oligonucleotides that can be used in such sequencing platforms include, but are not limited to: amplification primer sequences, sequences used for hybridization capture, adapter sequences, barcode sequences, unique molecular identifiers (UMIs), biotinylated oligonucleotide probes, primers that are specific to the sequencing platform or method used, aptamers for binding to or targeting proteins, cleavage assays for detection, aptamer-nanomaterials, and the like. In some embodiments, oligonucleotides produced or predicted by the present methods can be used in hybrid capture methods and/or amplicon-based methods, e.g., for example oligonucleotides used for hybrid capture methods such as SureSelect (Agilent Technologies) and SeqCap (Roche), or oligonucleotides used for amplicon-based methods such as HaloPlex (Agilent Technologies) and AmpliSeq (Ion Torrent).

In some embodiments, provided methods predict or engineer chemistries for multiplexed Next Generation Sequencing (NGS) assays that are either more or less tolerant to mismatches with library making enzymes (e.g., reverse transcriptase).

In some embodiments, provided methods predict or engineer oligonucleotides used in DNA microarrays such as DNA microarrays developed by Illumnia, Affymetrix, Agilent, Scienion AG, Applied Microarrays, Arrayit, Arrayit, Biometrix Technology, Savyon Diagnostics, and WaferGen.

In some embodiments, provided methods predict or engineer oligonucleotides used in microarrays for analysis of gene expression, genotyping, and genome cytogenetics.

In some embodiments, oligonucleotides generated by the method provided can produce adapters that are added to both ends of the DNA/RNA fragments during library preparation prior to sequencing. The fragment is attached to the surface of the flow cell by means of oligonucleotides on the surface that have a nucleotide sequence complementary to the adapters allowing the hybridization and the subsequent bridge amplification, forming a double-strand bridge. Optimization of oligonucleotides (e.g., optimization of attachment to flow cell and/or fragments, predicted for stability, etc.) can be provided by the methods described herein. Moreover, oligonucleotides can be predicted or developed by the methods described herein for attachment of oligonucleotides to fluorophores.

In some embodiments, the oligonucleotides predicted and/or developed by the methods described herein can be used or tailored for diagnostic imaging modalities.

Surprisingly, the methods provided herein engineer and predict all OBM classes by rapidly creating highly informative datasets for building machine learning (ML) and artificial intelligence (AI) models for predictive pharmacology. OBM classes include an enzyme class comprising engaging or editing enzymes such as CRISPR, RNase H, RNAi, ADAR, etc. In some embodiments, methods provided herein may be used to engineer or predict oligonucleotides used for CRISPR and other editing based or enzymatic diagnostics that rely on modified or selective guide strands driving a specific reaction to happen at a duplexed locus.

OBM classes also include a steric class comprising steric blocking mechanisms of a specific site via modulation of splicing, RBP binding, secondary structure, co- & post-transcriptional modification of coding/non-coding RNA processing, etc., all of which are leveraged in molecular diagnostics. In some embodiments, provided methods engineer and optimize site-specific steric interactions.

Moreover, one surprising aspect of the provided methods was that by regressing on the observed pharmacology, for example, target-gene modulation in patients, optimal and maximal tolerated dose was quantified and predicted precisely. In some embodiments, the platform was able to accurately and efficiently predict the expected maximum modulation obtainable in patients. In some embodiments, predicted maximum modulation is directly used to understand the applicability of OBMs to treating patients that require a certain level of modulation. In some embodiments, provided methods are applied to combinatorial treatment to predict optimal OBM dosing to understand the potential additive or synergistic effects of administering two or more OBMs, either simultaneously or in series. In yet another embodiment, provided methods predict optimal dosing for targeted delivery of known cytotoxic OBMs to deliver the exact dosing needed to kill a cell, such as cancer cells, fibrotic tissue, etc.

For example, the methods of the present disclosure can be used to find an optimal dose of OBMs alone or in combination with other OBMs, agents, or drugs. Such optimal doses would reduce or eliminate toxicity in the patient. In some embodiments, the optimal dose can include a dosage range that is lower than the "expected" or publicly known dosage range of the oligonucleotide. In some embodiments, the optimal dose can include a dosage range that is higher than the "expected" or publicly known dosage range of the oligonucleotide.

In some embodiments, the methods of the present disclosure can be used to find an optimal dose of OBMs for a particular patient population, treatment indication, and the like.

II.A. Oligonucleotide-Based Medicines (OBMs)

In some embodiments, the OBMs of the present disclosure are oligonucleotides designed to engage with native DNA or RNA sequences in the cell by Watson Crick hybridization. In some embodiments, such hybridization results in enzymatic recruitment post-hybridization to achieve a biophysical function (e.g. desired function). In some embodiments, the biophysical function includes, but is not limited to, one or more of gene editing, gene express knock-down, gene expression upregulation, RNA splicing modulatory behavior, RNA-editing, protein specific targeting, receptor specific targeting, enzymatic substrate specific targeting, and distribution and update into tissues or cells.

In some embodiments, the oligonucleotide has a length ranging from 10 nucleotides to about 100 nucleotides. In some embodiments, the oligonucleotide has a length ranging from about 10 nucleotides to about 20 nucleotides, about 20 nucleotides to about 30 nucleotides, about 30 nucleotides to about 40 nucleotides, about 40 nucleotides to about 50 nucleotides, about 50 nucleotides to about 60 nucleotides, about 60 nucleotides to about 70 nucleotides, about 70 nucleotides to about 80 nucleotides, about 80 nucleotides to about 90 nucleotides, or about 90 nucleotides to about 100 nucleotides. In certain embodiments, the oligonucleotide has a length ranging from about 10 nucleotides to about 15 nucleotides, about 15 nucleotides to about 20 nucleotides, about 20 nucleotides to about 25 nucleotides, about 25 nucleotides to about 30 nucleotides, about 30 nucleotides to about 35 nucleotides, about 35 nucleotides to about 40 nucleotides, about 40 nucleotides to about 45 nucleotides, or about 45 nucleotides to about 50 nucleotides. In some embodiments, the length of the oligonucleotide ranges from 12 nucleotides to 22 nucleotides. In certain embodiments, the oligonucleotide has a length of from 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides. In some embodiments, the oligonucleotide has a length of 12 nucleotides. In some embodiments, the oligonucleotide has a length of 13 nucleotides. In some embodiments, the oligonucleotide has a length of 14 nucleotides. In some embodiments, the oligonucleotide has a length of 15 nucleotides. In some embodiments, the oligonucleotide has a length of 16 nucleotides. In some embodiments, the oligonucleotide has a length of 17 nucleotides. In some embodiments, the oligonucleotide has a length of 18 nucleotides. In some embodiments, the oligonucleotide has a length of 19 nucleotides. In some embodiments, the oligonucleotide has a length of 20 nucleotides. In some embodiments, the oligonucleotide has a length of 21 nucleotides. In some embodiments, the oligonucleotide has a length of 22 nucleotides.

In some embodiments, an oligonucleotide includes, but is not limited, to an antisense oligonucleotide (ASO), anti-gene oligonucleotides, CpG oligonucleotides, single-guide RNA (sgRNA), dual-guide RNA, targeter RNA (e.g., targeted coding RNA such as a protein-encoding gene or targeted non-coding RNA), activator RNA, ribozymes, tracr RNA, Ribonuclease H (RNase H) harnessing oligonucleotides, RNA interference (RNAi)-based oligonucleotides, RNA (ADAR)-guiding RNA (AD-gRNAs), double stranded RNA (dsRNA), CRISPR RNA(crRNA), steric-blocking oligonucleotide (SBO), and the like. Targeted non-coding RNA includes, but is not limited to, tRNA, rRNA, snoRNA, siRNA, miRNA, long ncRNA, etc. In some embodiments, the final set of oligonucleotides comprises a set of antisense oligonucleotides (ASO). In some embodiments, the final set of oligonucleotides comprises a set of anti-gene oligonucleotides. In some embodiments, the final set of oligonucleotides comprises a set of CpG oligonucleotides. In some embodiments, the final set of oligonucleotides comprises a set of single-guide RNAs. In some embodiments, the final set of oligonucleotides comprises a set of dual-guide RNAs. In some embodiments, the final set of oligonucleotides comprises a set of targeter RNAs. In some embodiments, the final set of oligonucleotides comprises a set of activator RNAs. In some embodiments, the final set of oligonucleotides are oligonucleotides directed to modulate gene expression via a range of processes including, but not limited to: RNAi, target degradation by RNase H-mediated cleavage, splicing modulation, non-coding RNA inhibition, gene activation and programmed gene editing.

In some embodiments, the oligonucleotide is an antisense oligonucleotide (ASO). In some embodiments, ASO can bind to a messenger RNA (mRNA) produced by a gene and inactivate it, effectively turning that gene "off". In some embodiments, the strand may be targeted to bind to a splicing site on pre-mRNA and modify the exon content of an mRNA. In some embodiments, the ASO is an ASO gapmer. ASOs in the form of a "gapmer" can be used to suppress gene expression by degrading target mRNA via an RNase H mechanism. Gapmer ASOs have a central DNA region required to support the RNase H activity and two ribonucleotide wings to increase target binding affinity of the ASOs. Another category of ASOs are steric blockers, which are typically composed uniformly of ribonucleotides and bind to pre-mRNA in the nucleus to alter mRNA splicing by blocking the binding of certain splicing factors to the mRNA. In some embodiments, the oligonucleotide is a mixmer oligonucleotide that acts as an efficient steric block to mediate a phenotype without destroying a target RNA. In some embodiments, the mixmer oligonucleotide comprises LNA and DNA nucleosides that are interspersed throughout the sequence of the oligonucleotide.

In some embodiments, the oligonucleotide is an axiomer antisense oligonucleotide or a self-looping antisense oligonucleotide. In certain embodiments, the oligonucleotide is used for targeted editing of RNA, characterized by a sequence that is complementary to a target RNA sequence and by the presence of a stem-loop structure that includes a recruitment sequence. In some embodiments, the recruitment sequence acts in recruiting a natural ADAR enzyme present in the cell to the dsRNA formed by hybridization of the target sequence with the targeting portion of the target sequence.

In some embodiments, the oligonucleotide is an antisense RNA oligonucleotide that redirects endogenous ADAR to new sites by making editable structures using the antisense RNA oligonucleotide. In some embodiments, the oligonucleotide is an antisense oligonucleotide that recruits endogenously expressed ADARs.

In some embodiments, the ASO is designed to harness an RNase H (e.g. RNase H1) mechanism. RNase H1 recognizes the duplex formed between a DNA-containing ASO and a target RNA through its RNA-binding domain. In order to cleave the target RNA, the RNase H1 catalytic domain needs at least 5 consecutive DNA/RNA base pairs. In some embodiments, the ASO is an ASO that harness RNase H1 and include a central stretch of 8-10 DNA nucleotides. In some embodiments the ASO is an intron-targeted ASO. In some embodiments the ASO is an exon-targeted ASO.

In some embodiments, the oligonucleotide is a siRNA. In some embodiments, the oligonucleotide is a sgRNA. In some embodiments, the oligonucleotide is a dual-guide RNA. In some embodiments, the oligonucleotide is an anti-gene oligonucleotide. In some embodiments, the oligonucleotide is a CpG oligonucleotide. In some embodiments, the oligonucleotide is a targeter RNA. In some embodiments, the targeter RNA is a protein-encoding gene. In some embodiments, the targeter RNA is a non-coding RNA, such as, but not limited to, a tRNA, a rRNA, a snoRNA, an miRNA, an siRNA, an RNAi, or a long ncRNA. In some embodiments, the oligonucleotide is a CRISPR RNA (crRNA). In some embodiments, the oligonucleotide is an activator RNA. In some embodiments, the oligonucleotide is a ribozyme. In some embodiments, the oligonucleotide is an aptamer.

In some embodiments, the oligonucleotide is an siRNA. siRNA binds to a target mRNA mainly in the cytoplasm to down-regulate gene expression post-transcriptionally via the RNA interference (RNAi) mechanism. siRNAs may be designed to target a gene's mRNA sequence to silence its expression via the RNAi mechanism, for maximizing treatment outcomes. In some embodiments, siRNAs have endogenous RNA bases or chemically modified nucleotides. In some embodiments, modifications can impart increased stability and/or increased cellular potency. The siRNA can have varying lengths (e.g., 10-200 bps) and structures (e.g., hairpins, single/double strands, bulges, nicks/gaps, mismatches) and are processed in cells to provide active gene silencing. In some embodiments, the oligonucleotide is a double stranded siRNA. A double-stranded siRNA (dsRNA) can have the same number of nucleotides on each strand (blunt ends) or asymmetric ends (overhangs). An overhang of 1-2 nucleotides, for example, can be present on the sense and/or the antisense strand, as well as present on the 5'- and/or the 3'-ends of a given strand.

In some embodiments, the oligonucleotide is a sgRNA. In some embodiments, the sgRNA is a targeting sequence that hybridizes to a target sequence of a target DNA. In some embodiments, the sgRNA comprises a targeting sequence that hybridizes to a target sequence of a target DNA, and a protein-binding domain that interacts with a Cas9 protein. In some embodiments, the desired sgRNA increases site-specific modification of the target DNA, e.g., for example, by homologous directed repair (HDR), or non-homologous end joining (NHEJ).

In some embodiments, the oligonucleotide is a dual-guide RNA. A dual guide RNA can be designed using the method of the present disclosure to allow for controlled (i.e., conditional) binding of a targeter-RNA with an activator-RNA. Because a dual guide RNA is not functional unless both the activator-RNA and the targeter-RNA are bound in a functional complex with Cas9, a dual guide RNA can be inducible (e.g., drug inducible) by rendering the binding between the activator-RNA and the targeter-RNA to be inducible. As one non-limiting example, RNA aptamers can be used to regulate (i.e., control) the binding of the activator-RNA with the targeter-RNA. Accordingly, the activator-RNA and/or the targeter-RNA can include an RNA aptamer sequence.

In some embodiments, the oligonucleotide is Cas guide RNAs that bind to and provide sequence specificity to a Cas protein or Cas variants thereof (e.g., guide RNA that binds to and provides sequence specificity to a Cas variant thereof). In some embodiments, the oligonucleotide is a Cas5 guide RNA or variant thereof (e.g., guide RNA that binds to and provides sequence specificity to a Cas5 variant thereof). In some embodiments, the oligonucleotide is a Cas6 guide RNA or variant thereof (e.g., guide RNA that binds to and provides sequence specificity to a Cas6 variant thereof). In some embodiments, the oligonucleotide is a Cas7 guide RNA or variant thereof (e.g., guide RNA that binds to and provides sequence specificity to a Cas7 variant thereof). In some embodiments, the oligonucleotide is a Cas9 guide RNA or variant thereof (e.g., guide RNA that binds to and provides sequence specificity to a Cas9 variant thereof). In some embodiments, the oligonucleotide is a Cas13 guide RNA or variant thereof (e.g., guide RNA that binds to and provides sequence specificity to a Cas13 variant thereof. In some embodiments, the oligonucleotide is a Cas12 guide RNA or variant thereof (e.g., guide RNA that binds to and provides sequence specificity to a Cas12 variant thereof). In some embodiments, the oligonucleotide is a Cas14 guide RNA or variant thereof (e.g., guide RNA that binds to and provides sequence specificity to a Cas14 variant thereof).

In some embodiments, the oligonucleotide is an adenosine deaminase acting on RNA (ADAR)-guiding RNA (AD-gRNAs). For example, AD-gRNA can direct A-to-I RNA editing activity of native human ADAR2 into a programmable target site. In some embodiments, the oligonucleotide is a short-chain AD-gRNA (shAD-gRNA). In some embodiments, the AD-gRNA is an antisense RNA oligonucleotide that is a guide to deliver the catalytic domain of engineered ADARs to new sites, e.g., similar to CRISPR oligonucleotide guides that deliver Cas nucleases.

In some embodiments, the oligonucleotide is an aptamer. In some embodiments, the oligonucleotide is an RNA aptamer. Aptamers are known in the art and are generally a synthetic version of a riboswitch. The terms "RNA aptamer" and "riboswitch" are used interchangeably herein to encompass both synthetic and natural nucleic acid sequences that provide for inducible regulation of the structure (and therefore the availability of specific sequences) of the nucleic acid molecule (e.g., RNA, DNA/RNA hybrid, etc.) of which they are part. RNA aptamers usually comprise a sequence that folds into a particular structure (e.g., a hairpin, stem-loop, pseudoknot, etc.), which specifically binds a particular target molecule. In some embodiments, binding of the target molecule causes a structural change in the folding of the RNA, which changes a feature of the nucleic acid of which the aptamer is a part. In some embodiments, RNA aptamer sequences can be appended to or inserted within a guide RNA molecule, such as MS2, PP7, Qβ, and other aptamers. Proteins that specifically bind to these aptamers can be fused to a translational repression domain, a ribonuclease, or a domain that affects RNA stability. This aptamer-effector domain fusion can be used to target the target RNA because the endonuclease protein and gRNA complex will guide the aptamer protein-effector domain in proximity to the target RNA.

In some embodiments, the oligonucleotide is a DNA-based or RNA-based oligonucleotide. In some embodiments, the oligonucleotide is selected from a locked nucleic acid (LNA) oligonucleotide, a constrained ethyl (cEt) oligonucleotide, a bridged nucleic acid (BNA) oligonucleotide (e.g., including but not limited to a 2'-O,4'-C-ethylene-bridged nucleic acid (ENA) oligonucleotide and an amido-bridged nucleic acid (AmNA) oligonucleotide), a Morpholino oligonucleotide, a 2'-O-methyl RNA (MOE) oligonucleotide, an antagomir, a steric-blocking oligonucleotide (SBO) that inhibits miRNA maturation, or a steric-blocking oligomer that blocks a target site of an mRNA transcript. Steric-blocking oligonucleotides (SBOs). SBOs are short, single-stranded nucleic acids designed to modulate gene expression by binding to mRNA and blocking access from cellular machinery such as splicing factors. SBOs have the potential to bind to near-complementary sites in the transcriptome, causing off-target effects. In certain embodiments, the ASO is a locked nucleic acid. In some embodiments, the oligonucleotide is a steric blocking oligonucleotide. In some embodiments, the steric blocking oligonucleotide can include chemical modifications that can simultaneously inhibit multiple members of an miRNA family. In some embodiments, the oligonucleotide is a phosphorodiamidate morpholino oligonucleotide that has a charge-neutral nucleic acid chemistry in which the five-membered ribose heterocycle is replaced by a six-membered morpholine ring. In some embodiments, the oligonucleotide is a PMO-based steric block ASO.

In some embodiments, the oligonucleotide is a constrained ethyl (cEt) oligonucleotide. In some embodiments, the oligonucleotide is a 2'-O,4'-C-ethylene-bridged nucleic acid (ENA). In some embodiments, the oligonucleotide is a 2',4'-constrained 2'-O-ethyl (cEt) bridged nucleic acid (BNA). In some embodiments, the oligonucleotide is an amido-bridged nucleic acid (AmNA).

II.B. Screening for Biophysical Effects

The method of the present disclosure screens for, using the machine-learned models described herein, OBMs that correspond to one or more biological effects and that perform one or more biophysical functions.

The methods of the present disclosure include initializing a machine-learned model configured to map an oligonucleotide sequence to a probability of a biophysical effect; determining, for each oligonucleotide of a first set of oligonucleotides, whether the oligonucleotide corresponds to the biophysical effect; and generating a refined machine-learned model using the first set of oligonucleotides and whether each of the first set of oligonucleotides corresponds to the biophysical effect.

In some embodiments, the biophysical effect includes one or more of: a biological effect, a chemical effect, and a pharmacological effect.

In some embodiments, the methods comprise measuring the biophysical effect. In some embodiments, measuring the biophysical effects comprises quantifying the biophysical effect, for instance evaluating a toxicity of an oligonucleotide on a scale of 0.0 to 1.0. In some embodiments, measuring the biophysical effect comprises one or more of: comparing the biophysical effect to a threshold (such as a toxicity threshold, a biological activity threshold, a distribution threshold, a metabolism threshold, an excretion threshold, a threshold measure of pharmacokinetics or pharmacodynamics) or to a range (such as a biological activity range or an absorption range).

In some embodiments, the biophysical effect is a CBC analysis on blood. In some embodiments, the biophysical effect is a measure of one or more of: neutrophils (%), neutrophil (/uL), reticulocytes (%), WBC (K/uL), absolute reticulocyte (K/uL), RBC (M/uL), HGB (g/dL), lymphocyte (/uL), lymphocytes (%), nucleated RBC (/100 WBC), HCT (%), monocyte (/uL), monocytes (%), polychromasia, anisocytosis, eosinophil (/uL), eosinophils (%), MCV (fL), basophil (/uL), basophils (%), MCH (pg), poikilocytosis, heinz bodies, MCHC (g/dL), metamyelocyte (/uL), metamyelocyte (%), myelocyte (/uL), platelet estimate, myelocyte (%) platelet count (K/uL), promyelocyte (/uL), promyelocyte (%) and combinations thereof.

In some embodiments, the biophysical effect is a body or tissue weight. In some embodiments, the biophysical effect is one or more of body weight, tissue weight, urine collection and volume, serum and urinary analysis, kidney collection, and liver collection.

In some embodiments, the biophysical effect is a tolerability. In some embodiments, tolerability, used in its conventional sense, refers to the degree to which an adverse effect of the oligonucleotide can be tolerated. In some embodiments, the tolerability includes toxicity. In some embodiments, toxicity comprises cytotoxicity. In some embodiments, toxicity comprises membrane toxicity. In some embodiments, toxicity comprises immunotoxicity. In some embodiments, toxicity comprises nephrotoxicity. In some embodiments, toxicity comprises hepatotoxicity. In some embodiments, toxicity comprises neurotoxicity. For example, tolerability can include the degree to which toxicity can be tolerated.

In some embodiments, the toxicity is membrane toxicity. As used herein, and in its conventional sense, "membrane toxicity" refers to the ability of a toxicity-induced change to occur to the cell membrane. Such changes to the cell membrane can include, but are not limited to, a change in the normal flux of ions, a change related to cell membrane fluidity, a change related to ion channels in the cell membrane, and the like. In some embodiments, the biophysical effect is tolerability. In some embodiments, the tolerability is one or more of: an effect that inhibits the normal flux of ions and an effect that inhibits membrane fluidity. In some embodiments, the tolerability is the effect that inhibits the normal flux of ions. In some embodiments, the tolerability comprises an effect that inhibits membrane fluidity. In some embodiments, a biophysical effect comprises a membrane fusion and fission event. In some embodiments, the membrane fusion and fission event result in loss of cellular signaling activity.

In some embodiments, membrane toxicity or membrane tolerability is measured by dysregulation of neuronal depolarization. Neuronal depolarization includes, but is not limited to, pre-synaptic, post-synaptic, and channel-related action potentials. In some embodiments, membrane toxicity comprises one or more of: pre-synaptic, post-synaptic, and channel-related action potential dysregulations by the oligonucleotide. In some embodiments, membrane toxicity includes, but is not limited to, depolarization by OBMs, such as pre-synaptic, post-synaptic, channel relation action potential dysregulations by OBMs in electrically excitable cells. In some embodiments, electrically excitable cells include, but are not limited to, neurons, muscle cells, such as skeletal, and cardiac cells. In some embodiments, membrane toxicity or tolerability includes, but is not limited to, membrane potential events. In some embodiments, membrane potential events can occur in electrically excitable cells. In some embodiments, membrane toxicity or tolerability comprises membrane potential dysregulation in the kidneys. In some embodiments, membrane toxicity or tolerability comprises membrane potential dysregulation in hepatocytes.

In some embodiments, toxicity comprises cytotoxicity. In some embodiments, cytotoxicity is measured by an apoptotic response in a cell. In some embodiments, cytotoxicity comprises metabolic toxicity. In some embodiments, cytotoxicity comprises cell organelle toxicity, for example in systemic and neuronal tissues. In some embodiments, cytotoxicity comprises receptor-specific toxicity, for example, in systemic and neuronal tissues. In some embodiments, cytotoxicity comprises mitochondrial toxicity. In some embodiments, cytotoxicity comprises cell-surface receptor-mediated toxicity. In some embodiments, cytotoxicity is measured by mis-localization, accumulation, granules/paraspeckles associated with toxicity. In some embodiments, the cytotoxicity is one or more selected from a liver toxicity measured, for example, an amount of ALT, an amount of AST, or a ratio of ALT to AST; a kidney toxicity measured by, for example, an amount of blood urea nitrogen (BUN), creatine, or a ratio of BUN to creatine; and a neurotoxicity measured by microglia activation, for example, gene expression, neuronal cell loss, or histology, and a combination thereof. Cytotoxicity can be measured using any conventional method known in the art.

In some embodiments, the biophysical effect is one or more pharmacological endpoints. Pharmacological endpoints comprise tissue distribution and productive uptake (ADME, subcellular localization, etc.), targetability of RNA (accessibility, (co-)transcriptional dynamics of RNA, etc.), hybridization, specificity and enzymatic rules (edit tolerance and sequence preference). In some embodiments, pharmacological endpoints comprise cytotoxicity including hepato, renal, cardio and neurotoxicity. In some embodiments, pharmacological endpoints comprise immunogenicity and/or immunostimulatory effects. In some embodiments, pharmacological endpoints comprise membrane toxicity, including acute neurotoxicity and cardiotoxicity. In some embodiments, neurotoxicity is acute or delayed neurotoxicity.

In some embodiments, cytotoxicity can be measured by measuring a level of apoptosis, necroptosis, pyroptosis, viability, necrosis, caspase activity, and/or annexin exposure, in a cell. In some embodiments, the biophysical effect is determined by cell viability and cell death assays. Cell viability and cell death assays, any of which can be used with the provided methods. Cell viability assays included, but are not limited to, Alamar Blue (measures metabolic activity of cell by reducing resazurin to resorufin), MTT (MTT is reduced to formazan), MT (MT substrate is reduced in a viable cell which then binds with the NanoLuc luciferase to generate a signal), MitoView (measures cell viability by its ability to accumulate in active mitochondria), Cell-Titer-Fluor Cell Viability Assay (a Gly-Phe-AFC peptide that enters the cells and is cleaved to produce the fluorescent AFC), and Calcein AM (non-fluorescent membrane permeable compound; cytoplasmic esterases convert to green fluorescence retained in cells with intact plasma membrane). Cell death assays include, but are not limited to various caspase assays, Annexin V (which measures phosphatidylserine exposure on outer cell membranes during apoptosis in a calcium dependent manner), CellTox (cyanine dye excluded from viable cells but binds DNA of dead cells, enhancing the fluorescent properties), Propidium Iodide (membrane impermeant nucleic acid intercalator used to stain dead cells, and 7-AAD (7-aminoactinomycin D which is a membrane impermeant fluorescent DNA binding dye commonly used for FACS).

In some embodiments, cytotoxicity can be determined using various dye-based assays to assess real-time cell viability and apoptosis/necrosis onset. In some embodiments, assays include, but are not limited to RealTime-Glo MT Viability Assay, CellEvent Caspase-3-7 Assay, Real-Time-Glo Annexin V Apoptosis and Necrosis assay and combinations thereof.

In some embodiments, cytotoxicity can be determined using Next Generation Sequencing (NGS) assays. In some embodiments, NGS assays include but are not limited to DGE (digital gene expression), RNA-Seq, L1000, RASI-seq, DRUG-seq, QuantSeq 3' mRNA-Seq, and combinations thereof.

In some embodiments, the biophysical effect is a measure of body weight. In some embodiments, the biophysical effect is a measure of temperature. In some embodiments, the biophysical effect is a measure of one or more enzymes in a tissue (e.g., liver, kidney, spleen, muscle, heart, etc.). In some embodiments, the biophysical effect is a measure of one or more enzymes in the liver, such as, but not limited to: ALT, AST, ALPI, GGT, LDI, SDH, 5-nucleotidase, AST/ALT, GLDH, TBI, AMM, and TP. In some embodiments, the biophysical effect is a measure of one or more enzymes in blood. In some embodiments, the biophysical effect is a measure of one or more measurements selected from alanine transaminase (ALT), aspartate aminotransferase (AST), blood urea nitrogen (BUN), creatinine, C-Reactive Protein (CRP) and total bilirubin (TBILI). In some embodiments, the biophysical effect is a hepatotoxicity measurement, including a measurement of serum ALT, AST, and creatine. In some embodiments, the biophysical effect is nephrotoxicity measurement including a measurement of urinary KIM-1 and Serum Cystatin-c (CysC). In some embodiments, the biophysical effect is a measurement of GLDH. In some embodiments, the biophysical effect is a measurement of CCK-18. In some embodiments, the biophysical effect includes measurements of liver function. Non-limiting examples of liver function markers include ALT, AST, alkaline phosphatase (ALPI), Gamma(γ)-Glutamyl Transferase (GGT), Lactate Dehydrogenase (LDI), Sorbitol dehydrogenase (SDH), 5-nucleotidase, AST/ALT, Glutamate Dehydrogenase (GLDH), Total Bilirubin (TBI), Ammonia (AMM), Total Protein (TP), Albumin (ALB), Globulin (GLOB), Albumin: Globulin (A/G), Prothrombin Time (PT), Activated partial Thromboplastin Time (APIT), Lactate (LA), and Bile Acid (BA). In some embodiments, the biophysical effect includes measurements of kidney function. Non-limiting examples of kidney function markers include Cystatin-C, Kim-1, BUN, and Urinary CREA, etc.

In some embodiments, the biophysical effect is a measurement of calcium flux.

In some embodiments, the biophysical effect is a measurement of a dosing concentration. In some embodiments, the biophysical effect is a dosing concentration. In some embodiments, the biophysical effect is a dosing concentration. In some embodiments, the biophysical effect is a cytotoxic dosing concentration. In some embodiments, the biophysical effect is a non-toxic dosing concentration. In some embodiments, the biophysical effect is a dose response (e.g., tissue toxicity, such as liver or kidney toxicity). In some embodiments, the biophysical effect is a maximum tolerable (e.g., maximum non-toxic) dose concentration. In some embodiments, the biophysical effect is a minimum efficacious dose concentration. In some embodiments, the biophysical effect is a maximum efficacious dose concentration. In some embodiments, the biophysical effect is an effect of calcium flux on dosing concentration.

In some embodiments, the toxicity is immunotoxicity. In some embodiments, the immunotoxicity includes a measurement of one or more of cytokine measurements, complete blood count (CBC) measurements, and CRP measurements.

In some embodiments, the biophysical effect is an immunostimulatory and/or immunogenic modulation. In some embodiments, an immunostimulatory effect is measured by an immune response. In some embodiments, the immunostimulatory modulation is an increase in an immune response. In some embodiments, an immunostimulatory modulation is a decrease in an immune response. In some embodiments, the immune response is sequence dependent. In some embodiments, the immune response is chemistry dependent. In some embodiments, the immune response is sequence and chemistry dependent. In some embodiments, the immune response includes cytokine stimulation and/or release. In some embodiments, an immune response is determined by cytokine stimulation and/or release. In some embodiments, an immune response is determined by platelet effects. In some embodiments, an immune response is determined by macrophage activation. In some embodiments, macrophage activation is in response to innate nonself and/or danger signals that are patient-specific. In some embodiments, an immune response is determined by microglial activation in the brain. In some embodiments, an immune response is determined by activation of resident macrophages, such as, but not limited to liver Kupffer cells, lung macrophages, and the like. In some embodiments, an immunostimulatory effect or immunogenic effect is determined by adaptive immune system related effects. In some embodiments, immunostimulatory modulation and/or immunogenic modulation is determined by one or more of immune system related effects, stimulating the effect of anti-drug antibodies, and triggering anti-drug antibody inflammatory signaling. In some embodiments, the biophysical effect is an immune-mediated response. In some embodiments, the biophysical effect is an increase in immune-mediated response. In some embodiments, a biophysical effect is a reduction of immune-mediated inflammation.

In some embodiments, the biophysical effect is a measure of absorption, distribution, metabolism, or excretion of the oligonucleotide. In some embodiments, the biophysical effect is a measure of absorption, distribution, metabolism, or excretion of the oligonucleotide in one or more of: a tissue, cell, intracellular space, and extracellular space. The intracellular space can include any intracellular fluid within the cell. In some embodiments, the extracellular space includes any extracellular fluidic between the cells. In some embodiments, the intracellular fluid includes, but is not limited to, blood or cerebrospinal fluid. In some embodiments, the extracellular fluid includes, but is not limited to, interstitial fluid, plasma, lymph, cerebrospinal fluid, and milk. In some embodiments, the biophysical effect is a measure of pharmacokinetics or pharmacodynamics, and comprises one or more of: substrate-target processing, dynamics, accessibility, inter-cellular distribution, intra-cellular distribution, and time-dependent availability.

In some embodiments, the biophysical effect is absorption. In some embodiments, absorption is determined by the amount of cellular uptake and accumulation of oligonucleotides generally into cells. In some embodiments, absorption is determined by the amount of cellular uptake and accumulation into a desired cellular compartment, such as membrane bound (e.g. nucleus, cytoplasm, mitochondria) and non-membrane bound organelles (e.g., ribosomes, P-bodies, paraspeckles, nucleoli, stress granules). In some embodiments, absorption is determined by optimization of the time it takes for an oligonucleotide to absorb into tissue beds, cells, or eventual subcellular localization.

In some embodiments, the biophysical effect is distribution. In some embodiments, the distribution is determined by the transportation of the oligonucleotide from the site of dosing to cells, tissues, or other structures either selectively or generally. In some embodiments, the site of dosing includes the site of delivery of the oligonucleotide. In some embodiments, the oligonucleotide is administered by, for example, oral delivery, systemic delivery, intravenous delivery, or intrathecal injection. In some embodiments, the oligonucleotide is delivered via local administration, such as, but not limited to aerosol exposure, topical or dermal ointments, or tumor injections, to cells, tissues or other structures either selectively or generally. In some embodiments, distribution is determined by binding to and subsequent release from proteins or cells that facilitate transportation of oligonucleotides from one place in the organism to another (e.g. binding to a protein or cell that transits OBMs from the blood to the CSF).

In some embodiments, the biophysical effect is a $C_{max}$ measurement. $C_{max}$ is the highest concentration of a drug, agent, or molecule (e.g., oligonucleotide) in the blood, plasma, cerebrospinal fluid, or target organ after a dose is given. In some embodiments, the biophysical effect is a $C_{min}$ measurement. $C_{min}$ is the lowest concentration of a drug, agent, or molecule (e.g., oligonucleotide) in the blood, plasma, cerebrospinal fluid, or target organ after a dose is given. In some embodiments, the biophysical effect is a $t_{max}$ measurement, which is the time it takes to reach $C_{max}$. In some embodiments, the biophysical effect is a $t_{min}$ measurement, which is the time it takes to reach $C_{min}$. In some embodiments, the biophysical effect is an Area Under the Curve (AUC) measurement. The AUC is a measure of the exposure of the drug, agent or molecule (e.g., oligonucleotide). In some embodiments, the biophysical effect is a $t_{1/2}$ (elimination half-life) measurement, to the time taken for half the initial dose of medicine administered to be eliminated from the body. In some embodiments, the biophysical effect is selected from one or more of a $C_{max}$ measurement, a $C_{min}$ measurement, a $t_{max}$ measurement, a $t_{min}$ measurement, an AUC measurement, and a $t_{1/2}$ measurement.

$t½$ (elimination half-life)±is the time taken for the plasma concentration to fall by half its original value.

In some embodiments, the biophysical effect is metabolism. In some embodiments, metabolism is controlled by the stability of the oligonucleotide (e.g. as a whole, in partial form, or in a specific confirmation). Non-limiting examples include, but are not limited to: controlling of how long an oligonucleotide persists in the cell, blood, CSF or other biofluid; targeting moieties, such as aptamers, may be optimized to degrade at a differential rate, or at a different time, or place than the oligonucleotide; oligonucleotide conformational changes may be desired and facilitated by differential metabolism of the oligonucleotide that would activate the oligonucleotide by exposing/releasing an active substructure, or separate oligonucleotide; and control of what metabolites are produce. In some embodiments, controlling what breakdown products are created by the oligonucleotide enhances the safety of the oligonucleotide.

In some embodiments, the biophysical effect is excretion. In some embodiments, excretion is determined by controlling how either whole or metabolites of the source oligonucleotides are removed from the organism. In some embodiments, the biophysical effect of excretion is optimized to enhance bile or urine removal.

In some embodiments, the biophysical effect is a biological activity of the oligonucleotide (e.g., functionality). Accordingly, it should be noted that in some embodiments, the terms "biological activity" and "biophysical functionality" can refer to a type of biophysical effect described herein. In some embodiments, the biophysical effect is selectivity of the oligonucleotide to the target. In some embodiments, the biophysical effect is inactivity of the oligonucleotide. In some embodiments, the biophysical effect is lack of selectivity to the target.

In some embodiments, the biological activity comprises an off-target engagement of the oligonucleotide to a target molecule. As used herein and in its conventional sense, "off-target", refers to a lack of selectivity to a target, which, for example, causes an oligonucleotide to effect a non-target molecule (e.g. non-target gene). In some cases, the non-target molecule is a non-target gene. In some cases, lack of selectivity to a target is caused by the same on-target mechanism for on-target engagement (e.g., RNase H1-mediated mechanism, and the like). In some cases, lack of selectivity to a target is caused by a different mechanism than the intended on-target mechanism for on-target engagement. In some embodiments, the off-target engagement causes the oligonucleotide to perform an effective amount of one or more of: non-target gene expression knock-down, non-target RNA splicing modulatory behavior, non-target gene expression upregulation, non-target gene-editing, non-target RNA-editing, non-target protein specific targeting, non-target receptor specific targeting, non-target enzymatic substrate specific targeting, non-target distribution and uptake into tissues or cells, and non-target interaction with a specific protein or receptor. In some embodiments, off-target engagement is measured by transcriptome-wide gene expression readouts. In some embodiments, off-target engagement of the oligonucleotide to the target is measured by unintended splicing modulation readouts transcriptome-wide. In some embodiments, off-target engagement is measured by biophysical readouts of sequence/edit tolerance of relevant enzymes RNaseH, Ago2 spliceosome factors, and the like.

In some embodiments, the biological activity comprises an on-target engagement of the oligonucleotide to a target molecule. In some embodiments, the on-target engagement causes the oligonucleotide to perform an effective amount of one or more of: gene expression knock-down, RNA splicing modulatory behavior, gene expression upregulation, gene-editing, RNA-editing, interaction with a specific protein or receptor, protein specific targeting, receptor specific targeting, enzymatic substrate specific targeting, and distribution and uptake into tissues or cells.

In some embodiments, the on-target engagement comprises an amount (e.g. %) of gene expression knock-down. In some embodiments, gene expression knock-down can be measured using conventional methods known in the art. In some embodiments, gene expression knock-down is measured by RNase H1 dependent RNA cleavage. In some embodiments, gene expression knock-down is measured by RNA-Induced Silencing Complex (RISC)-dependent RNA cleavage. In some embodiments, the biophysical effect is RNase H-mediated degradation in the nuclease.

In some embodiments, the on-target engagement comprises an amount of splicing modulatory behavior. RNA mis-splicing causes a large array of human diseases due to hereditary and somatic mutations. In some embodiments, the biophysical effect comprises recognition of specific RNA splicing regulatory elements to modulate splicing. In some embodiments, the biophysical effect is the amount of splicing modulatory behavior that drives preferential expression of an alternative splice isoform. In some embodiments, the biophysical effect is the amount of splicing modulatory behavior that drives preferential co-transcriptional induction of nonsense-mediated decay.

In some embodiments, the on-target engagement comprises the amount (e.g. %) of gene expression up-regulation. In some embodiments, on-target engagement is the amount of gene expression upregulation determined by stabilization of RNA through reduction of endogenous RNA degradation pathways, such as, but not limited to, miRNA directed RISC cleavage, protracted maintenance of polyA tails, and stabilization of RNA structures, including polysome formation. In some embodiments, on-target engagement is the amount of gene expression upregulation determined by enhanced translation through blockage of non-productive uORFs. In some embodiments, on-target engagement is the amount of gene expression upregulation determined by OBM-directed recruitment of nuclear factors. In some embodiments, OBM directed recruitment of nuclear factors is determined by directly binding DNA. In some embodiments, OBM directed recruitment of nuclear factors is determined by indirectly binding DNA through interactions that orchestrate productive chromatin organization or dynamics.

In some embodiments, on-target engagement comprises an amount of gene-editing. In some embodiments, gene-editing is achieved by CRISPR (Clustered Regularly Interspaced Short Palindromic Repeats)/Cas and CRISPR-like enzymatic processes. In some embodiments, gene editing is achieved by engagement with other endogenous DNA repair and editing mechanisms, such as, but not limited to, zinc-finger nucleases (ZFNs) and transcription activator-like effector nucleases (TALENs). Using a guide RNA, Cas endonuclease (e.g., Cas9) can modify (e.g. cleave) double-stranded DNA at any site, defined by the guide RNA sequence, and including a protospacer-adjacent (PAM) motif. A Cas/guide RNA complex (i.e., a Cas targeting complex) constitutes a simple and versatile RNA-directed system for modifying target DNA, or modifying proteins associated with target DNA, in any desired cell or organism. Additionally, a Cas targeting complex having a mutated Cas9 protein with reduced or removed nuclease activity can still bind to target DNA.

In some embodiments, the biophysical effect is an amount of RNA-editing achieved. In some embodiments, the amount of RNA-editing is determined by engagement with adenosine deaminase acting on RNA (ADAR) or other RNA editing enzyme systems conventionally known in the art.

In some embodiments, the biophysical effect is interaction with a specific protein or receptor. In some embodiments, the biophysical effect is one or more of: protein specific targeting, receptor specific targeting, or enzymatic substrate specific targeting.

In some embodiments, the biophysical effect is one or more nucleotide sequence and/or chemical modifications/mutations configured to improve its biophysical function. In some embodiments, the biophysical effect is 2 or more, 3 or more, 4 or more, 5 or more, 6 or more, 7 or more, 8 or more, 9 or more, or 10 or more nucleotide sequence or chemical mutations configured to improve its biophysical function. In some embodiments, the biophysical effect is 1 to 3 mutations, 3 to 5 mutations, 5 to 10 mutations, 10 to 15 mutations, 15 to 20 mutations, 20 to 25 mutations, or 25 to 30 mutations.

In some embodiments the biophysical effect is one or more chemical modifications. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. In some embodiments, the chemical modification to the oligonucleotide is a modified backbone or no natural internucleoside linkages. In some embodiments, the modification can include modified backbones of the oligonucleotide that include, among others, those that do not have a phosphorus atom in the backbone. In some embodiments, the modification includes those that do not have a phosphorus atom in their internucleoside backbone. In some embodiments, the modification can include one that will have a phosphorus atom in its oligonucleotide backbone. In some embodiments, the modification can include phosphorothioate (PS) internucleoside linkages.

Modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included.

Examples of chemical modifications include phosphorothioate groups, 2'-deoxynucleotide, 2'-OCH.sub.3-containing ribonucleotides, 2'-F-ribonucleotides, 2'-methoxyethyl ribonucleotides, combinations thereof and the like.

In some embodiments, the chemical modification is a PM-based oligonucleotide modification where the five-membered ribose heterocycle is replaced by a six-membered morpholine ring.

In some embodiments, the biophysical effect is the efficacy of aptamers. In some embodiments, the efficacy of aptamers is measured by the binding activity to a target molecule (e.g. OBM). In some embodiments, the efficacy of the aptamer is measured by, for example, non-specific (e.g. intra and inter-) tissue-specific distribution and/or uptake; non-specific cellular-specific distribution and/or uptake, and/or non-specific cell organelle-specific distribution and/or uptake. In some embodiments, the efficacy of the aptamer is measured by binding affinity to miRNAs, ncRNAs/regulatory RNAs, and the like. In some embodiments, the efficacy of the aptamer is measured by the aptamer tertiary structure interaction with a target molecule (e.g. OBM). In some embodiments, the biophysical property of the aptamer comprises the amount of cellular uptake and trafficking of the aptamer. In some embodiments, the biophysical effect of the aptamer comprises OBM-aptamer interactions. In some embodiments, the biophysical effect of the aptamer comprises the folded structures of the aptamer. In some embodiments, the folded structures are secondary and/or tertiary structures. In some embodiments, the folded structure comprises one or more of a bulge, an apical loop, a stem-loop, a 3-way junction, a form helix, an internal loop, a pseudoknot, a hairpin, G-quadruplexes, and a combination thereof.

In some embodiments, the biophysical effect of the aptamer is the electrostatic interactions of the aptamer. In some embodiments, the biophysical effect of the aptamer is the hybridization energetics and biophysics of the aptamer.

In some embodiments, the biophysical effect is one or more of: cellular uptake and trafficking of the aptamer, binding affinity to the OBM, OBM-aptamer interactions, folded (e.g. secondary, tertiary) structures of the aptamer, electrostatic interactions, and hybridization energetics and biophysics.

In some embodiments, the biophysical effect is selected to be optimal for an individual based on the individual's genetics.

II.C. Characteristics of Biophysical Function

Aspects of the present method include generating a final set of oligonucleotides using a refined machine-learned model as described herein. In some embodiments, generating the final set of oligonucleotides using the refined machine-learned model comprises: receiving an identification of a biophysical function to be performed by an oligonucleotide-based medicine (OBM) and an identification of a measure of the biophysical effect; identifying a set of characteristics of an oligonucleotide associated with the biophysical function; and generating, using the refined machine-learned model, a set of oligonucleotides having one or more of the identified set of characteristics and corresponding to the measure of the biophysical effect.

In some embodiments, the biophysical function is the desired function of an OBM that satisfies a requirement of the biophysical effect (e.g. of measure of the biophysical effect). For instance, the biophysical function can be selected by an OBM designer, who can also specify a parameter (such as a threshold toxicity) that any oligonucleotide produced by the machine-learned models described herein should satisfy (e.g., in the threshold toxicity example, any oligonucleotides provided by the machine-learned model should corresponding to a toxicity less than the specified threshold toxicity).

In some embodiments, the biophysical function comprises a reduction of immune-mediated inflammation. In some embodiments, the biophysical function comprises an increase in immune-mediated responses.

In some embodiments, the biophysical function is an on-target engagement of the oligonucleotide to a target. In some embodiments, the on-target engagement causes the oligonucleotide to perform an effective amount of one or more of: gene expression knock-down, RNA splicing modulatory behavior, gene expression upregulation, gene-editing, RNA-editing, protein specific targeting, receptor specific targeting, enzymatic substrate specific targeting, and distribution and uptake into tissues or cells.

In some embodiments, the target is a gene product. In some embodiments, the gene product is one or more of: an mRNA, a splicing site on a pre-mRNA, a truncated transcript, an aborted transcription product, or an antisense transcript. In some embodiments, the gene product is a divergent antisense transcript. In some embodiments, the gene product is a convergent antisense transcript.

In some embodiments, the biophysical function is a toxicity threshold (e.g. cytotoxicity, immunotoxicity, membrane toxicity, nephrotoxicity, hepatotoxicity, etc.) that is lower than a reference toxicity threshold.

In some embodiments, the biophysical function is an increase in site-specific modification of the target molecule.

In some embodiments, the biophysical function is the targeting of a gene associated with a genetic disease (e.g. common or rare genetic disease).

III. Training Protocol

There are two foundational barriers preventing the rapid creation of new OBMs that can be affordably engineered and provided to patients with the understanding that they will be safe and effective. Currently, there are no methods that can adequately predict the pharmacology of newly designed OBMs. This forces drug developers to rely on onerous screening processes (e.g. screening 1000s of oligonucleotides for a single target) which are slow, expensive, and are often toxic and inactive. Secondly, OBMs have limited capacity to reach several cell-types, tissues and organ systems.

The training model described in the present disclosure increases the probability of safe (e.g. non-toxic) and effective (e.g. active, favorable binding to target, etc.) OBMs, and reduces the number of toxic and inactive OBMs for preclinical testing, thereby reducing the cost of data generation.

Aspects of the present methods include initializing a machine-learned model configured to map an oligonucleotide sequence to a probability of a biophysical effect using an initial oligonucleotide corresponding to the biophysical effect; generating a first set of oligonucleotides based on the initial oligonucleotide using the initialized machine-learned model; determining, for each oligonucleotide of the first set of oligonucleotides, whether the oligonucleotide corresponds to the biophysical effect; generating a refined machine-learned model using the first set of oligonucleotides and whether each of the first set of oligonucleotides corresponds to the biophysical effect; and generating a final set of oligonucleotides using the refined machine-learned model.

In some embodiments, the first set of oligonucleotides comprises 50 or fewer oligonucleotides, between 50 and 100 oligonucleotides, between 100 and 150 oligonucleotides, between 150 and 200 oligonucleotides, between 200 and 300 oligonucleotides, between 300 and 400 oligonucleotides, between 400 and 500 oligonucleotides, between 500 and 750 oligonucleotides, between 750 and 1000 oligonucleotides, between 1000 and 1500 oligonucleotides, between 1500 and 2000 oligonucleotides, between 2000 and 2500 oligonucleotides, between 2500 to 5000 oligonucleotides, or between 5000 to 10000 oligonucleotides.

In some embodiments, the machine-learned model is a probabilistic graphical model. In some embodiments, the initial machine-learned model can be represented by a sequence graph. In some embodiments, the sequence graph has flexible diversity of overlapping monomers at each position of the oligonucleotide sequence, and probabilistic factors quantifying sequence dependence of the biophysical effect, such as a pharmacological, biological, or chemical effect.

The methods of the present disclosure include initializing a machine-learned model configured to map an oligonucleotide sequence to a probability of a pharmacological effect using an initial oligonucleotide corresponding to the pharmacological effect. In some embodiments, the initial oligonucleotide is a random seed oligonucleotide or a known oligonucleotide with a known biophysical effect. The initial oligonucleotide can be selected, for instance by an entity associated with the creation and training of the machine-learned model, based on a biophysical effect intended to be associated with the machine-learned model. For example, if a machine-learned model configured to predict a toxicity of an oligonucleotide is desired, then an initial oligonucleotide known or determined to have a high toxicity can be selected for use in initializing the machine-learned model. Alternatively, if a machine-learned model configured to predict a low toxicity of an oligonucleotide is desired, then an initial oligonucleotide known or determined to have a low toxicity can be selected for use in initializing the machine-learned mode.

In some embodiments, initializing the machine-learned model comprises initializing a set of coefficients each representative of a correlation between n-grams of an oligonucleotide sequence and a presence of the biophysical effect. In some embodiments, at least one coefficient of the set of coefficients is representative of a correlation between consecutive n-grams within the oligonucleotide and the presence of the biophysical effect.

In some embodiments, the machine-learned model comprises one of: an Ising model, a Potts model, a hidden Markov model, a continuous random field model, and a directed acyclic graphical model.

In some embodiments, the machine-learned model comprises one of: a random forest classifier, a logistic regression, a linear regression, a neural network, a sparsity-driven convex optimization fit, and a support vector machine.

In some embodiments, characteristics of the machined-learned model include constraints and factors. In some embodiments, the factors are indicative of a correlation between consecutive graphical nodes or consecutive n-grams of an oligonucleotide sequence and a measure of the biophysical effect for which the machine-learned model is being trained. In some embodiments, the machine-learned model includes a set of coefficients representative of the factors. In some embodiments, the coefficients are updated during refinement of the machine-learned model (e.g., when the model is being refit/retrained) based on in vivo, in vitro, in silico, or in situ assays, or combinations thereof.

In some embodiments, the method comprises generating a first set of oligonucleotides using the initialized machine-learned model. For example, an initial or native first iteration of the model is generated based on the initial oligonucleotide (e.g. test oligonucleotide, non-random seed oligonucleotide, random seed oligonucleotide), and the first set of oligonucleotides are generated in part based on outputs of the initialized machine-learned model.

In some embodiments, the first set of oligonucleotides comprise n-gram mutations of the initial oligonucleotide. In some embodiments, the first set of oligonucleotides comprise gapped n-grams. In some embodiments, each of the first set of oligonucleotides comprises a single or double n-gram or gapped n-gram mutation of the initial oligonucleotide. In some embodiments, the first set of oligonucleotides comprise a subset of all single or double n-gram or gapped n-gram mutations of the initial oligonucleotide.

In some embodiments, the first set of oligonucleotides, when fitted by the initialized machine-learned model, represent a range of probabilities of the biophysical effect as determined by the initialized machine-learned model. For instance, the first set of oligonucleotides can include one or more nucleotides corresponding to probabilities of having the biophysical effect within one or more of the following probability ranges: 0 to 10%, 10 to 20%, 20 to 30%, 30 to 40%, 40 to 50%, 50 to 60%, 60 to 70%, 70 to 80%, 80 to 90%, and 90 to 100%. Likewise, the first set of oligonucleotides can include one or more nucleotides corresponding to probabilities within one or more of the following probability ranges: 0 to 25%, 25 to 50%, 50 to 75%, 75 to 100%, about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%. In some embodiments, the first set of oligonucleotides can include approximately equal numbers of oligonucleotides likely to correspond to the biophysical effect and unlikely to correspond to the biophysical effect (e.g., the average of the probabilities of each oligonucleotide corresponding to the biophysical effect is approximately 50%+/−15%). It should be noted that the discussion herein of selecting oligonucleotides from a larger set of oligonucleotides based on the probabilities determined by the machine-learned model and whether the probabilities fall into the probability ranges applies equally to sets of the oligonucleotides other than the first set of oligonucleotides, and applies equally to versions of the machine-learned model being trained other than the initialized machine-learned model. For example, a subset of possible, optimized oligonucleotides are selected for testing in vivo and in vitro for purposes of reducing cost and time for in vivo and/or in vivo testing for all possible oligonucleotide targets. The subset of optimal oligonucleotides generated by the machine-learned model of the methods described herein enable highly cost- and time-efficient exploration of OBMs for therapeutic use.

The methods of the present disclosure include determining, for each oligonucleotide of the first set of oligonucleotides, whether the oligonucleotide corresponds to the biophysical effect. In some embodiments, determining whether an oligonucleotide corresponds to the biophysical effect comprises performing one or more of: in vitro, in vivo, ex vivo, and in situ assays on the oligonucleotide. In some embodiments, determining whether an oligonucleotide corresponds to the biophysical effect comprises performing in vitro assays. In some embodiments, determining whether an oligonucleotide corresponds to the biophysical effect comprises performing in vivo assays. In some embodiments, determining whether an oligonucleotide corresponds to the biophysical effect comprises performing in situ assays. In some embodiments, the in vivo and/or in vitro assays include, but are not limited to, liver toxicity assays, membrane toxicity assays, metabolic toxicity assays, and immunotoxicity assays using conventional methods as known in the art. In some embodiments, the in vivo assay is an alanine transaminase (ALT) levels measured in rodent blood samples. In some embodiments, the method comprises performing in vivo and/or in vitro assays to measure protein expression.

In vitro assays to determine whether a protein has an RNA-binding portion interacts with a subject guide RNA (e.g. oligonucleotide) can be any convenient binding assay that tests for binding between a protein and a nucleic acid. Exemplary binding assays will be known to one of ordinary skill in the art and can be found for example in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945; all of which are hereby incorporated by reference in their entirety. In some embodiments, assays include, but are not limited to, binding assays (e.g., gel shift assays) that include adding a guide RNA and a Cas9 protein to a target nucleic acid.

Assays to determine whether a protein has an activity portion (e.g., to determine if the polypeptide has nuclease activity that cleave a target nucleic acid) can be any convenient nucleic acid cleavage assay that tests for nucleic acid cleavage. Exemplary cleavage assays can be found in U.S. patent applications: 20140068797, 20140189896, 20140179006, 20140170753, 20140179770, 20140186958, 20140186919, 20140186843; international applications: WO2013176772, WO2013141680, WO2013142578, WO2014065596, WO2014089290, WO2014099744, WO2014099750, WO2014104878, WO2014093718, WO2014093622, WO2014093655, WO2014093701, WO2014093712, WO2014093635, WO2014093595, WO2014093694, and WO2014093661; and U.S. Pat. Nos. 8,697,359, 8,771,945. In some embodiments, assays can include, but are not limited to, cleavage assays that include adding a guide RNA (e.g. oligonucleotide) and a Cas9 protein to a target nucleic acid. In some cases, a PAM-mer is also added (e.g., in some cases when the target nucleic acid is a single stranded nucleic acid).

In some embodiments, in vivo assays are performed on, for example, non-human mammals, mammals, rodents, rats, mice, humans, e.g. rats, mice, pigs, cows, goats, sheep, non-human primates, fish, frogs, vertebrates, and the like.

In some embodiments, the in vitro assays include, but are not limited to, Caspase activation, In some embodiments, the in vitro assays can be performed in, for example, eukaryotic single-cell organism, a somatic cell, a germ cell, a stem cell, a plant cell, an algal cell, an animal cell, an invertebrate cell, a vertebrate cell, a fish cell, a frog cell, a bird cell, a mammalian cell, a pig cell, a cow cell, a goat cell, a sheep cell, a rodent cell, a rat cell, a mouse cell, a non-human primate cell, or a human cell.

In some embodiments, the in vivo and/or in vitro assays measure the "efficiency" of non-homologous end joining (NHEJ) and/or homology directed repair (HDR) after administration of the oligonucleotide, which can be calculated by any convenient method. For example, in some cases, efficiency can be expressed in terms of percentage of successful HDR. For example, a restriction digest assay (e.g., using a restriction enzyme such as HindIII) can be used to generate cleavage products and the ratio of products to substrate can be used to calculate the percentage. For example, a restriction enzyme can be used that directly cleaves DNA containing a newly integrated restriction sequence as the result of successful HDR. More cleaved substrate indicates a greater percent HDR (a greater efficiency of HDR). As an illustrative example, a fraction (percentage) of HDR can be calculated using the following equation [(cleavage products)/(substrate plus cleavage products)] (e.g., $b+c/a+b+c$), where "a" is the band intensity of DNA substrate and "b" and "c" are the cleavage products.

In some cases, efficiency can be expressed in terms of percentage of successful NHEJ. For example, a T7 endonuclease I assay can be used to generate cleavage products and the ratio of products to substrate can be used to calculate the percentage NHEJ. T7 endonuclease I cleaves mismatched heteroduplex DNA which arises from hybridization of wild-type and mutant DNA strands (NHEJ generates small random insertions or deletions (indels) at the site of the original break). More cleavage indicates a greater percent NHEJ (a greater efficiency of NHEJ). As an illustrative example, a fraction (percentage) of NHEJ can be calculated using the following equation: $(1-(1-(b+c/a+b+c))^{1/2}) \times 100$, where "a" is the band intensity of DNA substrate and "b" and "c" are the cleavage products (see e.g., Ran et. al., Cell. 2013 Sep. 12; 154(6):1380-9). This formula is used (instead of the formula used for HDR, see above) because upon re-annealing, one duplex of mutant DNA can produce two duplexes of mutant:wild-type hybrid, doubling the actual NHEJ frequency.

In some embodiments, determining whether an oligonucleotide corresponds to the biophysical effect comprises simulating, in silico, one or more of: in vitro, in vivo, ex vivo, and in situ assays on the oligonucleotide. For instance, a synthetic or machine-learned model can be trained to predict a measure or characteristic of the biophysical effect based on a sequence or other properties of the oligonucleotide. These models can be trained on training data that includes associations between oligonucleotides and the biophysical effect corresponding to the models.

The present methods include generating a refined machine-learned model using the first set of oligonucleotides and whether each of the first set of oligonucleotides corresponds to the biophysical effect. In some embodiments, generating a refined machine-learned model comprises retraining and/or refitting the machine-learned model based on a determination of whether an oligonucleotide corresponds to the biophysical effect using, for example, actual (e.g. in vivo, in vitro, and/or in situ assay results) or simulated test results.

In some embodiments, generating the refined machine-learned model comprises retraining the initialized machine-learned model using the first set of oligonucleotides and whether each of the first set of oligonucleotides corresponds to the biophysical effect. As used herein, "retraining" a machine-learned model can include modifying coefficients or other parameters of the machine-learned model using real-world measures of the biophysical effect of the first set of oligonucleotides such that the machine-learned model is able to better predict a correlation between a sequence of an oligonucleotide and the biophysical effect.

In some embodiments, generating the refined machine-learned model comprises performing a sparsity-constrained fit on the first set of oligonucleotides and whether each of the first set of oligonucleotides corresponds to the biophysical effect.

In some embodiments, generating the refined machine-learned model comprises generating a new machine-learned model using the first set of oligonucleotides and whether each of the first set of oligonucleotides corresponds to the biophysical effect.

In some embodiments, generating the refined machine-learned model comprises: generating a first updated machine-learned model using the first set of oligonucleotides and whether each of the first set of oligonucleotides corresponds to the biophysical effect; generating a second set of oligonucleotides based on the first updated machine-learned model, each of the second set of oligonucleotides comprising a mutation of the initial oligonucleotide; determining, for each oligonucleotide of the second set of oligonucleotides, whether the oligonucleotide corresponds to the biophysical effect; and generating a second updated machine-learned model using the second set of oligonucleotides and whether each of the second set of oligonucleotides corresponds to the biophysical effect. In some embodiments, generating the second updated machine-learned model comprises retraining the first updated machine-learned model using the second set of oligonucleotides and whether each of the second set of oligonucleotides corresponds to the biophysical effect. In some embodiments, generating the second updated machine-learned model comprises performing a sparsity-constrained fit on the second set of oligonucleotides and whether each of the second set of oligonucleotides corresponds to the biophysical effect. In some embodiments, generating the second updated machine-learned model comprises generating a new machine-learned model using the second set of oligonucleotides and whether each of the second set of oligonucleotides corresponds to the biophysical effect.

In some embodiments, the second set of oligonucleotides comprises 50 or fewer oligonucleotides, between 50 and 100 oligonucleotides, between 100 and 150 oligonucleotides, between 150 and 200 oligonucleotides, between 200 and 300 oligonucleotides, between 300 and 400 oligonucleotides, between 400 and 500 oligonucleotides, between 500 and 750 oligonucleotides, between 750 and 1000 oligonucleotides, between 1000 and 1500 oligonucleotides, between 1500 and 2000 oligonucleotides, between 2000 and 2500 oligonucleotides, between 2500 to 5000 oligonucleotides, or between 5000 to 10000 oligonucleotides. It should be noted that additional sets of oligonucleotides can be generated over multiple iterations using increasingly complex mutations of the initial oligonucleotide (or mutations of earlier sets of oligonucleotides) for use in updating/retraining the machine-learned model in order to improve the performance of the machine-learned model. In some embodiments, this process is iteratively performed until a stop condition is satisfied.

In some embodiments, generating the refined machine-learned model further comprises: generating a third set of oligonucleotides, each of the third set of oligonucleotides comprising a generated oligonucleotide; determining, for each oligonucleotide of the third set of oligonucleotides, whether the oligonucleotide corresponds to the biophysical effect; and modifying the second updated machine-learned model using the third set of oligonucleotides and whether each of the third set of oligonucleotides corresponds to the biophysical effect. In some embodiments, the third set of oligonucleotides further comprises approximately equal portions of oligonucleotides predicted to correspond to the biophysical effect and predicted to not correspond to the biophysical effect by the second updated machine-learned model. In some embodiments, generating the third updated machine-learned model comprises retraining the second updated machine-learned model using the third set of oligonucleotides and whether each of the third set of oligonucleotides corresponds to the biophysical effect. In some embodiments, generating the third updated machine-learned model comprises performing a sparsity-constrained fit on the third set of oligonucleotides and whether each of the second set of oligonucleotides corresponds to the biophysical effect. In some embodiments, generating the third updated machine-learned model comprises generating a new machine-learned model using the third set of oligonucleotides and whether each of the second set of oligonucleotides corresponds to the biophysical effect. It should be noted that additional sets of oligonucleotides can be generated randomly or non-randomly for use in iteratively updating/retraining the machine-learned model in order to improve performance of the machine-learned model. In some embodiments, this process is iteratively performed until a stop condition is satisfied. In some embodiments, the third set of oligonucleotides are randomly or non-randomly generated.

In some embodiments, a third set of oligonucleotides comprises 50 or fewer oligonucleotides, between 50 and 100 oligonucleotides, between 100 and 150 oligonucleotides, between 150 and 200 oligonucleotides, between 200 and 300 oligonucleotides, between 300 and 400 oligonucleotides, between 400 and 500 oligonucleotides, between 500 and 750 oligonucleotides, between 750 and 1000 oligonucleotides, between 1000 and 1500 oligonucleotides, between 1500 and 2000 oligonucleotides, between 2000 and 2500 oligonucleotides, between 2500 to 5000 oligonucleotides, or between 5000 to 10000 oligonucleotides.

In some embodiments, generating an oligonucleotide in the second set of oligonucleotides or the third set of oligonucleotides comprises: identifying an n-gram of an oligonucleotide sequence that strongly corresponds to the biophysical effect; and generating an oligonucleotide comprising a mutation of the identified n-gram of the oligonucleotide sequence. In some embodiments, an n-gram is a single n-gram. In some embodiments, an n-gram is a double n-gram. In some embodiments, an n-gram is a gapped n-gram. In some embodiments, an n-gram comprises one or more n-grams. In some embodiments, an n-gram comprises a collection of n-grams.

As noted above, in some embodiments, generating a refined machine-learned model further comprises iteratively refining the machine-learned model using additional sets of oligonucleotides until a stop condition is satisfied. In some embodiments, the stop condition comprises one or more of: a number of iterations, a threshold predictive performance of the machine-learned model, and a below-threshold increase in predictive performance of the machine-learned model after a refining iteration. In some embodiments, the stop condition comprises a number of iterations. In some embodiments, the stop condition comprises a threshold predictive performance of the machine-learned model.

In some embodiments, the stop condition comprises a below-threshold increase in predictive performance of the machine-learned model after a refining iteration. In some embodiments, the number of refining iterations ranges from 1 to 3, 3 to 5, 5 to 10, 10 to 15, 15 to 20, 20 to 30, 30 to 40, 40 to 50, 50 to 60, 60 to 70, 70 to 80, 80 to 90, or 90 to 100. In some embodiments, the number of refining iterations is more than 100. In some embodiments, the number of iterations is 1 iteration, 2 iterations, 3 iterations, 4 iterations, 5 iterations, 6 iterations, 7 iterations, 8 iterations, 9 iterations, 10 iterations, 11 iterations, 12 iterations, 13 iterations, 14 iterations, or 15 iterations.

In some embodiments, generating a "refined" machine-learned model comprises one or more of: updating parameters of the existing machine-learned model or model architecture; updating drop parameters by sparsity, elastic net, dropoff or other model penalizations; and updating the machine-learned model architecture, including updating the feature space of the model entirely. In some embodiments, updating the feature space of the model entirely is performed by changing how variates are encoded in features or how connections between features are modeled.

In some embodiments, generating the final set of oligonucleotides using the refined machine-learned model comprises: receiving an identification of a biophysical function to be performed by an oligonucleotide-based medicine (OBM) and an identification of a measure of a tolerable biophysical effect; identifying a set of characteristics of an oligonucleotide associated with the biophysical function; and generating, using the refined machine-learned model, a set of oligonucleotides having one or more of the identified set of characteristics and corresponding to the measure of the biophysical effect.

In some embodiments, the final set of oligonucleotides comprises a set of aptamers. In some embodiments, the final set of oligonucleotides comprises a set of oligonucleotide-aptamer conjugates. In some embodiments, the final set of oligonucleotides comprises a set antisense oligonucleotides (ASO). In some embodiments, the final set of oligonucleotides comprises a set of anti-gene oligonucleotides. In some embodiments, the final set of oligonucleotides comprises a set CpG oligonucleotides. In some embodiments, the final set of oligonucleotides comprises a set single-guide RNAs. In some embodiments, the final set of oligonucleotides comprises a set dual-guide RNAs. In some embodiments, the final set of oligonucleotides comprises a set targeter RNAs. In some embodiments, the final set of oligonucleotides comprises a set activator RNAs.

In some embodiments, the final set of oligonucleotides comprise a set of oligonucleotides with an optimized dosing profile that is deemed efficacious, safe, and non-toxic. The dosing for a particular oligonucleotide can be determined using the models described herein, which can be configured to determine a relationship between a particular dose of an oligonucleotide and a measure of a corresponding biophysical effect. The model can apply such a model to a desired measure of a biophysical effect in order to predict a dose of a particular oligonucleotide that can produce the measure of the biophysical effect. In some embodiments, the final set of oligonucleotides comprises a set of steric-blocking oligonucleotides.

In some embodiments, the final set of oligonucleotides comprises a set of ASOs to modulate RNase H activity.

In some embodiments, the final set of oligonucleotides comprises a set of tracr RNAs.

In some embodiments, the final set of oligonucleotides comprises a set of RNA interference (RNAi)-based oligonucleotides.

In some embodiments, the final set of oligonucleotides comprises a set of RNA (ADAR)-guiding RNA (AD-gRNAs).

In some embodiments, the final set of oligonucleotides comprises a set of double stranded RNA (dsRNA).

In some embodiments, the final set of oligonucleotides comprises a set of CRISPR RNA (crRNA).

In some embodiments, retraining, refining, or changing the machine-learned model as described herein is performed by a controller. In some embodiments, the controller is a feedback controller. In some embodiments, the feedback controller retrains and/or changes the machine-learned model based on the first set of oligonucleotides, a second set of oligonucleotides, and/or a third set of oligonucleotides having one or more of the identified set of characteristics and corresponding to the measure of the biophysical effect. In some embodiments, the controller generates mapping paths in a sequence graph. In some embodiments, the controller generates the first set of oligonucleotides. In some embodiments, the controller generates the second set of oligonucleotides. In some embodiments, the controller generates the third set of oligonucleotides.

In some embodiments, the method comprises calibrating noise in model readout to quantify the level of accuracy achievable in learning factors and stopping criteria of the methods described herein.

In some embodiments, the method comprises providing experimental or synthetic results (e.g. from in vivo and/or in vitro testing) into the feedback controller.

In some embodiments, the controller updates the machine-learned model and quantifies (e.g. a subset of all possible) probabilistic factors using a sparsity-driven convex optimization algorithm. In some embodiments, the controller updates the initial sequence graph, for example, by updating the monomer diversity at each position and/or abandoning certain factors and/or introducing new factors, to optimize new paths within the sequence graph to explore which paths are expected to improve learning/balancing the data-set during the next iteration of model retraining or updating.

In some embodiments, the controller updates the machine-learned model to generate OBMs from all possible paths from a specific type of perturbations. In some embodiments, the controller retrains the machine-learned model to select a fraction of all possible such designs to test in the next batch, primarily by balancing the predicted odds of expected pharmacology and deciding the optimal policy to query highly informative factors that are under-investigated. In some embodiments, the controller that retrains the machine-learned model identifies which set of oligonucleotide sequences to test in the next iteration of oligonucleotide sequential experimental design or the next iteration of machine-learned model retraining or updating. In some embodiments, the controller retrains the machine-learned model to design OBMs by mapping paths in the graph expected to optimize learning the probabilistic factors of the model, iterating over custom steps of designing and testing batches of OBM sequences. In some embodiments, the controller receives feedback control in the form of the results of the current and all previous batches of experiments, in turn determining the next set of paths to explore in the graph, and translating the paths to oligonucleotide sequences to test experimentally. In some embodiments, the feedback control refines the machine-learned model in every step or iteration. In some embodiments, the controller that trains the machine-learned model enriches for sequences of desirable pharmacology, balancing the dataset and avoiding creating data with many more data points of undesirable pharmacology (e.g. toxic) than desirable pharmacology (e.g. safe). In some embodiments, the controller controls and adapts the sequence and factor graph, the monomer diversity in each of the positions, and/or the probabilistic factors of an oligonucleotide sequence.

Aspects of the present disclosure include a method for generating oligonucleotide-based medicines, comprising: initializing a probabilistic machine-learned model configured to map an oligonucleotide sequence to a probability of a biophysical effect using an initial oligonucleotide corresponding to the biophysical effect; generating a first set of oligonucleotides by performing single or double n-gram mutations on the initial oligonucleotide to obtain oligonucleotides mapped to a distributed range of probabilities by the initialized probabilistic machine-learned model; determining, for each oligonucleotide of the first set of oligonucleotides, a first measure of correlation between the oligonucleotide and the biophysical effect based on real-world experimental determination; generating a first refined probabilistic machine-learned model based on the first set of oligonucleotides and the determined first measures of correlation; generating a second set of oligonucleotides, each of the second set of oligonucleotides generated and mapped to a distributed range of probabilities by the first refined probabilistic machine-learned model; determining, for each oligonucleotide of the second set of oligonucleotides, a second measure of correlation between the oligonucleotide and the biophysical effect based on real-world experimental determination; generating a second refined probabilistic machine-learned model based on the second set of oligonucleotides and the determined second measures of correlation; and generating a final set of oligonucleotides using the second refined probabilistic machine-learned model. In some embodiments, each of the second set of oligonucleotides are randomly or non-randomly generated.

In some embodiments, the method further comprises receiving a set of biophysical requirements for an oligonucleotide-based medicine from a designer; and selecting a subset of the generated final set of oligonucleotides that satisfy the set of biophysical requirements.

In some embodiments, the first set of oligonucleotides comprises 50 or fewer oligonucleotides, between 50 and 100 oligonucleotides, between 100 and 150 oligonucleotides, between 150 and 200 oligonucleotides, between 200 and 300 oligonucleotides, between 300 and 400 oligonucleotides, between 400 and 500 oligonucleotides, between 500 and 750 oligonucleotides, between 750 and 1000 oligonucleotides, between 1000 and 1500 oligonucleotides, between 1500 and 2000 oligonucleotides, between 2000 and 2500 oligonucleotides, between 2500 to 5000 oligonucleotides, or between 5000 to 10000 oligonucleotides.

Aspects of the present disclosure include a method for generating oligonucleotide-based medicines, comprising: initializing a probabilistic machine-learned model configured to map an oligonucleotide sequence to a probability of a biophysical effect using an initial oligonucleotide corresponding to the biophysical effect; generating a first refined probabilistic machine-learned model by, until a first stop condition is satisfied, iteratively 1) generating an increasingly complex set of oligonucleotide mutations based on the initial oligonucleotide, 2) determining a real-world measure of correlation between the set of oligonucleotide mutations and the biophysical effect, and 3) fitting the set of oligonucleotides and the determined real-world measures of correlations to an increasingly refined probabilistic machine-learned model; generating a second refined probabilistic machine-learned model by, until a second stop condition is satisfied, iteratively 1) generating a random set of oligonucleotides, 2) selecting a subset of the generated random set of oligonucleotides such that approximately equal portions of the subset of the generated random set of oligonucleotides are predicted to correspond to the biophysical effect and are predicted not to correspond to the biophysical effect, 3) determining a real-world measure of correlation between the subset of oligonucleotides and the biophysical effect, and 4) fitting the subset of oligonucleotides and the determined real-world measures of correlations to an increasingly refined probabilistic machine-learned model; and generating a final set of oligonucleotides using the second refined probabilistic machine-learned model.

IV. Examples

IV.A. Example 1—Training Protocol of OBMs

For the sake of clarity, the methods described herein are now described in the context of a particular example. It should be noted, however, that the subject matter described herein is applicable far more broadly. This example is constructed for the case of cytotoxicity for a narrow class of OBMs: all possible 16 nucleotide long ASOs with fixed 3-10-3 LNA gapmer chemical scaffold. In the traditional approach, a number of random sequences, or sequences targeting a number of genes, will be designed and tested, for instance in in vitro assays and rodent liver toxicity assays. The total number of possible ASOs in this case is $4^{16} \sim 4.3 \times 10^9$, because each position in the ASO can be one of the four nucleotides, [A;C;G;T].

In the traditional approach, with a budget of testing 1000 ASOs, one would have typically created a data-set of 100 safe ASOs and 900 toxic ASOs, assuming the odds of safety is 1:10.

The traditional approach of screening produces many fewer examples of the type of OBMs of interest for machine learning and designing, i.e., safe OBMs. The present methods provide for enriching safe ASOs to ~50% to create a data-set of ~500 safe ASOs. Moreover, the designed ASOs query the sequence dependence of the ASOs pharmacology in a far more rigorous manner.

Step 1: Creating Sequence Graph

In this illustrative example, consider monomeric units to be dimers, defined by $x_i^a$ at position i along the ASO, chosen from the word space [AA;AC; : : : ;GT;TT] indexed by a. The probability model P(y|X), i.e. where y is the cytotoxicity measurement and X represents the sequence, is shown in equation 1. This is the sequence-to-pharmacology mapping described herein.

$$P(y|X) = \prod_k \prod_l \Phi_k(x_i^a, x_j^b) \Theta_l(x_i^a, x_j^b)$$

Figure 2:
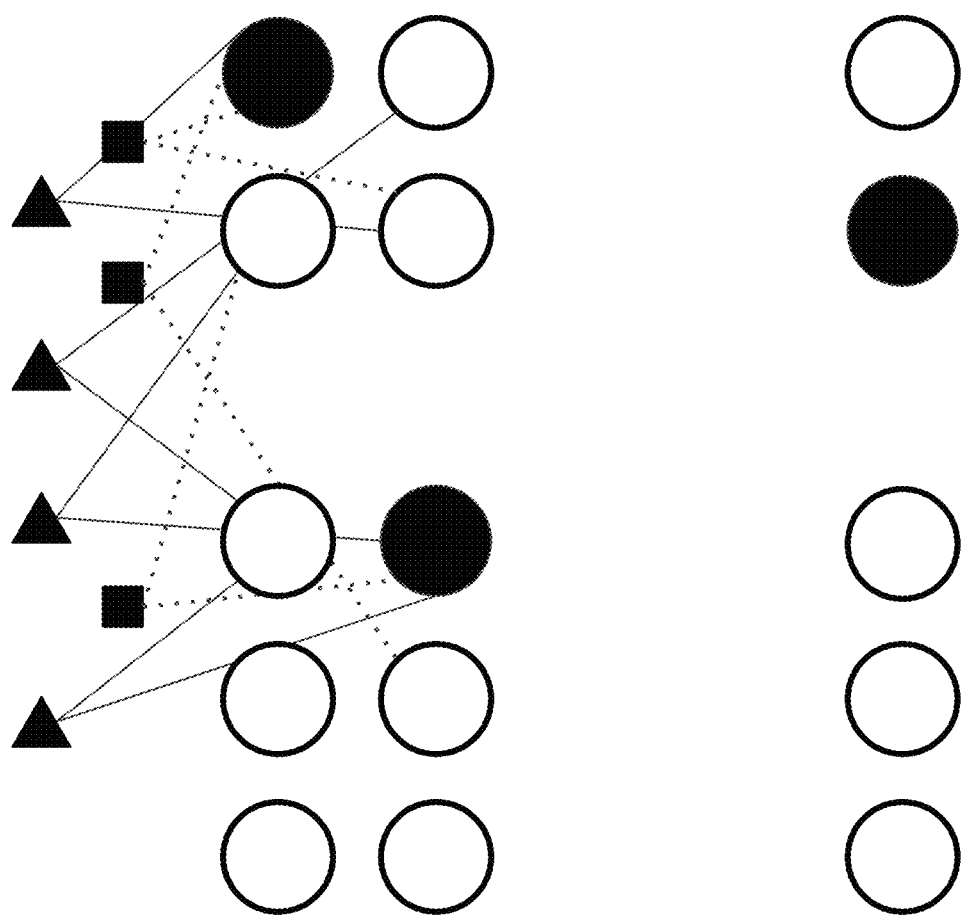
FIG. 2 shows the factor graph representation of FIG. 1, called sequence graph. The black and white nodes were described in FIG. 1. The boxes (and corresponding dashed lines) are the factors corresponding to the constraints on which monomer at a position can be composed with which monomer at the next position. The triangles (and corresponding solid lines) are the factors capturing both independent and correlated components of the contribution of the monomers to the probability distribution of outcome.
Figure 3:
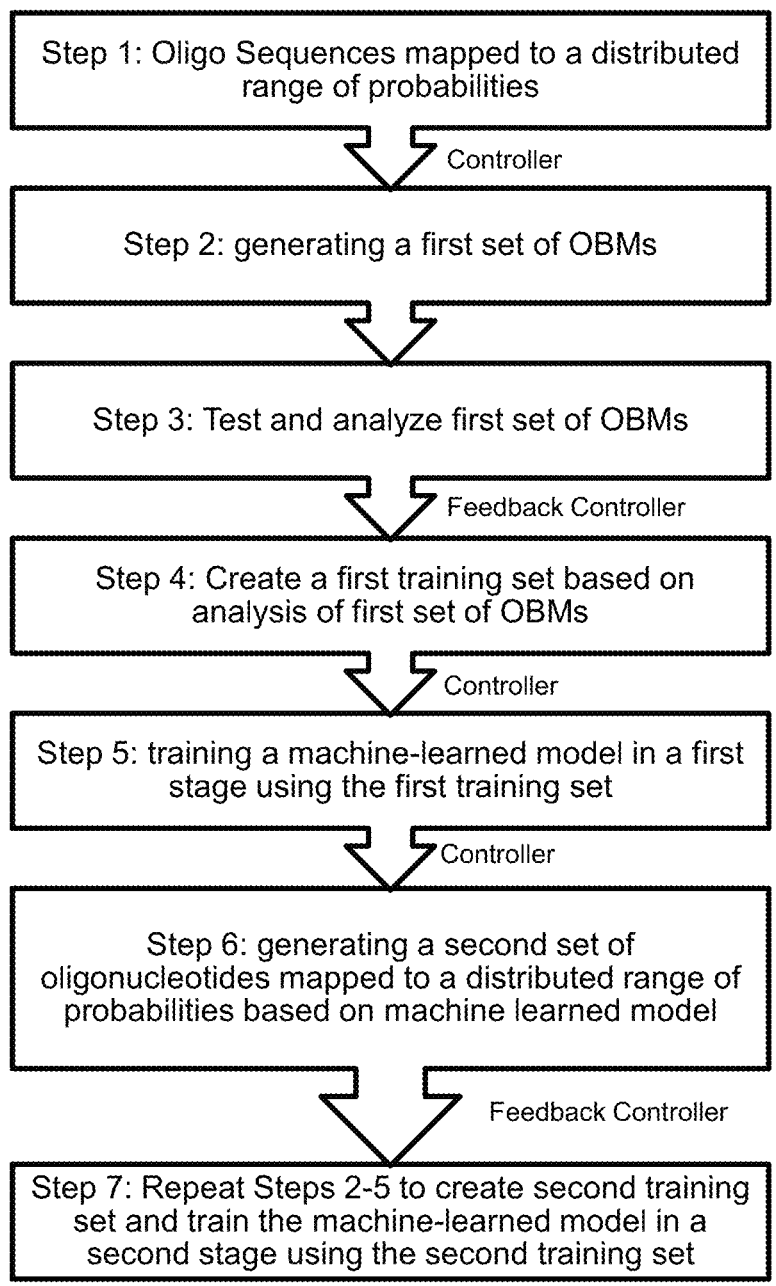
FIG. 3 depicts a process of generating one or more OBMs using machine learning, according to various embodiments.

In this example, a sequence graph is created, see FIG. 1 and a corresponding factor graph, see FIG. 2, only including pairwise factors between monomer nodes limiting monomer interactions modeled to be simply pairwise. Therefore, the θ terms enforce constraints on composition of monomers to create the ASO polymer, and the Φ terms are factors for joint probability distributions capturing correlations. In this example, there are 16 possible nodes in each column of the graph of FIG. 1 and FIG. 2, corresponding to the dimer word space. Therefore, Φ is defined on the space of 16*16*15=3840 dimensions corresponding to the constraints of which monomeric word can be linked which monomeric word in the next position along the ASO. These constraints are known by construction, and not learned from data.

A probability function, being positive, can be written as an exponential function. In the example of dimer units, and as it turns out in a wide variety of examples, the variables $x_i^a$ will be indicators, denoted by $\sigma_i^a$, presence/absence of the dimer a at position i. The notation from x to s is changed to make the binary status explicit. Therefore, without loss of generality, $$\Phi(\sigma_i^a, \sigma_j^b) \sim \exp(\mu_i^a \sigma_i^a + \mu_j^b \sigma_j^b + J_{ij}^{ab} \sigma_i^a \sigma_j^b + \ldots)$$

where μ are the first order weights and J are the second-order interactions, and the dots represent even higher order interactions. If the pairwise interactions are limited to nearest neighbors, only 3840 factors $\Phi(\sigma_i^a, \sigma_j^b)$ may be required to train the machine-learned model.

Step 2: Create Controller

The controller is initiated by the sequence graph and factors described above, including prior beliefs or biophysical effects on the factors from existing quantitative or qualitative knowledge.

Step 3: Create First Set of OBMs to Test

In this example, the controller is set up to efficiently consider paths in the sequence graph—these paths are optimal small perturbations of the path corresponding to an ASO whose cyto-toxicity has already been measured. The paths considered are optimal in exploration of poorly characterized factors and exploitation of important factors of high-confidence. The controller weights all the factors and uncertainties for each such path and generates the first batch of ASOs to test.

Step 4: Test First Batch

The first batch will typically have low sequence diversity in tested sequences, and therefore, are maximally informative in characterizing the noise, calibrating the dynamic range and precision of measurements. In this example, the measurements may be in vitro assays like Caspase activation and in vivo assays like alanine transaminase (ALT) level in rodent blood samples.

Step 5: Feedback Control

The results of the experiments are used to update factors using sparsity constrained fitting paradigms. In this example, without any loss of generality, the regression problem of mapping sequence X to measurement M(X) is defined as:

$$M(X) = \frac{1}{1 + \exp(E(X))}$$

where E(X) is an "energy" function. The function E(X) is approximated as follows:

$$E(X) = \sum_i \sum_a \mu_i^a \sigma_i^a + \sum_{i>j} \sum_{ab} J_{ij}^{ab} \sigma_i^a \sigma_j^b$$

where a,b spans the word space, for example, for DNA dimers over [AA;AC; : : : ;GT;TT]. The μ parameter captures the independent weights of monomers for every position in the ASO, and the $J_{ij}^{ab}$ parameter captures correlative weights. The N sequences tested in the first batch are denoted as $S_0$. Every sequence is encoded in the matrix $\theta_n$, where $\theta_n$ is an indicator (binary) matrix of shape P*(L−k+1). Here P is the size of the word space, L is the length of the polymer, and k is length of k-mers, here k=2. The shape of matrix μ is identical. Unraveling $\theta_n$ and concatenating N is used to create the sequence code matrix θ, of shape N*(P*(L−k+1)). The parameter vector is unraveled to a vector of length P*(L−k+1)). In this matrix language, the linear equation to solve in order to fit the data and update the factors, θ·μ=Y.

In this example, the goal is to solve the quadratic programming problem:

$$\min_\mu \|Y - \Theta \cdot \mu\|_2 + \lambda |\mu|_1$$

where $\| \ldots \|_2$ is l2-norm is l1-norm $| \ldots |_1$ and λ is a sparsity parameter, a hyper-parameter in this context that the controller can tune. The λ-term ensures robust learning and Occam's razor in model complexity. A very similar formalism applies for fitting J parameters.

Step 6: Generate New Batch of OBMs to Test

In this example, the controller generates a new batch of ASOs to test, weighing small perturbations (mutations in dimers) in the sequence graph and computes optimal paths that balance the explore-vs-exploit trade-off in learning the mapping of sequence-to-pharmacology. The controller also predicts the expected measurement and appropriately chooses the batch of ASOs to test such that the measurements are balanced, i.e., approximately equal numbers of safe and toxic compounds are expected to be seen. These predictions are made using the sparse models described above.

Step 7: Test New Batch of OBMs

In this example, the ASOs cyto-toxicity is measured, and the measurement noise model is re-calibrated.

Step 8: Feedback Loop and Sequence Graph Updating and Resource Reallocation

Several iterations for Steps 5-7 are performed, with later iterations updating the sequence graph by measuring the non-redundancy and relevance using mutual information of monomer interactions captured in the sequence graph against measurement distributions, and expanding the monomer diversity (at specific positions along the ASO) of high information content by considering, for example, trimers and tetramers. For any factor $\Phi$, relevance is defined as, $I(\Phi|y)$, where I is mutual information and y is the measurement. For any two factors, $\Phi_1$ and $\Phi_2$, non-redundancy is defined as $I(\Phi_1, \Phi_2|y) - I(\Phi_1, \Phi_2)$.

The updated sequence graph also dictates resource reallocation in which factors to learn extensively in the next series of feedback control loops, and which ones have already been learned well and whether the net learning of sequence-pharmacology mapping has saturated.

In this illustrative example, using only dimers as nodes of the sequence graph, using a synthetic cyto-toxicity generator as described below, it is shown that that the method balances the data by enriching for safe ASOs within a few batches of ASOs tested (50 tested in each batch) and learns to predict measurements well within a few steps. In this simulated example, for simplicity, the sequence graph is not updated by adjusting word space diversity in specific positions adapting to information content as described above—the controller is simpler than the ideal scenario, and yet performs well.

The Synthetic Cytotoxicity Generator

For the illustrative example, a simulated response is trained to be realistic and designed to be exigent on the policy evaluations. This is done by creating protein-binding events in sequences, where many protein binding events may all independently and to varying degree cause a toxicity measurement response. The synthetic cyto-toxicity generator is a function that takes in a sequence as input and produces a response between [0,1] as output, where 1 is the most desirable response (such as, "very safe") and 0 is the least desirable response, such as "very toxic." In some embodiments, the synthetic cyto-toxicity generator is a machine-learned model trained on oligonucleotide sequences and associated measures of cyto-toxicity. It should be noted that biophysical effects can be determined using machine-learned models (such as the synthetic cyto-toxicity generator), each trained on oligonucleotide sequences and corresponding measures or characteristics of the biophysical effect. Likewise, these machine-learned models are configured to compute or predict a measure or characteristic of a biophysical effect for sequences of oligonucleotides being evaluated.

Algorithmic Steps in Simulation:

The simulator uses real ENCODE position-weight matrices (PWMs) of motifs for DNA-binding proteins.

Randomly, of the order of W=100 motifs are chosen. Each is assigned a random uniform probability pm of being picked in the next step, and a random weight $r_w$, where $w \in [1, W]$. There is also the option of a random choice of where to embed the motif in the sequence, in the next step, typically the motif will be localized in the sequences by position, say, between positions 3-7.

The PWMs of the motif w are embedded in the background frequency of nucleotides to create a position dependent emission probability of each nucleotide a at each position i, denoted by $P_i^a(w)$ for a Hidden-Markov Model (HMM). Because the sequences that are considered short, for example, 16-mer sequences, only one motif is embedded in one sequence-note that ENCODE motif lengths are 7- to 20-mers. The probability of picking the HMM with the motif w is $p_w$. A dataset of N sequences is created in this manner.

Response generation: Now that these sequences are created, the next step is to quantify whether the sequence will be bound by the putative protein. Even random sequences will exhibit motifs with a low probability because motifs are intrinsically probabilistic descriptions of binding events. Also, PWMs may be weak (low in information) or strong (high in information) and have a range of lengths. To quantify the p-value of whether a sequence will be bound by the putative protein, the distribution of binding was computed for random sequences of the same length as the motif. This is done by computing the cross-correlation of the PWM against $10^5$ randomly generated sequences and recording the mean $m_w$ and standard deviation $\sigma_w$ of the random samples. The p-value for any sequence binding is then the probability of observing a value (as extreme or more) of then cross-correlation of the PWM and the one-hot encoded sequence. One hot-encoding is a binary matrix, 4*L for a sequence of length L and indicator for [A;C;G;T] in each row.

Mathematically, given one-hot encoding of a sequence, Sa and PWM Pa for a motif of length l, cross-correlation is, $$C_j(w) = \sum_a \sum_{i=1}^{L-l} P_i^a(w) S_{i+j}^a$$

The value $C_j(w)$ is next assigned a "True/False" value if it exceeds the p-value cutoff for the motif or not, referred to as indicator vector $I_j^w(s)$ for motif w and sequence s.

The previous step quantifies whether a motif is bound, for any sequence. In this step the binding events are assigned the weights for the protein contribution, $r_w$ defined above. The response for sequence is, $$R(s) = \frac{1}{1 + \exp\left[\sum_j \sum_w r_w I_j^w(s)\right]}$$

Figure 4:
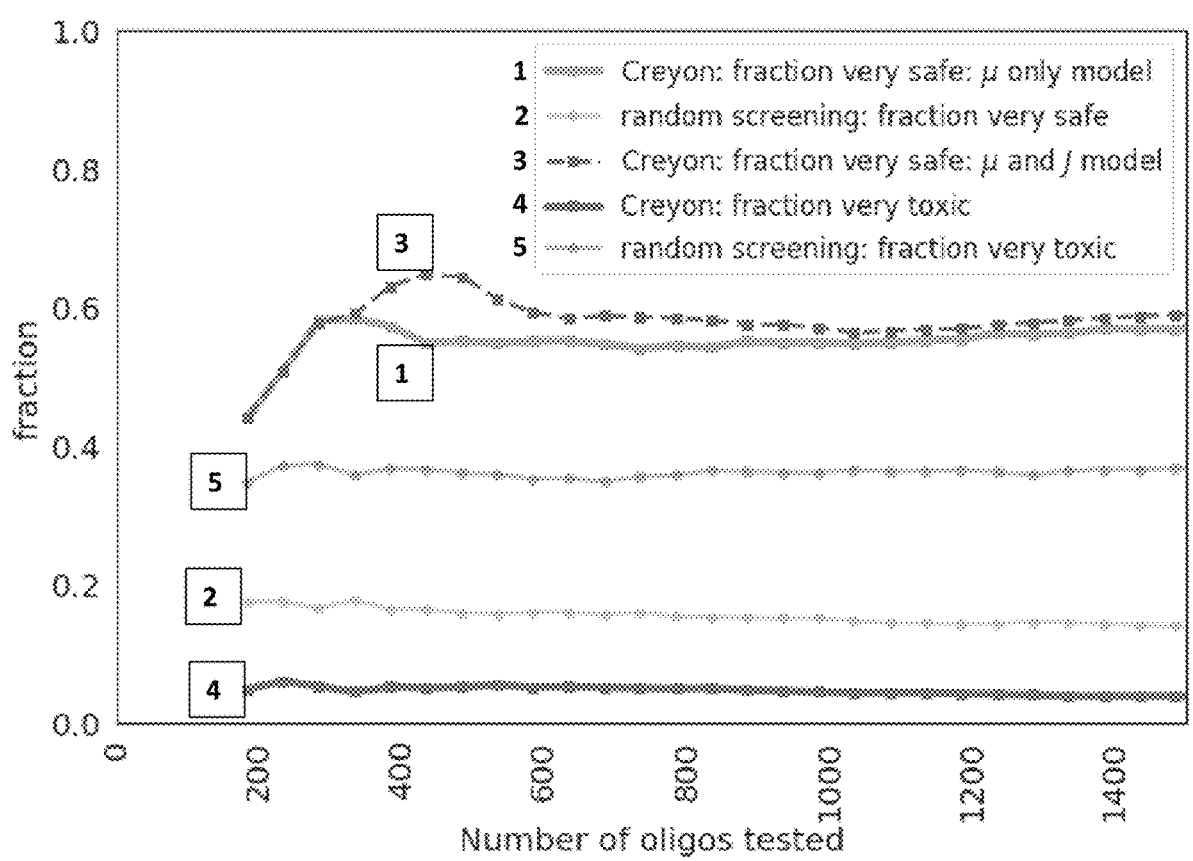
FIG. 4 depicts a balanced data set of ASOs generated according to the processes described herein, relative to a traditional approach of generated ASOs. In particular, using a non-adaptive sequence graph and a demanding scenario created by a cytotoxicity simulator for which ~100 random (realistic ENCODE PWMs) protein-binding events all independently can lead to cyto-toxicity, the processes described herein can create balanced data-sets by learning to predict measurements. In the traditional approach, screening 1000 ASOs may produce roughly 100 'safe' ASOs, while the processes described herein can produce more than 600 'safe' ASOs. It should be noted that in this example, 'safe' ASOs are enriched by several fold within the first few feedback loop steps of the processes described herein (such that every dot is a step).

Using the experiment generator, an illustrative simple policy is evaluated, and performance is shown in FIG. 4.

IV.B. Example 2—Aptamers for Targeting Tissues and Cells (CAT-TAC)

Aspects of the present disclosure related to using oligonucleotide-based medicines stem from their limited activity in several tissues and cell types. The example described herein solves this by leveraging recent advances in the fields related to aptamer screening & optimization, in conjunction with the machine learning and pharmacology modelling paradigm of oligonucleotides described herein, called CAT-TAC (Creyon Aptamers for Targeting Tissues and Cells).

The example provided herein show a scalable platform for computational engineering of aptamers as conjugates to OBMs, and thereby dramatically enhancing OBMs' tissue/ cell-type specific delivery. Aptamers share the merits of synthesis-simplicity and the compositional, biophysical and medicinal/computational chemistry properties as the models provided herein for OBMs.

The advanced oligonucleotide-based medicine (OBM) platform described is applied to the creation and selection of novel aptamers, which are short highly structured DNA/RNA fragments (chemically modified nucleic acid polymers) that enhance the general pharmacology of OBMs, and targets OBMs to specific tissues, cells, and/or intracellular/extracellular spaces.

Aspects of the present disclosure describe building datasets, algorithms and tools to accurately predict the pharmacology of OBMs (payload) conjugated to aptamers, called aptamer-OBMs. The payload compounds are typically short (15-22 nt) and, typically by design, have minimal capacity to form self-structures, as opposed to aptamers. The pharmacophore, or the properties of the aptamer-OBMs which drive their pharmacokinetic properties, and the dianophore, or the properties of the aptamer-OBMs which determine the molecular targeting efficacy, are largely separable, with the pharmacophore being primarily defined by the molecular processes involved in the OBM:target-RNA duplex formation, the systems biology of the target and the biophysical rules of enzymatic mechanism-of-action (RISC/Ago, RNAseH1, etc.). The dianophore, on the other hand, is largely controlled through protein:OBM interactions. Leveraging this separability, tools developed by the present inventors focused on creating datasets and models optimal in uncovering the sequence-chemistry to pharmacology mapping of all non-branched polymeric nucleic acids at a pace and cost which is order(s) of magnitudes better than the tradition trial-and-error approach.

Specifically, aspects of the present disclosure describe (a) search and active learning algorithms, chemical space autoencoders and experimental protocols/methods to productively and intelligently navigate the very high-dimensional sequence/chemistry space of aptamers-OBMs (b) created datasets in batches of aptamer-OBMs tested such that every batch is near-optimal for machine learning OBM pharmacology (c) balanced the outcome of pharmacology experiments and datasets created sequentially in a feedback control paradigm by enriching for aptamer-OBMs with rare pharmacology (which is typically the desired pharmacology i.e. safe & efficacious).

The methods described herein leverage the mathematical and physical properties inherent in polymeric interactions of OBMs-self-interactions are typically sparse & pairwise, while non-self interactions are typically dictated by protein-binding domains and/or hybridization dynamics. Aptamers on the other hand have dense secondary self-interactions, however, tertiary conformation interactions (e.g. pseudoknots, kissing-hairpins, hairpin bulge etc.) are typically sparse. The mathematical and algorithmic innovation as described in aspects of the present disclosure on short OBMs, the search and design policies in active learning and feedback control, generalize well to the unique sparsities present in aptameric interactions. The optimal controllers described herein enable highly cost- and time-efficient exploration of aptamer sequence/chemistry-to-pharmacology mappings.

The design algorithms described herein use high-throughput readouts of in vitro or in vivo structural constraints such as those measured by SHAPE-Seq (Selective 2'-Hydroxyl Acylation Analyzed by Primer Extension Sequencing) like methods to refine and augment topological and structural classifications of aptamers. Such readouts are important in the rather common context of chemically modified nucleotides for which current in silico methods for folding are expected to be misleading or fail completely because they were parameterized using native DNA or RNA hybridization datasets. Several well-developed NGS-based highly-multiplexed measurements on RNA structure can be utilized to greatly constrain the possible 3D-conformations of the aptamers-OBMs.

In silico methods for folding short RNA/ssDNA sequences are still rather limited in recapitulating the diversity of energetically-equivalent structures and low-energy conformations explored by aptamers in vivo. In order to ensure that the search algorithms of the present methods perform as expected in the presence of novel chemistries, the method requires (a) creating data analysis algorithms to model SHAPE-seq like readouts and establish the constraints these readouts impose on topology and 3D structural properties of OBMs (b) performing extensive simulations to mimic the complexity novel chemistry adds to the problem, by creating synthetic hybridization energetics for folding algorithms and recreating many experiment simulators corresponding to these parameter choices. The simulator explores a broad parameter space, for example, range of stringencies in folded-structural/topological uniqueness, low free energy conformational states, and sequence uniqueness required for favorable pharmacology. Ultimately the algorithms described herein discover a very rare pool of productive aptamers from within a large pool, employing lean sequential experiments and feedback control design.

Aptamers have been developed through SELEX and other methods to have highly selective (nanomolar range) dissociation constants with a variety of molecular targets. However, aptamers identified through in vitro processes can frequently behave differently when brought into an in vivo context, or when attached to the therapeutic OBM. Given these challenges, these methods rely on a sensitive and high-throughput of single cell NGS assay to monitor both the concentration of delivered OBM (PK) as well as the relative efficacy of the delivered OBM measured by gene knock-down or splicing modulation (PD).

Figure 6:
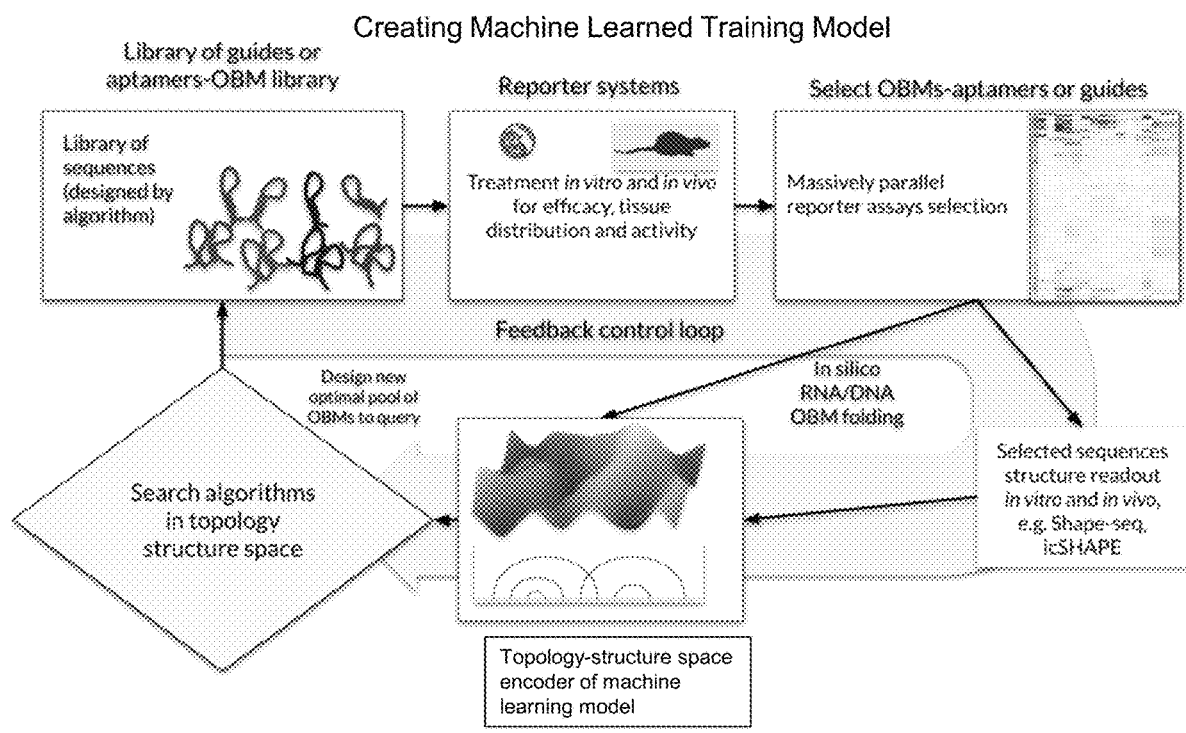
FIG. 6 depicts an overview of the CAT-TAC aptamer optimization method. Starting with a random pool of aptamer sequences (upper left), an animal or in vitro system is dosed with a mixture of OBM:aptamer compounds. The OBM is the same for all aptamers and targets a ubiquitously expressed reporter (e.g. Malat1). Using single nuclei sequencing methods adapted to only amplify aptamers, reporter gene and a few marker genes, the relative molecular abundance of each aptamer is tracked at a single cell level, and the relative knockdown and various cell marker attributes (cell health, state, etc.) are observed. Optionally, Shape-seq reagents can be applied prior to sequencing to allow for adding structural constraints if needed. Aptamer sequences found in nuclei are clustered by shape and pharmacology. These identified structures are then selected for refinement with randomization added to regions of interest as determined by the search algorithm(s) described herein.

The methods of the present disclosure leverage advances in single cell biology to both improve the performance of molecular selection and enable structural generalizations, which are critical in ensuring that the identified aptamer classes are functional for any therapeutic or diagnostic OBM. The core experimental methods in the CAT-TAC optimization strategy are outlined in FIG. 6. The first step of these experiments involved dosing mice or other complex cellular system such as an organoids, patient derived xenografts, or tissue-on-chip systems with a limited-diversity library of random aptamers coupled to a OBM that targets a ubiquitously highly expressed gene known to be sensitive to OBM modulation such as Malat1. After 1-2 weeks of dosing, animals were sacrificed, and organs harvested. Prior to sacrificing animals they were exposed to a SHAPE-reagent which marked unstructured bases on both endogenous RNA and aptamers developed by aspects of present method. Single nuclei suspensions were created and subjected to a modified single cell RNAseq protocol that used custom RT primers to only prime first-strands from the target gene and the aptamers that happen to have gained access to the cell. Primers that monitored several additional cell-health and cell identity marker genes were also included. Notably, in addition to monitoring both the target gene knock-down, the various markers of cell health, the methods described herein were able to extract aptamer abundance and in vivo SHAPE-seq structural constraints and abundance for all aptamers present. The resulting data provided a cell-type resolved picture of both target knockdown which integrates (PK and PD processes), along with the family of aptamers which were instrumental in enhanced transport into the nucleus of the cell. It was anticipated that more than one aptamer will be present in each cell—the cell "votes" for an aptamer sequence, but more importantly, "votes" on an aptamer class defined by the topological and structural clusters. To illustrate this point: for a specific cell-type, the aptamer sequence with highest votes across hundreds/thousands of instances of that cell-type are top performers (selected aptamers). However, what structural/topological properties and sequence elements were common between the top performing aptamers for that cell-type, or across multiple cell-types? These structural/topological properties reduced the high-dimensional sequence space of all possible aptameric sequences into much lower dimensional design space that is described herein, characterizing the freedom in sequence-mutational diversity in aptamers within classes of the same functional outcome.

CAT-TAC deviated significantly from SELEX. The methods described in aspects of the present disclosure are not optimizing for binding to a specific ligand, nor are performing a binding sequence elution/amplification step to select for a few sequences against a specific target. Traditional SELEX approach may be counterproductive for the purpose of robustly enhancing PK because of specificity to ligands. The method described in the aspects of the present disclosure maintains both specific and non-specific/moderate binding to several cell-surface and endosomal receptors contributing to general enhancement of OBM uptake, either for a particular tissue/cell-type or broadly. Therefore, CAT-TAC maintains a large population of distinct classes of aptamers, whose enhancement of cell/tissue specific nuclear-delivery of OBM-payload is assessed directly at single-nucleus sequencing readout. The selection step of the present method is partly algorithmic—it is informed directly by the CAT-TAC data and augmented by auxiliary information on sequence-structure-topology mapping from SHAPE-seq and in silico folding tools. CAT-TAC's sequence-topology space algorithms do not simply perform a selection of the current pool but rather designs novel sequences that are expected to fall within a topology-structure class. These classes are expected to be robust to sequence mutations while still maintaining desired pharmacology or enhance pharmacology by optimally exploring the relevant topology-structure class by designing in a new aptamer library.

Figure 5:
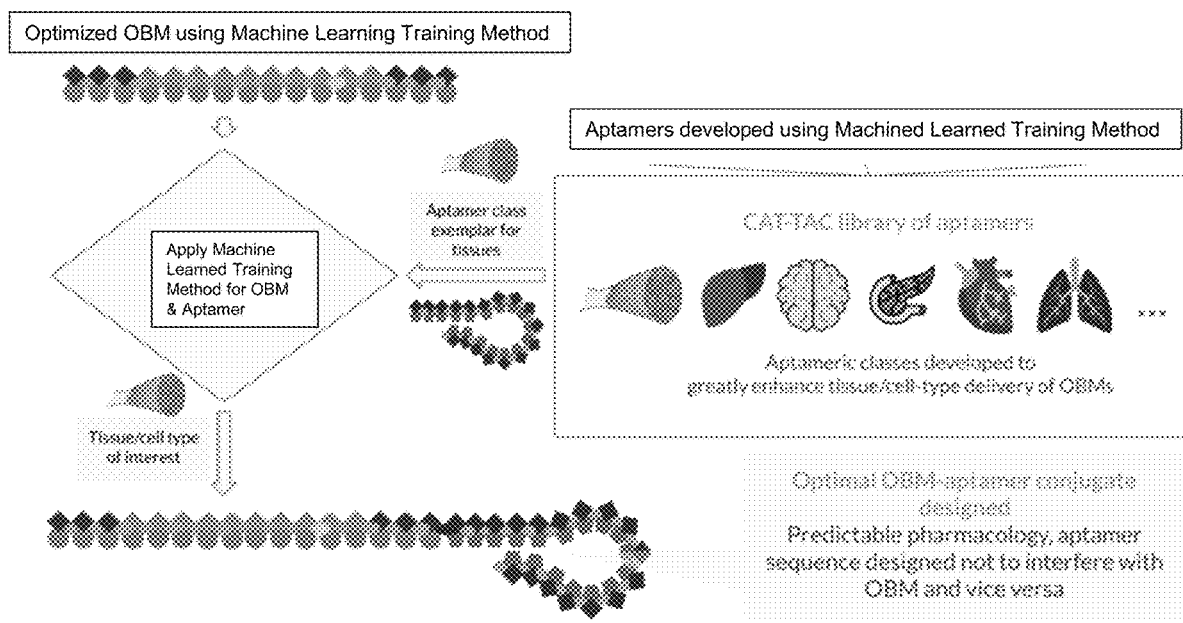
FIG. 5 shows a schematic of how CAT-TAC (Creyon Aptamers for Targeting Tissues and Cells) powers the creation of precision targeted OBMs. A target structure is selected from the library of aptamer structures created in Example 2. Using the engine described herein, a sequence and chemistry modified version of the aptamer is created that shares the structural, biophysical properties of the parent structure. The resulting aptamer is engineered to be compatible with the "payload" OBM and optimized to be well tolerated. The newly engineered aptamer is then synthesized as an extension to the "payload" OBM which is engineered using the engine described herein. This process is scalable to enable the rapid creation of novel gene-expression modulating OBMs that can be programmed to selectively affect specific cells and tissues.

Significant advantages of using aptamers to deliver OBMs are their relatively small size (20-100 nt), and that their building blocks are also nucleic acids just like OBMs. This makes synthesis, computational modeling, characterizing sequence-function mappings and engineering such mapping a far more tractable problem. The disadvantage is that the therapeutic payload (OBM) is both highly prone to interact directly with the delivery aptamer and likely to significantly impact the structural and biophysical properties of the aptamer. The methods described in aspects of the present disclosure directly addresses these issues by building a topology-structure space encoding of aptamer-OBMs and evaluating how the OBM will impact the structure of the aptamer (see e.g. FIG. 5) and vice versa.

The present inventors built a rich topology-structure space encoding for aptamer-OBM conjugate polymers, driven by CAT-TAC datasets, topology of RNA folding, tertiary structures, electrostatic interactions, hybridization energetics & biophysics, and constraints on the space provided by SHAPE-seq like readouts. The present inventors built computational methods to evaluate the existing library for an OBM of interest, and design of a specific exemplar aptamer for that OBM which accurately mitigates aptamer-OBM interferences. A computational process was also built to evaluate chemical modifications and sequence substitutions to engineer an aptamer optimal for attaching to any OBM of interest for improved PK in specific tissue/cell type.

One of the key challenges of learning the sequence-to-function map of aptamers is the very high-dimensional space of possible designs, for a 50-mer aptamer, this is roughly $1.2 \times 10^{30}$ possible unique molecule designs. However, a large fraction of these sequences are not expected to have productive interactions with cell-surface receptors, etc. One of embodiments of the present disclosure is encoding any aptamer sequence into a much lower dimensional topology-structure space, which is (a) common structural-motif-aware and encode the sequence dependence of these motifs (b) topology-aware at multiple length-scales (create feature sets on topologically equivalent structures and encode three dimensional interactions into such topological feature sets) (c) able to inform the set of topological and sequence features by (partial) readouts of in vivo RNA structure as contact maps and SHAPE-profiles (SHAPE-seq, SHAPE-Map, M2-Seq, PAIR-Map, etc.). SHAPE-seq has recently been applied to aptamer discovery and the methods described herein extend contact-map methods to aptamers. These readouts were originally developed to either provide two point contact maps or accessibility profiles of full-length folded RNAs-when applied to aptamers, which are much shorter, they are high resolution and have favorable signal-to-noise.

Figure 7:
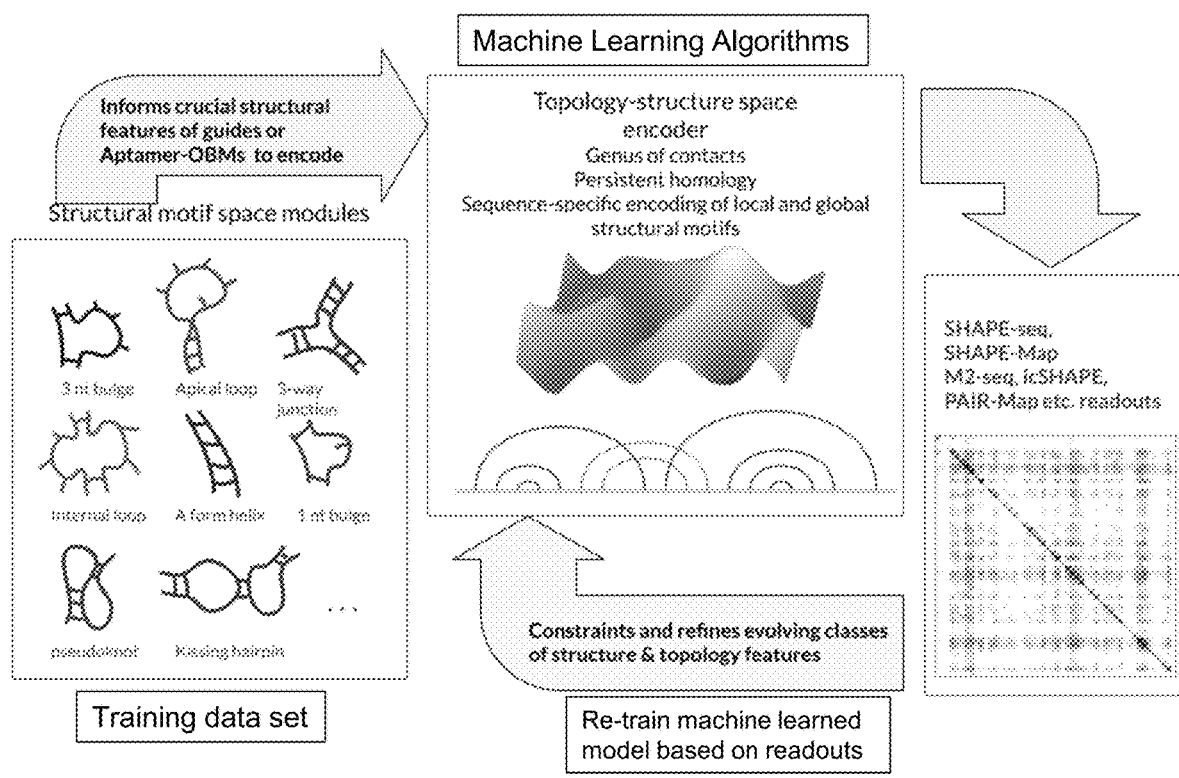
FIG. 7 shows the controller and algorithmic methodology to integrate disparate biophysical, computational and experimental information on 3D structure, topology and sequence relationships of productive aptameric classes, enabling efficient search and robust design criteria for CAT-TAC batches of sequential experimental selection for tissue- and/or cell-type specific aptameric libraries. The topology-structure space described herein is a low-dimensional encoding of the very high-dimensional (and therefore, intractable) sequence space of aptamer-OBM conjugates and is aware of robust classes of structural and sequence motifs mapped to functional outcomes, example of structural motifs are shown in the left panel. The aptamer classes created are defined by the set of sequence mutations or structural perturbations that do not affect aptamer function. CAT-TAC iterations build these classes informed by direct in vivo readouts of both two-point interactions and accessibility profile of aptamer monomers (right panel), as well as rich computational tools in the RNA folding and topological analysis (center panel). For example, the genus of aptamer 'rainbow-diagram' corresponding to contact map, and persistence of genus (persistent homology) across length-scales and sequence compositions is one such feature. The central panel illustrates a 'rainbow-diagram' with genus 1.

One of the innovations of aspects of the methods disclosed of the present disclosure is the building a topology-structure space. Traditional in silico approaches for characterization RNA sequences typically begin with folding the RNA into a minimal energy conformation, with known nucleotide hybridization energetics as input. However, these folding algorithms typically are limited to secondary structure computation, which can be performed in $O(N^3)$ in computation time using dynamic programming where N is the length of the RNA. However, for pseudo-knots and structural motifs, the problem of RNA folding has been shown to be NP-complete, and approximate dynamics programming approaches that include tertiary structures run at $O(N^6)$ in time. Moreover, exploring competing low-energy conformations is computationally costly, and highly influenced by the assumptions made in the energetics. Specific structural motifs for example, the ones shown in FIG. 7, typically need special treatment in realistic models owing to their free energetics being poorly captured by pairwise additive hybridization energetics alone, and they exhibit three-dimensional dynamics pivotal in determining realistic structural conformations of the RNA.

A completely different approach is adopted in aspects of the methods disclosed herein. Linear scaling algorithms, which are very accurate and at par with more costly exact dynamic programming algorithms, were modified to identify a family of low-energy secondary structure states of aptamers (not tertiary structures) and enlist the structural motifs as features in its sequence context. To illustrate this point, the set of features for a single folded secondary structure is a list of secondary states for sequence k-mers along the aptamer 5' to 3', for example, these states could be "stem", "loop", "junction" etc.—a set of structural motifs. The secondary interactions are typically dense, meaning, a large fraction of nucleotides engaged in them. The tertiary structural interactions in contrast are sparse, and this sparsity is exploited in the algorithms in this disclosure. In the space of all possible energetically favorable tertiary structures for a particular secondary structure, topological features were created: (a) the genus and persistence of genus was computed at various length scales, creating persistent homology fingerprints (b) link topological features to both sequence and primary structural motifs described above (c) constraint and inform these sequence-topology features with SHAPE-seq like readouts, in essence, maintaining a rich set descriptors of structural interactions. The tertiary interactions are likely to be most dynamic and relevant in competing aptamer conformational states for the same aptamer sequence. This topological-structural space was refined and reduced in dimensions by continual data input from CAT-TAC assays—the most informative manifold embedded in the original space was identified for each aptamer function studied, see FIG. 7.

This unique topology-structure space enabled the present disclosures to design a specific aptamer sequence for a specific OBM by minimizing OBM-aptamer interaction—to do so a search in this space that minimized both secondary and tertiary structure with OBM was performed, while maintaining the desirable aptamer properties. Moreover, chemical modifications that mitigated such interaction were evaluated using the same principles and validated in experiments.

To deploy CAT-TAC aptamers across a diversity of therapeutic OBMs, a library of aptamer classes was created to serve as the 'scaffold' of the final design of OBM:aptamer therapeutics for a specific OBM.

Figure 8:
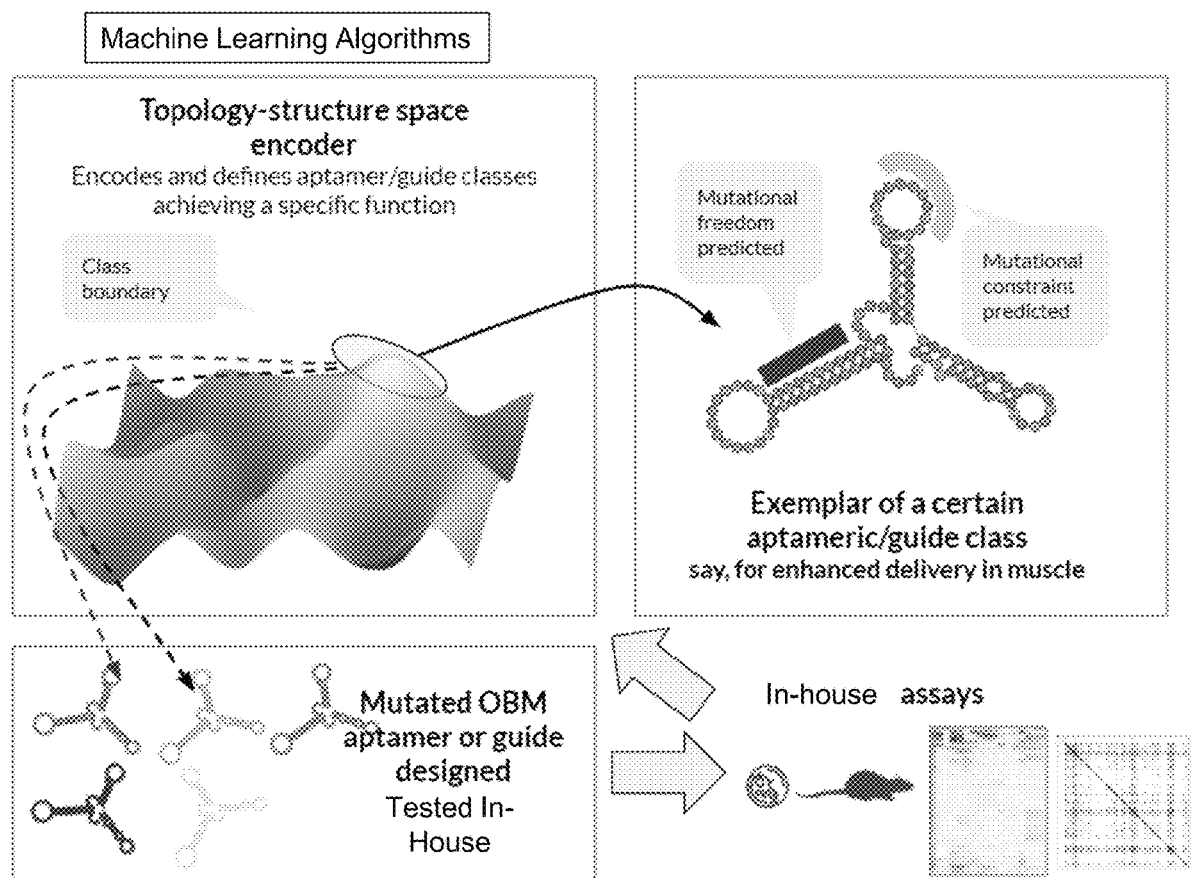
FIG. 8 depicts the directed mutational analysis in Example 2, refining the definition of classes of aptamers by testing a large number of directed mutations of the exemplars aptamers in each class, where the topology-structure space encoding predicts which mutations would be tolerated in retaining the function of the aptamer class, (e.g., delivery in muscle). The utility of the topology-structure space is validated, and walks in this lower dimensional space within class boundaries characterize mutational freedom in aptamer sequence that do not affect its functional merit. This freedom enables engineering of specific realizations of a class, with distinct aptamer sequences tailored for distinct payload OBMs, thereby eliminating unwanted aptamer-OBM interactions.

The examples described herein tested the robustness of the definition of classes in topology-structure space. Specifically, these classes predicted aptamers sequence mutations that were tolerated within a class, meaning, the mutated realizations retained the functional property of the exemplar aptamer in the class. The models were evaluated on multiple classes across tissues/cell-types by designing in silico and testing aptamers for enhancing efficacy of payloads, by designing a large number of mutated aptamers of exemplars in each class and testing them in CAT-TAC assays, see FIG. 8. This step typically also results in a parsimonious and robust definition of these classes improving the models with a directed mutational analysis of sequence-function mapping.

IV.C. Example 3—Initializing the Model—In Vivo Analysis of 16 OBMs in Mice to Initialize the Predictive Model of Systemic Tolerability For the sake of clarity, the methods described herein are now described in the context of a particular example.

This example describes a model initialization step and is constructed for the case of cytotoxicity for a narrow class of OBMs: 16 nucleotide long ASOs with fixed 3-10-3 LNA gapmer chemical scaffold. A first set of oligonucleotides was generated by performing single n-gram mutations to obtain oligonucleotides mapped to a distributed range of probabilities. These oligonucleotides were then synthesized as 16 nucleotide long ASOs with fixed 3-10-3 LNA gapmer chemical scaffold. In order to determine a first measure of correlation between the oligonucleotide and a biophysical effect and create a first training set (calibration), the first set of oligonucleotides (OBMs) were administered to mice and a variety of biophysical effects measured over a 5-week period.

Mice. Male C57BL/6 mice aged 5-6 weeks were maintained on a 12-hour light/dark cycle and were fed ad libitum normal mouse chow. Animals were acclimated for at least 7 days in the research facility before initiation of the experiment. Oligonucleotide-based medicines (OBMs) were prepared in buffered saline (PBS) and sterilized by filtering through a 0.2 micron filter. OBMs were dissolved in PBS for subcutaneous injection.

Survey Study Design. Total Study Design was 5 weeks. On Day −1 (before the study started) body weight was recorded and mice were randomized into 17 total groups of 5 mice each per treatment (16 OBM groups and 1 saline control group). Groups received subcutaneous injections of an OBM at a dose of 75 mg/kg at the start of Week 2, Week 3, Week 4, for 3 total doses. No dose was administered during Week 1 (observation period) or Week 4 (washout period).

Blood draws (via eye bleed, tail bleed or cardiac bleed) were administered on a weekly basis 72 hours after each dosing or 72 hours after the start of Week 4 during the washout period. Observations and read-outs included body weight (BW), temperature, ALT, AST, BUN, creatinine, CRP and total bilirubin (TBILI). CBC analysis was performed on anticoagulated whole blood samples and measurements included neutrophils (%), neutrophil (/uL), reticulocytes (%), WBC (K/uL), absolute reticulocyte (K/uL), RBC (M/uL), HGB (g/dL), lymphocyte (/uL), lymphocytes (%), nucleated RBC (/100 WBC), HCT (%), monocyte (/uL), monocytes (%), polychromasia, anisocytosis, eosinophil (/uL), eosinophils (%), MCV (fL), basophil (/uL), basophils (%), MCH (pg), poikilocytosis, heinz bodies, MCHC (g/dL), metamyelocyte (/uL), metamyelocyte (%), myelocyte (/uL), platelet estimate, myelocyte (%) platelet count (K/uL), promyelocyte (/uL), promyelocyte (%) and combinations thereof.

On Week 5 animals were sacrificed and wet tissue weight measured for liver, kidney and spleen.

Exemplary training data at week 5 of the study are shown in Table 1. Importantly, there were six OBMs correlated with safe biophysical effects, and ten OBMs correlated with toxic biophysical effects, as measured over a 5-week period, which was sufficient to initialize the model. Any number of oligonucleotides can be used to create a first training set, so long as there are sufficient representatives for one or more measured biophysical effects.

TABLE 1

Exemplary Week 5 initialization data for 16 OBMs

| Experimental Group | No. of mice | 5 wk Survival | ALT (U/L) | AST (U/L) | BUN (mg/dL) | Creatinine (mg/dL) | Temp (° C.) | Liver (g) | Kidney (g) | Spleen (g) | Train |
|---|---|---|---|---|---|---|---|---|---|---|---|
| Saline Control | 5 | 5 | 22.4 | 47.2 | 21.6 | 0.464 | 30.8 | 1.206 | 0.3244 | 0.0888 | — |
| 281023 | 5 | 5 | 568.8 | 304.4 | 28 | 0.476 | 31.2 | 1.5266 | 0.3024 | 0.1084 | TOXIC |
| 205873 | 5 | 5 | 22.4 | 36.8 | 17.6 | 0.484 | 31.7 | 1.1252 | 0.3138 | 0.0946 | SAFE |
| 997423 | 5 | 3 | 2266.6 | 3500.0 | 34 | 0.353 | 30.7 | 1.3407 | 0.2706 | 0.0793 | TOXIC |
| 35695 | 5 | 0 | dead | dead | dead | dead | dead | dead | dead | dead | TOXIC |

TABLE 1-continued

Exemplary Week 5 initialization data for 16 OBMs

| Experimental Group | No. of mice | 5 wk Survival | ALT (U/L) | AST (U/L) | BUN (mg/dL) | Creatinine (mg/dL) | Temp (° C.) | Liver (g) | Kidney (g) | Spleen (g) | Train |
|---|---|---|---|---|---|---|---|---|---|---|---|
| 510126 | 5 | 0 | dead | dead | dead | dead | dead | dead | dead | dead | TOXIC |
| 167146 | 5 | 5 | 3270.0 | 3930 | 30 | 0.44 | 31.3 | 1.3312 | 0.3208 | 0.0772 | TOXIC |
| 8478 | 5 | 5 | 109.2 | 86.4 | 23.6 | 0.484 | 31.8 | 1.582 | 0.3354 | 0.109 | SAFE |
| 320139 | 5 | 5 | 418.4 | 470.8 | 26 | 0.42 | 30.6 | 1.1582 | 0.3034 | 0.1018 | TOXIC |
| 709292 | 5 | 5 | 2740.0 | 21000 | 24.4 | 0.452 | 30.9 | 1.5452 | 0.375 | 0.171 | TOXIC |
| 571851 | 5 | 5 | 76.8 | 89.6 | 23.6 | 0.496 | 31.5 | 1.2884 | 0.3624 | 0.1056 | SAFE |
| 838454 | 5 | 4* | 49 | 84.5 | 20.5 | 0.39 | 30.9 | 1.249 | 0.3252 | 0.1372 | SAFE |
| 859331 | 5 | 5 | 3928 | 4311 | 20.4 | 0.396 | 31.4 | 1.4064 | 0.4254 | 0.1366 | TOXIC |
| 56021 | 5 | 5 | 73.6 | 65.6 | 23.6 | 0.352 | 30.8 | 1.275 | 0.358 | 0.1304 | SAFE |
| 332079 | 5 | 5 | 4260 | 3453 | 22 | 0.316 | 30.5 | 1.3668 | 0.333 | 0.1078 | TOXIC |
| 365383 | 5 | 5 | 316 | 265.2 | 22.4 | 0.324 | 30.3 | 1.3932 | 0.339 | 0.1166 | TOXIC |
| 270917 | 5 | 5 | 38 | 65.6 | 17.2 | 0.384 | 30.4 | 1.3454 | 0.3294 | 0.0978 | SAFE |

*found dead in Week 1 acclimation period prior to first dosing of OBMExample 4 - AUC vs Cmax (additional and independent dosing initialization)

This example describes experiments to initialize Cmax (max effects of dose) vs AUC (Area under the curve, i.e., total dose distributed over a timescale within half-life in tissue) of toxic ASOs.

In particular, this example details a dosing calibration survey step of 2 toxic OBMs (16 nucleotide long ASOs with fixed 3-10-3 LNA gapmer chemical scaffold) interrogated in vivo to calibrate safety and toxicity of three escalating ASO doses of 4 doses of 10 mg/kg, 2 doses of 20 mg/kg and one dose of 40 mg/kg respectively.

Male C57BL/6 mice aged 11-12 weeks were maintained as described in Example 3 above.

Total Study Design was 4 weeks. On Day −1 (before the study started) body weight was recorded and for each OBM treatment mice were randomized into 3 groups (3×10 mg/kg, 2×20 mg/kg or 1×40 mg/kg) of 3 mice per group. One group received a single subcutaneous injection of an OBM at a dose of 40 mg/kg on Friday of Week 1, for a total of 1 dose. Another group received a subcutaneous injection of an OBM at a dose of 20 mg/kg on Monday of Week 1 and Friday of Week 2, for a total of 2 doses. Another group received a subcutaneous injection of an OBM at a dose of 10 mg/kg on Monday and Friday of Week 1 and on Friday of Week 2 for a total of 3 doses.

Observations and read-outs included body weight, urine volume and collection, blood collection, serum and urinary analysis and kidney and liver collection. Urine analysis was performed +24 hours after each dosing and blood analysis was performed +72 hours after dosing. Exemplary hepatotoxicity assays included, but were not limited to serum ALT, AST, and creatine. Exemplary nephrotoxicity assays included but were not limited to urinary KIM-1 and CysC. CBC analysis was performed as described in Example 3 above.

At the end of Week 4 animals were sacrificed and wet tissue weight measured for liver, kidney and spleen.

TABLE 2

Exemplary Dosing Initialization Data - Dosing and Liver Function Tests

| Week | Experimental Group | Dosing | ALT (U/L) | AST (U/L) | CREA (mg/dL) | CysC (pg/mL) | Kim-1 (pg/mL) |
|---|---|---|---|---|---|---|---|
| Week 1 | 810069 | 40 mg/kg (1 Dose) | 118.65 | 115.91 | 0.22 | 252116.67 | 9440.67 |
| | | 20 mg/kg (2 Dose) | 43.26 | 82.75 | .021 | 130094.00 | 10517.00 |
| | | 10 mg/kg (4 dose) | 37.40 | 93.58 | 0.23 | 113872.67 | 7964.00 |
| | 453801 | 40 mg/kg (1 Dose) | 597.25 | 521.97 | 0.26 | 920498.67 | 6096.33 |
| | | 20 mg/kg (2 Dose) | 1065.98 | 880.11 | 0.22 | 1061200.00 | 10940.67 |
| | | 10 mg/kg (4 dose) | 460.33 | 425.83 | 0.30 | 148400.00 | 8540.00 |
| Week 2 | 810069 | 40 mg/kg (1 Dose) | 238.71 | 261.60 | 0.42 | * | * |
| | | 20 mg/kg (2 Dose) | 532.81 | 787.10 | 0.37 | 301170.00 | 9323.50 |
| | | 10 mg/kg (4 dose) | 131.85 | 135.26 | 0.36 | 317895.00 | 12102.50 |
| | 453801 | 40 mg/kg (1 Dose) | 9644.45 | 9843.84 | 1.31 | * | * |
| | | 20 mg/kg (2 Dose) | 11842.79 | 11919.25 | 0.32 | * | * |
| | | 10 mg/kg (4 dose) | 2777.11 | 2733121 | 0.37 | 2485211.00 | 78094.50 |
| Week 3 | 810069 | 40 mg/kg (1 Dose) | 710.85 | 672.59 | 0.32 | * | * |
| | | 20 mg/kg (2 Dose) | 1077.88 | 1237.47 | 0.40 | * | * |
| | | 10 mg/kg (4 dose) | 532.83 | 554.43 | 0.37 | 154632.00 | 7075.00 |
| | 453801 | 40 mg/kg (1 Dose) | 2550.82 | 1698.77 | 0.38 | * | * |
| | | 20 mg/kg (2 Dose) | dead | dead | dead | dead | dead |
| | | 10 mg/kg (4 dose) | 1284.39 | 2124.10 | 0.30 | 2853108.00 | 22327.00 |
| Week 4 | 810069 | 40 mg/kg (1 Dose) | 174.42 | 219.77 | 0.27 | * | * |
| | | 20 mg/kg (2 Dose) | 955.80 | 1234.95 | 0.25 | * | * |
| | | 10 mg/kg (4 dose) | 376.43 | 279.50 | 0.34 | * | * |
| | 453801 | 40 mg/kg (1 Dose) | 1933.55 | 1278.47 | 0.32 | * | * |
| | | 20 mg/kg (2 Dose) | dead | dead | dead | dead | dead |
| | | 10 mg/kg (4 dose) | 2043.27 | 1002.34 | 0.34 | * | * |
| Termination | 810069 | 40 mg/kg (1 Dose) | 327.49 | 347.59 | 0.30 | * | * |
| | | 20 mg/kg (2 Dose) | 247.50 | 334.02 | 0.29 | * | * |
| | | 10 mg/kg (4 dose) | 315.65 | 337.40 | 0.34 | * | * |

TABLE 2-continued

Exemplary Dosing Initialization Data - Dosing and Liver Function Tests

| Week | Experimental Group | Dosing | ALT (U/L) | AST (U/L) | CREA (mg/dL) | CysC (pg/mL) | Kim-1 (pg/mL) |
|---|---|---|---|---|---|---|---|
| | 453801 | 40 mg/kg (1 Dose) | 296.67 | 191.51 | 0.34 | * | * |
| | | 20 mg/kg (2 Dose) | dead | dead | dead | dead | dead |
| | | 10 mg/kg (4 dose) | 246.13 | 230.00 | 0.38 | * | * |

* Note:
Urine was collected only from mice dosed with OBM.

TABLE 3

Exemplary Dosing Initialization Data - Body Weight and Terminal Organ Weight

| Experimental Group | Dosing | Dose 1 BW (g) | Dose 2 BW (g) | Dose 3 BW (g) | Liver (mg) | Kidney (mg) | Spleen (mg) |
|---|---|---|---|---|---|---|---|
| 810069 | 40 mg/kg (1 Dose) | 25.81 | 24.80 | 25.05 | 1746 | 344 | 79 |
| | 20 mg/kg (2 Dose) | 25.09 | 24.90 | 24.05 | 1358 | 348 | 81 |
| | 10 mg/kg (4 dose) | 25.55 | 24.028 | 24.11 | 1639 | 340 | 101 |
| 453801 | 40 mg/kg (1 Dose) | 26.21 | 22.92 | 20.4* | 1347 | 299 | 60 |
| | 20 mg/kg (2 Dose) | 26.20 | 23.43 | dead | dead | dead | dead |
| | 10 mg/kg (4 dose) | 26.26 | 25.11 | 23.10 | 1210 | 295 | 77 |

*Note -
2 of 3 mice dead

IV.D. Example 5—Active Learning Step—Step 1—Acute In Vivo Survey of 128 OBMs in Mice to Refine Predictive Regression Model of Systemic Tolerability This example details Step 1 of an active learning survey step of 128 OBMs (16 nucleotide long ASOs with fixed 3-10-3 LNA gapmer chemical scaffold) interrogated in vivo to evaluate the safety and toxicity of OBMs engineered by the methods described herein.

Mice. Male C57BL/6 mice were maintained as described in Example 3 above.

Acute Study Design. Total Study Design was 3 days (72 hours). On Day −1 (before the study started) body weight was recorded and mice were randomized into groups of 2 mice each per treatment (OBM or control). The foundational survey instrument comprised 128 compounds surveyed over 4 groups with 32 compounds interrogated per group. Groups received subcutaneous injections of an OBM at a dose of 75 mg/kg at the start of the study. Clinical chemistry data were collected at 24 hours and 72 hours post-administration. Animals were sacrificed at 72 hours.

Observations and read-outs included body weight (BW), temperature, ALT, AST, BUN, creatinine, CRP and total bilirubin (TBILI). CBC analysis was performed on anticoagulated whole blood samples and measurements included neutrophils (%), neutrophil (/uL), reticulocytes (%), WBC (K/uL), absolute reticulocyte (K/uL), RBC (M/uL), HGB (g/dL), lymphocyte (/uL), lymphocytes (%), nucleated RBC (/100 WBC), HCT (%), monocyte (/uL), monocytes (%), polychromasia, anisocytosis, eosinophil (/uL), eosinophils (%), MCV (fL), basophil (/uL), basophils (%), MCH (pg), poikilocytosis, heinz bodies, MCHC (g/dL), metamyelocyte (/uL), metamyelocyte (%), myelocyte (/uL), platelet estimate, myelocyte (%) platelet count (K/uL), promyelocyte (/uL), promyelocyte (%) and combinations thereof.

Exemplary active learning data are shown in Tables 4, 5, 6, 7, 8, 9, 10, 11 and 12 and were used to build a Step 1 regression model of toxicity. OBMs with ALT levels ≤100 U/L at 72 hours after administration (post-administration) were trained as safe and ALT levels ≥200 U/L as toxic.

TABLE 4

Exemplary Step 1 acute active learning data @ 24 hours (Group 1)

| Experimental Group | No. of mice | 24 hr Survival | Dosing BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 21.98 | 28 | 61 | 21 | 0.34 | 0.19 | 0.70 | — |
| 321969 | 2 | 2 | 20.35 | 55 | 68 | 21 | 0.35 | 0.27 | 0.80 | SAFE |
| 75408 | 2 | 2 | 22.73 | 45 | 46 | 24 | 0.29 | 0.40 | 0.60 | SAFE |
| 454453 | 2 | 2 | 23.00 | 38 | 55 | 24 | 0.33 | 0.25 | 0.80 | |
| 895121 | 2 | 2 | 21.17 | 41 | 48 | 23 | 0.29 | 0.28 | 0.70 | |
| 658579 | 2 | 2 | 23.68 | 46 | 51 | 23 | 0.42 | 0.37 | 0.80 | SAFE |
| 978800 | 2 | 2 | 22.34 | 58 | 44 | 24 | 0.27 | 0.31 | 0.60 | TOXIC |
| 984883 | 2 | 2 | 21.33 | 42 | 42 | 23 | 0.27 | 0.17 | 0.60 | SAFE |
| 550074 | 2 | 2 | 22.21 | 41 | 45 | 27 | 0.39 | 0.16 | 0.80 | SAFE |
| 475483 | 2 | 2 | 20.73 | 53 | 53 | 21 | 0.36 | 0.07 | 0.90 | |
| 586100 | 2 | 2 | 20.85 | 35 | 38 | 21 | 0.33 | 0.15 | 0.50 | |
| 807174 | 2 | 2 | 22.56 | 54 | 57 | 24 | 0.36 | 0.16 | 0.80 | |

TABLE 4-continued

Exemplary Step 1 acute active learning data @ 24 hours (Group 1)

| Experimental Group | No. of mice | 24 hr Survival | Dosing BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| 780896 | 2 | 2 | 20.81 | 56 | 60 | 19 | 0.35 | 0.09 | 0.90 | SAFE |
| 589215 | 2 | 2 | 21.19 | 29 | 49 | 23 | 0.37 | 0.07 | 0.70 | SAFE |
| 953213 | 2 | 2 | 22.33 | 36 | 48 | 21 | 0.36 | 0.03 | 0.70 | SAFE |
| 745787 | 2 | 2 | 21.89 | 51 | 46 | 20 | 0.28 | 0.03 | 0.60 | SAFE |
| 271136 | 2 | 2 | 21.45 | 41 | 42 | 27 | 0.28 | 0.01 | 0.60 | TOXIC |
| 237297 | 2 | 2 | 21.67 | 40 | 53 | 35 | 0.37 | 0.00 | 1.00 | TOXIC |
| 585158 | 2 | 2 | 21.66 | 48 | 54 | 28 | 0.37 | 0.18 | 1.00 | SAFE |
| 7313 | 2 | 2 | 21.24 | 37 | 47 | 33 | 0.42 | 0.10 | 0.50 | SAFE |
| 915197 | 2 | 2 | 22.03 | 41 | 73 | 22 | 0.33 | 0 | 1.00 | SAFE |
| 552066 | 2 | 2 | 21.50 | 50 | 24 | 24 | 0.26 | 0.06 | 0.50 | SAFE |
| 829201 | 2 | 2 | 21.18 | 33 | 46 | 24 | 0.34 | 0.08 | 0.50 | SAFE |
| 852114 | 2 | 2 | 21.83 | 42 | 50 | 27 | 0.36 | 0.06 | 0.80 | SAFE |
| 205017 | 2 | 2 | 22.35 | 50 | 48 | 25 | 0.30 | 0.28 | 0.60 | SAFE |
| 355821 | 2 | 2 | 21.31 | 37 | 44 | 21 | 0.36 | 0.09 | 0.60 | SAFE |
| 956379 | 2 | 2 | 21.81 | 39 | 43 | 23 | 0.33 | 0.17 | 0.60 | TOXIC |
| 866952 | 2 | 2 | 20.44 | 38 | 50 | 26 | 0.33 | 0.22 | 0.90 | TOXIC |
| 14300 | 2 | 2 | 23.40 | 39 | 52 | 24 | 0.43 | 0.22 | 0.50 | SAFE |
| 678794 | 2 | 2 | 20.90 | 47 | 53 | 22 | 0.45 | 0.17 | 0.50 | TOXIC |
| 825173 | 2 | 2 | 21.33 | 41 | 43 | 25 | 0.33 | 0.04 | 0.60 | TOXIC |
| 953122 | 2 | 2 | 21.62 | 29 | 46 | 23 | 0.32 | 0.10 | 0.60 | TOXIC |
| 292462 | 2 | 2 | 23.00 | 41 | 40 | 23 | 0.31 | 0.21 | 0.50 | TOXIC |

TABLE 5

Exemplary Step 1 acute active learning data @ 72 hours post administration (Group 1)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 21.91 | 23 | 76 | 26 | 0.34 | 0.00 | 0.40 | — |
| 321969 | 2 | 2 | 21.19 | 53 | 309 | 23 | 0.29 | 0.24 | 0.60 | SAFE |
| 75408 | 2 | 2 | 22.74 | 42 | 84 | 22 | 0.28 | 0.00 | 0.40 | SAFE |
| 454453 | 2 | 2 | 22.32 | 126 | 145 | 23 | 0.32 | 0.16 | 0.30 | |
| 895121 | 2 | 2 | 21.81 | 133 | 336 | 25 | 0.32 | 0.40 | 0.60 | |
| 658579 | 2 | 2 | 23.62 | 52 | 360 | 25 | 0.32 | 0.18 | 0.60 | SAFE |
| 978800 | 2 | 2 | 21.52 | 1110 | 2719 | 10 | 0.29 | 0.00 | 1.20 | TOXIC |
| 984883 | 2 | 1* | 21.22 | 60 | 130 | 34 | 0.24 | 0.00 | 0.60 | SAFE |
| 550074 | 2 | 2 | 21.68 | 44 | 184 | 24 | 0.25 | 0.14 | 0.70 | SAFE |
| 475483 | 2 | 1* | 21.10 | 156 | 638 | 24 | 0.32 | 0.18 | 1.00 | |
| 586100 | 2 | 1* | 21.57 | 126 | 148 | 26 | 0.24 | 0.10 | 0.40 | |
| 807174 | 2 | 2 | 23.02 | 140 | 172 | 20 | 0.33 | 0.29 | 0.60 | |
| 780896 | 2 | 1* | 21.16 | 56 | 82 | 26 | 0.32 | 0.16 | 0.40 | SAFE |
| 589215 | 2 | 2 | 21.91 | 31 | 91 | 23 | 0.31 | 0.08 | 0.60 | SAFE |
| 953213 | 2 | 2 | 22.33 | 33 | 86 | 23 | 0.31 | 0.16 | 0.30 | SAFE |
| 745787 | 2 | 2 | 22.30 | 42 | 53 | 21 | 0.37 | 0.14 | 0.40 | SAFE |
| 271136 | 2 | 2 | 21.21 | 452 | 559 | 27 | 0.29 | 0.22 | 0.90 | TOXIC |
| 237297 | 2 | 0 | — | — | — | — | — | — | — | TOXIC |
| 585158 | 2 | 2 | 21.81 | 48 | 192 | 30 | 0.30 | 0.34 | 0.50 | SAFE |
| 7313 | 2 | 1* | 21.49 | 26 | 68 | 30 | 0.26 | 0.04 | 0.40 | SAFE |
| 915197 | 2 | 2 | 22.35 | 26 | 73 | 25 | 0.29 | 0.05 | 0.40 | SAFE |
| 552066 | 2 | 1* | 21.99 | 82 | 354 | 20 | 0.40 | 0.16 | 0.60 | SAFE |
| 829201 | 2 | 2 | 22.18 | 66 | 104 | 22 | 0.37 | 0.10 | 0.30 | SAFE |
| 852114 | 2 | 2 | 22.04 | 49 | 69 | 23 | 0.29 | 0.14 | 0.30 | SAFE |
| 205017 | 2 | 2 | 21.86 | 25 | 40 | 23 | 0.29 | 0.06 | 0.20 | SAFE |
| 355821 | 2 | 2 | 21.92 | 35 | 78 | 21 | 0.33 | 0.07 | 0.40 | SAFE |
| 956379 | 2 | 2 | 21.10 | 1850 | 4950 | 22 | 0.06 | 0.03 | 3.00 | TOXIC |
| 866952 | 2 | 1* | 20.59 | 800 | 1000 | 20 | 0.36 | 0.20 | 1.00 | TOXIC |
| 14300 | 2 | 2 | 23.56 | 68 | 94 | 18 | 0.33 | 0.04 | 0.60 | SAFE |
| 678794 | 2 | 2 | 20.82 | 280 | 249 | 22 | 0.33 | 0.05 | 0.60 | TOXIC |
| 825173 | 2 | 1* | 21.19 | 5000 | 5480 | 20 | 0.34 | 0.16 | 1.00 | TOXIC |
| 953122 | 2 | 2 | 21.68 | 552 | 520 | 15 | 0.22 | 0.07 | 0.40 | TOXIC |
| 292462 | 2 | 2 | 22.73 | 220 | 110 | 19 | 0.26 | 0.18 | 0.40 | TOXIC |

*clot

TABLE 6

Exemplary Step 1 acute active learning data @ 24 hours post-administration (Group 2)

| Experimental Group | No. of mice | 24 hr Survival | Dosing BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 21.97 | 29 | 41 | 24 | 0.23 | 0.09 | 0.50 | — |
| 70160 | 2 | 2 | 22.28 | 47 | 24 | 24 | 0.29 | 0.13 | 0.60 | SAFE |
| 692064 | 2 | 2 | 22.87 | 43 | 41 | 19 | 0.38 | 0.13 | 0.40 | SAFE |
| 814059 | 2 | 2 | 24.63 | 32 | 39 | 25 | 0.27 | 0.06 | 0.50 | SAFE |
| 835697 | 2 | 2 | 23.00 | 35 | 40 | 24 | 0.27 | 0.27 | 0.40 | SAFE |
| 359245 | 2 | 2 | 24.13 | 42 | 57 | 26 | 0.28 | 0.15 | 0.70 | SAFE |
| 146606 | 2 | 2 | 23.32 | 44 | 41 | 20 | 0.31 | 0.10 | 0.40 | TOXIC |
| 574235 | 2 | 2 | 22.79 | 38 | 62 | 27 | 0.26 | 0.10 | 0.40 | TOXIC |
| 551123 | 2 | 2 | 22.45 | 40 | 47 | 25 | 0.33 | 0.35 | 0.60 | SAFE |
| 11559 | 2 | 2 | 23.11 | 41 | 49 | 26 | 0.31 | 0.11 | 0.60 | SAFE |
| 628903 | 2 | 2 | 22.95 | 31 | 41 | 22 | 0.26 | 0.04 | 0.50 | SAFE |
| 960675 | 2 | 2 | 23.39 | 47 | 44 | 30 | 0.28 | 0.23 | 0.70 | SAFE |
| 24282 | 2 | 2 | 24.52 | 48 | 44 | 20 | 0.35 | 0.29 | 0.60 | TOXIC |
| 687156 | 2 | 2 | 22.59 | 30 | 48 | 22 | 0.31 | 0.13 | 0.60 | SAFE |
| 43504 | 2 | 2 | 23.88 | 40 | 47 | 21 | 0.24 | 0.15 | 0.60 | TOXIC |
| 769032 | 2 | 2 | 22.95 | 35 | 43 | 23 | 0.31 | 0.20 | 0.60 | SAFE |
| 953723 | 2 | 2 | 22.705 | 56 | 55 | 21 | 0.23 | 0.19 | 0.60 | TOXIC |
| 441788 | 2 | 2 | 23.73 | 36 | 47 | 21 | 0.23 | 0.22 | 0.80 | SAFE |
| 208910 | 2 | 2 | 22.95 | 38 | 42 | 23 | 0.26 | 0.12 | 0.50 | |
| 656462 | 2 | 2 | 24.03 | 37 | 51 | 20 | 0.35 | 0.22 | 0.80 | SAFE |
| 687114 | 2 | 2 | 23.97 | 35 | 45 | 22 | 0.34 | 0.16 | 0.60 | SAFE |
| 651507 | 2 | 2 | 23.08 | 45 | 51 | 21 | 0.33 | 0.02 | 0.60 | SAFE |
| 665810 | 2 | 2 | 23.99 | 37 | 43 | 21 | 0.31 | 0.07 | 0.60 | SAFE |
| 846421 | 2 | 2 | 21.30 | 40 | 48 | 23 | 0.32 | 0.20 | 0.70 | SAFE |
| 703478 | 2 | 2 | 25.36 | 44 | 42 | 21 | 0.28 | 0.11 | 0.60 | SAFE |
| 229968 | 2 | 2 | 22.41 | 38 | 44 | 22 | 0.24 | 0.16 | 0.70 | SAFE |
| 947698 | 2 | 2 | 26.91 | 62 | 41 | 20 | 0.14 | 0.22 | 0.40 | SAFE |
| 885459 | 2 | 2 | 25.21 | 42 | 49 | 17 | 0.30 | 0.17 | 0.60 | SAFE |
| 871001 | 2 | 2 | 22.89 | 35 | 42 | 23 | 0.30 | 0.15 | 0.40 | |
| 827865 | 2 | 2 | 24.76 | 39 | 42 | 19 | 0.29 | 0.16 | 0.70 | SAFE |
| 330302 | 2 | 2 | 22.01 | 50 | 61 | 24 | 0.24 | 0.11 | 0.60 | TOXIC |
| 502160 | 2 | 2 | 23.96 | 41 | 43 | 22 | 0.25 | 0.29 | 0.50 | SAFE |
| 234899 | 2 | 2 | 23.51 | 37 | 39 | 21 | 0.27 | 0.41 | 0.50 | SAFE |

TABLE 7

Exemplary Step 1 acute active learning data @ 72 hours post-administration (Group 2)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 22.40 | 33 | 51 | 29 | 0.25 | 0.11 | 0.50 | — |
| 70160 | 2 | 2 | 22.74 | 54 | 63 | 30 | 0.28 | 0.06 | 0.50 | SAFE |
| 692064 | 2 | 2 | 23.56 | 55 | 50 | 24 | 0.28 | 0.19 | 0.20 | SAFE |
| 814059 | 2 | 2 | 24.64 | 28 | 45 | 24 | 0.21 | 0.13 | 0.50 | SAFE |
| 835697 | 2 | 2 | 23.44 | 26 | 42 | 25 | 0.33 | 0.07 | 0.40 | SAFE |
| 359245 | 2 | 2 | 24.25 | 46 | 55 | 29 | 0.28 | 0.06 | 0.40 | SAFE |
| 146606 | 2 | 2 | 23.23 | 1586 | 1314 | 8 | 0.33 | 0.07 | 0.60 | TOXIC |
| 574235 | 2 | 2 | 23.22 | 3786 | 1871 | 11 | 0.31 | 0.22 | 0.60 | TOXIC |
| 551123 | 2 | 2 | 22.67 | 50 | 62 | 28 | 0.22 | 0.11 | 0.40 | SAFE |
| 11559 | 2 | 2 | 23.21 | 46 | 61 | 34 | 0.22 | 0.13 | 0.50 | SAFE |
| 628903 | 2 | 2 | 23.18 | 41 | 63 | 24 | 0.26 | 0.11 | 0.40 | SAFE |
| 960675 | 2 | 2 | 23.50 | 37 | 45 | 32 | 0.25 | 0.24 | 0.40 | SAFE |
| 24282 | 2 | 2 | 23.58 | 4850 | 4233 | 19 | 0.21 | 0.14 | 0.50 | TOXIC |
| 687156 | 2 | 2 | 22.80 | 36 | 78 | 20 | 0.28 | 0.28 | 0.40 | SAFE |
| 43504 | 2 | 2 | 22.68 | 7683 | 5016 | 21 | 0.25 | 0.23 | 1.20 | TOXIC |
| 769032 | 2 | 2 | 23.60 | 31 | 59 | 19 | 0.28 | 0.09 | 0.40 | SAFE |
| 953723 | 2 | 2 | 22.10 | 717 | 775 | 18 | 0.20 | 0.01 | 0.80 | TOXIC |
| 441788 | 2 | 2 | 24.07 | 33 | 48 | 24 | 0.29 | 0.21 | 0.50 | SAFE |
| 208910 | 2 | 2 | 23.07 | 115 | 119 | 26 | 0.27 | 0.06 | 0.60 | |
| 656462 | 2 | 2 | 23.95 | 38 | 69 | 22 | 0.33 | 0.22 | 0.70 | SAFE |
| 687114 | 2 | 2 | 24.06 | 29 | 50 | 25 | 0.33 | 0.24 | 0.40 | SAFE |
| 651507 | 2 | 2 | 23.10 | 56 | 58 | 25 | 0.35 | 0.19 | 0.50 | SAFE |
| 665810 | 2 | 2 | 23.35 | 38 | 58 | 22 | 0.25 | 0.04 | 0.60 | SAFE |
| 846421 | 2 | 2 | 22.25 | 32 | 49 | 26 | 0.32 | 0.24 | 0.40 | SAFE |
| 703478 | 2 | 2 | 25.81 | 39 | 58 | 25 | 0.33 | 0.11 | 0.60 | SAFE |
| 229968 | 2 | 2 | 22.96 | 31 | 47 | 21 | 0.28 | 0.22 | 0.30 | SAFE |
| 947698 | 2 | 2 | 26.91 | 56 | 83 | 21 | 0.29 | 0.07 | 0.20 | SAFE |
| 885459 | 2 | 2 | 25.85 | 52 | 63 | 19 | 0.26 | 0.00 | 0.40 | SAFE |

TABLE 7-continued

Exemplary Step 1 acute active learning data @ 72 hours post-administration (Group 2)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| 871001 | 2 | 2 | 23.13 | 153 | 183 | 22 | 0.27 | 0.24 | 0.40 | |
| 827865 | 2 | 2 | 25.33 | 39 | 53 | 22 | 0.34 | 0.20 | 0.50 | SAFE |
| 330302 | 2 | 2 | 21.88 | 872 | 625 | 21 | 0.30 | 0.10 | 0.60 | TOXIC |
| 502160 | 2 | 2 | 24.59 | 38 | 46 | 24 | 0.27 | 0.10 | 0.60 | SAFE |
| 234899 | 2 | 2 | 24.01 | 42 | 59 | 22 | 0.31 | 0.20 | 0.40 | SAFE |

TABLE 8

Exemplary Step 1 acute active learning data @ 24 hours post-administration (Group 3)

| Experimental Group | No. of mice | 24 hr Survival | Dosing BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 23.28 | 24 | 40 | 20.37 | 0.29 | 0.17 | 0.44 | — |
| 634433 | 2 | 2 | 22.29 | 31 | 36 | 17.96 | 0.28 | 0.27 | .037 | SAFE |
| 52553 | 2 | 2 | 23.53 | 30 | 38 | 17.72 | 0.35 | 0.23 | 0.45 | SAFE |
| 89422 | 2 | 2 | 23.77 | 29 | 39 | 18.44 | 0.32 | 0.16 | 0.47 | SAFE |
| 252689 | 2 | 2 | 22.15 | 34 | 40 | 24.20 | 0.32 | 0.24 | 0.45 | |
| 534368 | 2 | 2 | 21.94 | 32 | 31 | 18.65 | 0.33 | 0.18 | 0.30 | SAFE |
| 125535 | 2 | 2 | 22.46 | 37 | 52 | 22.54 | 0.26 | 0.01 | 0.46 | TOXIC |
| 531745 | 2 | 2 | 24.92 | 32 | 61 | 25.06 | 0.34 | 0.13 | 0.41 | TOXIC |
| 711284 | 2 | 2 | 22.21 | 34 | 23 | 16.95 | 0.26 | 0.07 | 0.38 | SAFE |
| 982426 | 2 | 2 | 24.26 | 31 | 46 | 18.95 | 0.30 | 0.23 | 0.67 | SAFE |
| 122106 | 2 | 2 | 21.12 | 52 | 42 | 21.63 | 0.32 | 0.19 | 0.49 | TOXIC |
| 82284 | 2 | 2 | 24.87 | 25 | 37 | 21.72 | 0.37 | 0.35 | 0.46 | SAFE |
| 328861 | 2 | 2 | 22.33 | 31 | 56 | 19.70 | 0.36 | 0.08 | 0.33 | SAFE |
| 432289 | 2 | 2 | 19.96 | 32 | 48 | 19.75 | 0.30 | 0.20 | 0.34 | SAFE |
| 546096 | 2 | 2 | 24.19 | 36 | 40 | 21.91 | 0.28 | 0.26 | 0.71 | SAFE |
| 227340 | 2 | 2 | 24.29 | 29 | 56 | 25.58 | 0.43 | 0.24 | 0.40 | SAFE |
| 111307 | 2 | 2 | 21.24 | 31 | 38 | 23.63 | 0.36 | 0.07 | 0.42 | SAFE |
| 155024 | 2 | 2 | 22.65 | 32 | 34 | 23.12 | 0.37 | 0.14 | 0.42 | SAFE |
| 571013 | 2 | 2 | 23.63 | 32 | 31 | 20.17 | 0.31 | 0.14 | 0.33 | SAFE |
| 452068 | 2 | 2 | 24.40 | 41 | 39 | 19.57 | 0.29 | 0.19 | 0.35 | SAFE |
| 130071 | 2 | 2 | 23.76 | 29 | 30 | 21.79 | 0.30 | 0.03 | 0.41 | SAFE |
| 168413 | 2 | 2 | 22.85 | 25 | 29 | 20.63 | 0.31 | 0.05 | 0.39 | SAFE |
| 346910 | 2 | 2 | 23.93 | 34 | 32 | 17.89 | 0.27 | 0.23 | 0.39 | SAFE |
| 83429 | 2 | 2 | 22.94 | 32 | 40 | 19.27 | 0.15 | 0.14 | 0.52 | SAFE |
| 940231 | 2 | 2 | 22.67 | 29 | 38 | 18.70 | 0.25 | 0.51 | 0.43 | SAFE |
| 394594 | 2 | 2 | 21.87 | 82 | 69 | 21.58 | 0.35 | 0.12 | 0.41 | SAFE |
| 863606 | 2 | 2 | 22.69 | 30 | 34 | 18.76 | 0.26 | 0.06 | 0.34 | SAFE |
| 753381 | 2 | 2 | 21.53 | 40 | 39 | 22.35 | 0.22 | 0.06 | 0.42 | SAFE |
| 540023 | 2 | 2 | 21.83 | 40 | 40 | 20.11 | 0.31 | 0.31 | 0.46 | SAFE |
| 118784 | 2 | 2 | 21.91 | 25 | 39 | 20.66 | 0.28 | 0.05 | 0.46 | SAFE |
| 47506 | 2 | 2 | 22.45 | 34 | 38 | 17 | 0.27 | 0.11 | 0.54 | SAFE |
| 499883 | 2 | 2 | 24.51 | 28 | 36 | 22.60 | 0.30 | 0.04 | 0.48 | SAFE |
| 15478 | 2 | 2 | 22.90 | 26 | 35 | 21.38 | 0.21 | 0.26 | 0.43 | SAFE |

TABLE 9

Exemplary Step 1 acute active learning data @ 72 hours post-administration (Group 3)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 23.49 | 21 | 48 | 22 | 0.020 | 0.06 | 0.54 | — |
| 634433 | 2 | 2 | 22.84 | 20 | 67 | 24 | 0.17 | 0.21 | 0.46 | SAFE |
| 52553 | 2 | 2 | 23.50 | 18 | 47 | 25 | 0.23 | 0.04 | 0.32 | SAFE |
| 89422 | 2 | 2 | 23.50 | 22 | 58 | 22 | 0.22 | 0.13 | 0.37 | SAFE |
| 252689 | 2 | 2 | 22.70 | 153 | 128 | 19 | 0.24 | 0.04 | 0.41 | |
| 534368 | 2 | 2 | 22.85 | 27 | 62 | 23 | 0.20 | 0.07 | 0.54 | SAFE |
| 125535 | 2 | 2 | 22.33 | 637 | 613 | 11 | 0.19 | 0.20 | 0.53 | TOXIC |
| 531745 | 2 | 2 | 22.80 | 1440 | 3120 | 38 | 0.16 | 0.07 | 0.66 | TOXIC |
| 711284 | 2 | 2 | 22.64 | 33 | 85 | 22 | 0.23 | 0.22 | 0.42 | SAFE |

TABLE 9-continued

Exemplary Step 1 acute active learning data @ 72 hours post-administration (Group 3)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| 982426 | 2 | 2 | 24.21 | 29 | 54 | 26 | 0.18 | 0.22 | 0.46 | SAFE |
| 122106 | 2 | 2 | 20.87 | 1034 | 1008 | 22 | 0.21 | 0.14 | 0.51 | TOXIC |
| 82284 | 2 | 2 | 24.51 | 24 | 96 | 28 | 0.28 | 0.19 | 0.60 | SAFE |
| 328861 | 2 | 2 | 23.28 | 24 | 94 | 14 | 0.18 | 0.08 | 0.44 | SAFE |
| 432289 | 2 | 2 | 20.30 | 40 | 67 | 20 | 0.24 | 0.08 | 0.33 | SAFE |
| 546096 | 2 | 2 | 24.33 | 22 | 50 | 24 | 0.19 | 0.19 | 0.54 | SAFE |
| 227340 | 2 | 2 | 24.44 | 28 | 80 | 27 | 0.17 | 0.42 | 0.43 | SAFE |
| 111307 | 2 | 2 | 22.13 | 24 | 61 | 29 | 0.15 | 0.27 | 0.38 | SAFE |
| 155024 | 2 | 2 | 23.53 | 22 | 56 | 28 | 0.24 | 0.07 | 0.43 | SAFE |
| 571013 | 2 | 2 | 23.96 | 44 | 54 | 23 | 0.19 | 0.27 | 0.32 | SAFE |
| 452068 | 2 | 2 | 24.92 | 57 | 109 | 22 | 0.20 | 0.02 | 0.49 | SAFE |
| 130071 | 2 | 2 | 23.39 | 66 | 101 | 24 | 0.15 | 0.21 | 0.37 | SAFE |
| 168413 | 2 | 2 | 23.23 | 26 | 68 | 21 | 0.25 | 0.09 | 0.41 | SAFE |
| 346910 | 2 | 2 | 24.70 | 59 | 82 | 24 | 0.22 | 0.132 | 0.46 | SAFE |
| 83429 | 2 | 2 | 23.12 | 43 | 66 | 34 | 0.31 | 0.04 | 0.31 | SAFE |
| 940231 | 2 | 2 | 23.57 | 43 | 103 | 22 | 0.18 | 0.16 | 0.39 | SAFE |
| 394594 | 2 | 2 | 22.67 | 53 | 67 | 20 | 0.22 | 0.21 | 0.31 | SAFE |
| 863606 | 2 | 2 | 23.54 | 19 | 70 | 22 | 0.21 | 0.26 | 0.42 | SAFE |
| 753381 | 2 | 2 | 21.90 | 31 | 195 | 22 | 0.17 | 0.09 | 0.50 | SAFE |
| 540023 | 2 | 2 | 22.36 | 28 | 146 | 21 | 0.23 | 0.19 | 0.44 | SAFE |
| 118784 | 2 | 2 | 22.88 | 21 | 96 | 24 | 0.21 | 0.11 | 0.51 | SAFE |
| 47506 | 2 | 2 | 23.26 | 25 | 47 | 22 | 0.22 | 0.07 | 0.38 | SAFE |
| 499883 | 2 | 2 | 25.38 | 34 | 60 | 14 | 0.24 | 0.00 | 0.38 | SAFE |
| 15478 | 2 | 2 | 23.34 | 24 | 56 | 25 | 0.24 | 0.23 | 0.33 | SAFE |

TABLE 10

Exemplary Step 1 acute active learning data @ 24 hours post-administration (Group 4)

| Experimental Group | No. of mice | 24 hr Survival | Dosing BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 23.89 | 30 | 50 | 18 | 0.32 | 0.16 | 0.56 | — |
| 737341 | 2 | 2 | 23.93 | 49 | 66 | 21 | 0.31 | 0.10 | 0.47 | SAFE |
| 253319 | 2 | 2 | 22.13 | 28 | 43 | 20 | 0.39 | 0.16 | 0.60 | |
| 527126 | 2 | 2 | 22.37 | 40 | 39 | 20 | 0.40 | 0.30 | 0.47 | SAFE |
| 338296 | 2 | 2 | 23.84 | 42 | 45 | 21 | 0.33 | 0.05 | 0.53 | SAFE |
| 204254 | 2 | 2 | 23.43 | 36 | 35 | 20 | 0.36 | 0.05 | 0.41 | SAFE |
| 819987 | 2 | 2 | 23.56 | 39 | 44 | 21 | 0.39 | 0.13 | 0.46 | SAFE |
| 479162 | 2 | 2 | 20.28 | 39 | 58 | 24 | 0.36 | 0.17 | 0.43 | SAFE |
| 351132 | 2 | 2 | 22.96 | 26 | 45 | 22 | 0.38 | 0.07 | 0.61 | SAFE |
| 770912 | 2 | 2 | 23.93 | 28 | 38 | 19 | 0.37 | 0.23 | 0.56 | SAFE |
| 768336 | 2 | 2 | 21.14 | 26 | 37 | 23 | 0.44 | 0.29 | 0.48 | SAFE |
| 606819 | 2 | 2 | 22.32 | 32 | 43 | 23 | 0.37 | 0.08 | 0.62 | SAFE |
| 624628 | 2 | 2 | 21.65 | 33 | 40 | 29 | 0.48 | 0.13 | 0.46 | SAFE |
| 612527 | 2 | 2 | 19.97 | 24 | 51 | 24 | 0.40 | 0.19 | 0.48 | SAFE |
| 928411 | 2 | 2 | 22.13 | 43 | 54 | 20 | 0.38 | 0.10 | 0.62 | SAFE |
| 174113 | 2 | 2 | 21.75 | 28 | 40 | 22 | 0.34 | 0.26 | 0.48 | TOXIC |
| 858171 | 2 | 2 | 21.48 | 79 | 95 | 22 | 0.38 | 0.20 | 0.45 | SAFE |
| 796555 | 2 | 2 | 22.76 | 33 | 46 | 21 | 0.44 | 0.02 | 0.49 | TOXIC |
| 474266 | 2 | 2 | 21.31 | 35 | 47 | 22 | 0.40 | 0.10 | 0.55 | SAFE |
| 242649 | 2 | 2 | 21.06 | 46 | 69 | 24 | 0.29 | 0.20 | 0.47 | SAFE |
| 359800 | 2 | 2 | 23.69 | 47 | 49 | 23 | 0.39 | 0.23 | 0.57 | SAFE |
| 327141 | 2 | 2 | 20.49 | 29 | 43 | 20 | 0.38 | 0.01 | 0.45 | |
| 562229 | 2 | 2 | 20.03 | 44 | 46 | 21 | 0.39 | 0.21 | 0.56 | SAFE |
| 903104 | 2 | 2 | 21.68 | 40 | 64 | 24 | 0.38 | 0.17 | 0.42 | SAFE |
| 774779 | 2 | 2 | 22.05 | 46 | 47 | 21 | 0.36 | 0.15 | 0.41 | SAFE |
| 992725 | 2 | 2 | 22.50 | 29 | 54 | 24 | 0.49 | 0.13 | 0.60 | SAFE |
| 350213 | 2 | 2 | 23.12 | 32 | 41 | 22 | 0.39 | 0.13 | 0.48 | TOXIC |
| 279342 | 2 | 2 | 22.73 | 36 | 53 | 20 | 0.43 | 0.06 | 0.55 | TOXIC |
| 563767 | 2 | 2 | 21.76 | 39 | 41 | 21 | 0.38 | 0.00 | 0.43 | |
| 826204 | 2 | 2 | 21.72 | 28 | 45 | 23 | 0.35 | 0.03 | 0.48 | SAFE |
| 881216 | 2 | 0 | 22.88 | 79 | 86 | 24 | 0.41 | 0.06 | 0.53 | TOXIC |
| 739351 | 2 | 2 | 24.80 | 36 | 43 | 21 | 0.36 | 0.30 | .050 | |
| 874060 | 2 | 2 | 22.54 | 26 | 40 | 19 | 0.40 | 0.31 | 0.46 | SAFE |

TABLE 11

Exemplary Step 1 acute active learning data @ 72 hours post-administration (Group 4)

| Experimental Group | No. of mice | 72 hr Survival | Sac BW (g) | ALT (U/L) | AST (U/L) | BUN (mg/dL) | Serum CREA (mg/dL) | CRP (mg/L) | TBILI (mg/dL) | Train |
|---|---|---|---|---|---|---|---|---|---|---|
| Saline Control | 2 | 2 | 24.00 | 22 | 54 | 27 | 0.23 | 0.02 | 0.57 | — |
| 737341 | 2 | 2 | 24.15 | 66 | 212 | 28 | 0.29 | 0.29 | 1.46 | SAFE |
| 253319 | 2 | 2 | 22.82 | 132 | 143 | 19 | 0.25 | 0.19 | 0.42 | |
| 527126 | 2 | 2 | 22.59 | 81 | 216 | 27 | 0.20 | 0.23 | 0.69 | SAFE |
| 338296 | 2 | 2 | 23.50 | 25 | 75 | 26 | 0.23 | 0.12 | 0.42 | SAFE |
| 204254 | 2 | 2 | 23.09 | 47 | 140 | 23 | 0.22 | 0.08 | 0.49 | SAFE |
| 819987 | 2 | 2 | 23.73 | 46 | 81 | 18 | 0.21 | 0.14 | 0.49 | SAFE |
| 479162 | 2 | 2 | 20.60 | 25 | 59 | 28 | 0.19 | 0.10 | 0.44 | SAFE |
| 351132 | 2 | 2 | 23.25 | 29 | 77 | 29 | 0.23 | 0.08 | 0.44 | SAFE |
| 770912 | 2 | 2 | 23.83 | 63 | 283 | 29 | 0.25 | 0.11 | 0.92 | SAFE |
| 768336 | 2 | 2 | 21.58 | 27 | 67 | 25 | 0.26 | 0.07 | 0.41 | SAFE |
| 606819 | 2 | 2 | 22.83 | 36 | 98 | 23 | 0.22 | 0.00 | 0.70 | SAFE |
| 624628 | 2 | 2 | 21.57 | 43 | 93 | 22 | 0.22 | 0.15 | 0.53 | SAFE |
| 612527 | 2 | 2 | 20.36 | 25 | 72 | 25 | 0.21 | 0.21 | 0.85 | SAFE |
| 928411 | 2 | 2 | 22.18 | 47 | 146 | 23 | 0.23 | 0.11 | 0.98 | SAFE |
| 174113 | 2 | 2 | 21.89 | 207 | 275 | 21 | 0.21 | 0.15 | 0.33 | TOXIC |
| 858171 | 2 | 2 | 22.13 | 82 | 112 | 27 | 0.25 | 0.29 | 0.60 | SAFE |
| 796555 | 2 | 2 | 23.38 | 357 | 371 | 29 | 0.21 | 0.16 | 4.11 | TOXIC |
| 474266 | 2 | 2 | 21.01 | 62 | 143 | 29 | 0.25 | 0.01 | 1.52 | SAFE |
| 242649 | 2 | 2 | 19.45 | 29 | 59 | 26 | 0.3 | 0.00 | 0.56 | SAFE |
| 359800 | 2 | 2 | 23.69 | 76 | 109 | 23 | 0.26 | 0.13 | 0.43 | SAFE |
| 327141 | 2 | 2 | 20.92 | 168 | 337 | 24 | 0.31 | 0.01 | 0.68 | |
| 562229 | 2 | 2 | 20.86 | 26 | 70 | 25 | 0.25 | 0.06 | 0.54 | SAFE |
| 903104 | 2 | 2 | 23.46 | 46 | 73 | 22 | 0.25 | 0.20 | 0.55 | SAFE |
| 774779 | 2 | 2 | 22.41 | 26 | 50 | 25 | 0.26 | 0.09 | 0.49 | SAFE |
| 992725 | 2 | 2 | 23.32 | 26 | 86 | 29 | 0.27 | 0.03 | 0.67 | SAFE |
| 350213 | 2 | 2 | 23.63 | 586 | 511 | 24 | 0.28 | 0.11 | 0.78 | TOXIC |
| 279342 | 2 | 2 | 22.07 | 35 | 67 | 24 | 0.32 | 0.14 | 0.47 | TOXIC |
| 563767 | 2 | 2 | 21.27 | 147 | 187 | 22 | 0.27 | 0.03 | 0.58 | |
| 826204 | 2 | 2 | 22.29 | 25 | 55 | 29 | 0.25 | 0.03 | 0.48 | SAFE |
| 881216 | 2 | 0 | dead | — | — | — | — | — | — | TOXIC |
| 739351 | 2 | 2 | 24.41 | 135 | 168 | 20 | 0.18 | 0.07 | 0.51 | |
| 874060 | 2 | 2 | 22.80 | 27 | 53 | 28 | 0.20 | 0.11 | 0.53 | SAFE |

Figure 9:
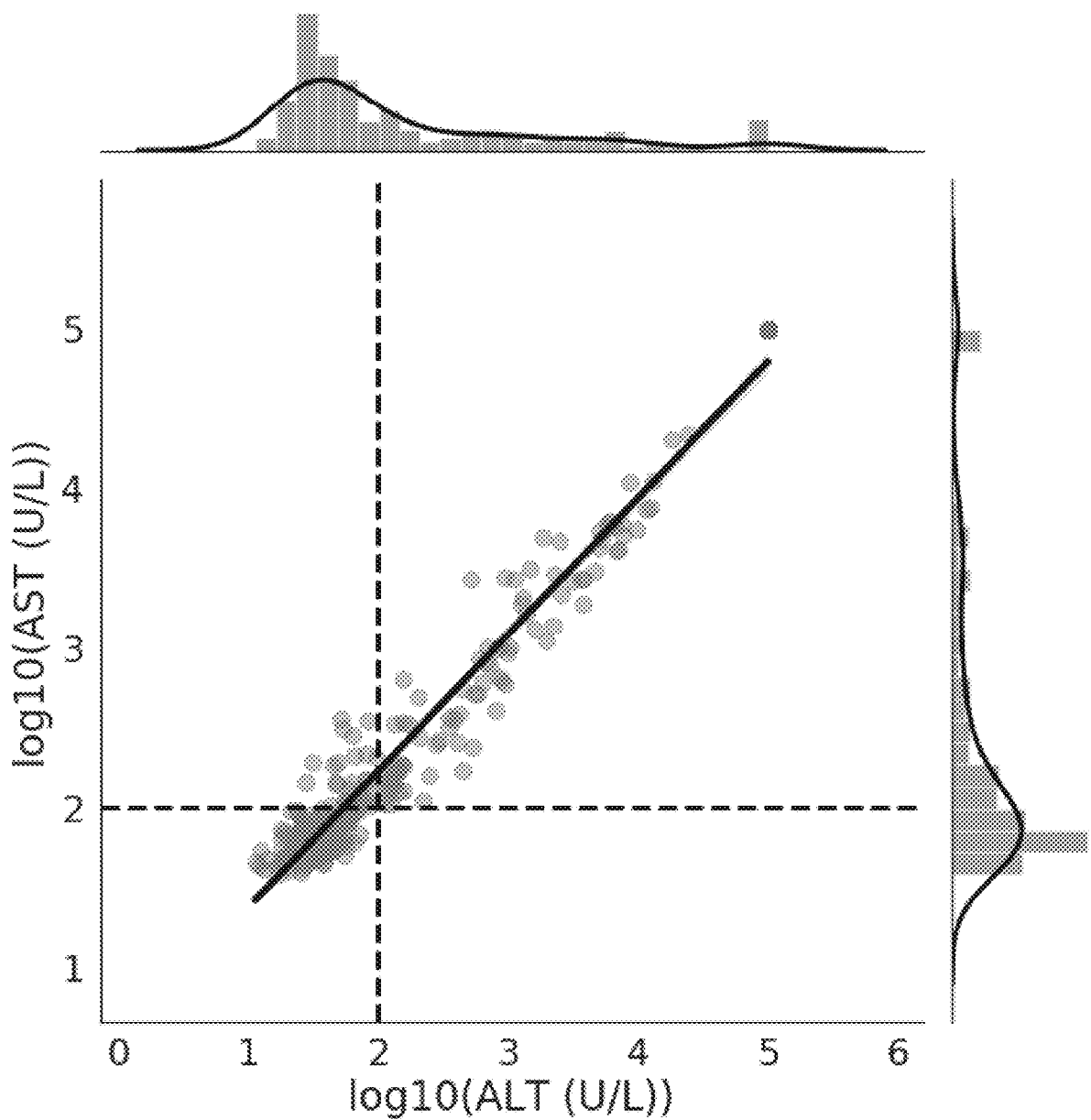
FIG. 9 shows enrichment of safe OBMs; Creyon survey OBMs were 69% safe compared to 10-25% for random screening.

Surprisingly, data from the Step 1 active learning demonstrated an unexpected enrichment of safe OBMs. In particular, after only 1 active learning round Creyon Step 1 OBMs were already 69% safe compared to 10-25% for random screening (FIG. 9). FIG. 9 is an exemplary plot of measured log 10 ALT (U/L) vs measured log 10 AST (U/L) (ALT and AST are both biomarkers for hepatotoxicity) and demonstrates a clustering of Creyon OBMs below 100 U/L toxicity level for both ALT and AST.

Figure 10A:
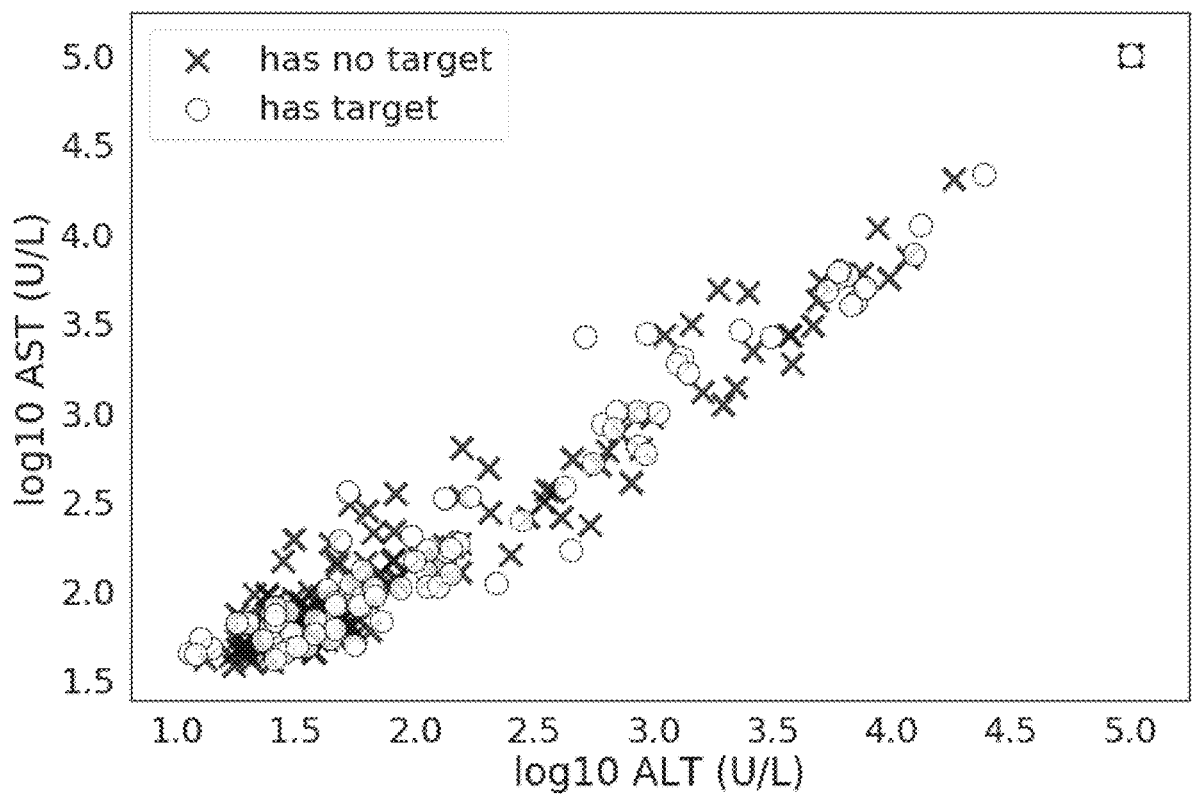
FIG. 10A: Creyon platform is target agnostic.

These data also demonstrate that the provided methods are target agnostic and perform equally well regardless of whether the sequence "has a target" or has no known target. These results confirm the separability of RNaseH-mediated off-target driven toxicity versus the far more common OBM sequence-interaction driven toxicities (FIG. 10A).

IV.E. Example 6—Active Learning Step—Step 2—Systemic In Vivo Tolerability Survey of 128 OBMs in Mice to Refine Predictive Regression Model of Systemic Tolerability This example details a second active learning survey step evaluated in vivo over a 15-day period of time to further refine the Step 1 regression model built in Example 5. In particular, the Step 2 active learning surveyed 128 OBMs (16 nucleotide long ASOs with fixed 3-10-3 LNA gapmer chemical scaffold) in vivo to evaluate the safety and toxicity of OBMs engineered by the methods described herein.

Male C57BL/6 mice aged 11-12 weeks were maintained as described in Example 3.

Total Study Design was 15 days. On Day −1 (before the study started) body weight was recorded and mice were randomized into groups of 3 mice each per treatment (OBM or control). Observations and read-outs included body weight, urine volume and collection, blood collection, serum and urinary analysis and kidney and liver collection. Exemplary nephrotoxicity assays included, but were not limited to urinary KIM-1, Serum Cystatin-c (CysC), Serum Creatinine and BUN. Exemplary hepatotoxicity assays included, but were not limited to serum ALT, AST, GLDH, and CCK-18. Exemplary immunotoxicity assays included, but not limited to cytokine assay(s), complete blood count (CBC) and C-reactive protein (CRP). Mean bodyweight was recorded on Days 1, 5 and 15. CBC analysis was performed as described in Example 3.

Groups received subcutaneous injections of an OBM at a dose of 75 mg/kg on Day 1 and Day 4, for a total of 2 doses. Urinary kidney injury molecule (KIM-1), a sensitive quantitative biomarker for early detection of kidney tubular injury and Serum Cystatin-c (CysC) were measured at +24 hours after each dose. At +72 hours after each dose and on Day 15, blood was collected and Liver Function Tests (LFT) and Kidney Function Tests (KFT) performed. Immunotoxicity was also measured at and included levels of CRP and CBC analysis.

Liver function tests (LFT) included but were not limited to serum alanine transaminase (ALT), aspartate transaminase (AST), and total bilirubin (TBIL) measurements. Kidney function tests (KFT) included but were not limited to serum blood urea nitrogen (BUN) and creatinine measurements. Final Study Design was as follows: Day 1: Dose 1; Day 2 (+24 hours): collect urine KIM-1; Day 3 (+72 hours): collect blood LFT, KFT, CRP; Day 4: Dose 2; Day 5(+24 hours): collect urine KIM-1; Day 6 (+72 hours): collect blood LFT, KFT, CRP; Day 15: study termination, collect blood, LFT, KFT, CRP, CBC).

On Day 15 animals were sacrificed and wet tissue weight measured for liver, kidney and spleen.

Exemplary liver function test markers are provided in Table 12. Exemplary dosing, liver and kidney function results for the Step 2 of active learning are provided in Table 13, 14, 15, 16, 17, 18, 19, 20, 21, 22, 23 and 24.

TABLE 12

Exemplary liver function test markers

| | Parameters | Full Name | Associated with |
|---|---|---|---|
| Liver enzymes | ALT | Alanine Aminotransferase | Hepatocytic damage/necrosis, Hepatitis |
| | AST | Aspartate Aminotransferase | Liver, Skeletal, cardiac, muscle, kidney, brain |
| | ALPI | Alkaline Phosphatase | Liver, Bone Parathyroid and Intestinal diseases, |
| | GGT | Gamma(γ)-Glutamyl Transferase | Liver, Heart, Kidney, spleen, pancreas & prostate |
| | LDI | Lactate Dehydrogenase | Liver, cardiac muscle, skeletal muscle, kidneys and erythrocytes. |
| | SDH | Sorbitol dehydrogenase | Liver damage and diabetic |
| | 5-NUCLEOTIDASE | 5-nucleotidase | Hepatocytic damage/necrosis, Hepatitis, autoimmune, toxic, |
| | AST/ALT | Aspartate Aminotransferase: Alanine Aminotransferase | AST/ALT >2 in Chronic Liver Disease AST/ALT <1 acute hepatitis/injury |
| | GLDH | Glutamate Dehydrogenase | Elevated blood serum GLDH levels indicate liver damage; hepatocytic damage/necrosis, hepatitis |
| Excretory | TBI | Total Bilirubin | Liver, Hemolytic, Hematological and metabolic disorders |
| | AMM | Ammonia | Severe liver disorders such as cirrhosis, hepatitis |
| Protein synthesis | TP | Total Protein | Liver, kidney, Bone marrow, metabolic or nutritional disorders |
| | ALB | Albumin | Liver, Kidney |
| | GLOB | Globulin | Liver, kidney, Bone marrow, metabolic or nutritional disorders |
| | A/G | Albumin: Globulin | Liver, kidney, Bone marrow, metabolic or nutritional disorders |
| | PT | Prothrombin time | Liver, Vitamin K deficiency, etc. |
| | APTT | Activated partial Thromboplastin Time | Liver, Vitamin K deficiency, etc. |
| Other | LA | Lactate | Liver, Oxygen deficiency (Lactic Acidosis) and CKD |
| | BA | Bile Acid | Liver (biliary Damage) |

TABLE 13

Exemplary Step 2 active learning data - Day 2 and Day 5 Kidney Function Tests (Batch 1)

| Experimental Group | Day 2 Cystatin-C (pg/mL) | Day 2 Kim-1 (pg/mL) | Day 2 BUN (mg/dL) | Day 2 Urinary CREA (mg/dL) | Day 5 Cystatin-C (pg/mL) | Day 5 Kim-2 (pg/mL) | Day 5 BUN (mg/dL) | Day 5 Urinary CREA (mg/dL) | Train |
|---|---|---|---|---|---|---|---|---|---|
| Saline Control | 255462.08 | 7793.96 | 19.93 | 40.87 | 187638.55 | 4149.40 | 25.38 | 48.25 | — |
| 993154 | 192026.49 | 7830.94 | 18.01 | 28.75 | 658672.2 | 28128.14 | 19.23 | 42.33 | SAFE |
| 519154 | 189631.35 | 4678.7 | 17.36 | 31.26 | 240923.49 | 3446.08 | 17.15 | 35.29 | TOXIC |
| 307838 | 90024.75 | 1835.83 | 20.00 | 13.35 | 3582004.4 | 34486.33 | — | 37.27 | TOXIC |
| 981380 | 396195.3 | 3001.78 | 23.03 | 19.80 | 1484192.27 | 4528.12 | 18.82 | 24.59 | SAFE |
| 738296 | 144452.01 | 4451.52 | 26.76 | 31.17 | 849962.6 | 4494.07 | 20.33 | 30.11 | TOXIC |
| 118475 | 1482656.2 | 16131.02 | — | 66.62 | dead | dead | dead | dead | TOXIC |
| 632914 | 1246698.73 | 13293.51 | 23.23 | 61.70 | 743517.9 | 7692.62 | 20.33 | 43.71 | SAFE |
| 49609 | 279878.31 | 7807.29 | 17.81 | 37.49 | 796861.73 | 6515.94 | 18.76 | 47.24 | SAFE |
| 746474 | 1077150.6 | 7712.34 | 22.84 | 29.31 | 2566182 | 6307.02 | 17.21 | 30.35 | SAFE |
| 27749 | 402707.51 | 5835.45 | 24.44 | 40.38 | 733460.07 | 8281.23 | 21.54 | 48.19 | TOXIC |
| 304426 | 251218.98 | 11087.38 | 23.85 | 56.23 | 283963.67 | 8027.87 | 23.40 | 43.86 | SAFE |
| 8566 | 431443.27 | 6674.63 | 21.34 | 34.47 | 2524740 | 9207.19 | 17.75 | 51.68 | |
| 443170 | 420977.27 | 8817.58 | 26.82 | 32.37 | 768525.53 | 9507.25 | 24.47 | 53.73 | |
| 873027 | 608318.33 | 27414.64 | 22.74 | 64.34 | 819431.13 | 5962.51 | 22.90 | 41.22 | SAFE |
| 603813 | 698476.27 | 7712.7 | 28.87 | 29.13 | 2376542 | 12043.52 | 27.61 | 62.85 | |
| 741913 | 402417.73 | 7506.3 | 22.05 | 57.06 | 226565.21 | 5093.2 | 19.72 | 35.24 | SAFE |
| 238639 | 234007.09 | 6426.75 | 25.13 | 58.44 | 130095.58 | 4344.61 | 27.67 | 32.35 | TOXIC |

TABLE 13-continued

Exemplary Step 2 active learning data - Day 2 and Day 5 Kidney Function Tests (Batch 1)

| Experimental Group | Day 2 Cystatin-C (pg/mL) | Day 2 Kim-1 (pg/mL) | Day 2 BUN (mg/dL) | Day 2 Urinary CREA (mg/dL) | Day 5 Cystatin-C (pg/mL) | Day 5 Kim-2 (pg/mL) | Day 5 BUN (mg/dL) | Day 5 Urinary CREA (mg/dL) | Train |
|---|---|---|---|---|---|---|---|---|---|
| 747776 | 1140249.53 | 5583.39 | 22.30 | 37.33 | 748175.67 | 5070.13 | 20.31 | 34.80 | TOXIC |
| 361474 | 203201.11 | 7258.62 | 19.64 | 45.31 | 173761.99 | 3248.32 | 18.33 | 30.93 | SAFE |
| 866975 | 128721.43 | 5108.91 | 17.02 | 24.45 | 353662.83 | 7749.99 | 19.43 | 57.76 | SAFE |
| 791282 | 562295.2 | 6095.44 | 21.24 | 39.77 | 1181170.4 | 4342.65 | 20.30 | 19.86 | SAFE |
| 966623 | 283640.04 | 4982.54 | 20.59 | 31.66 | 215827.13 | 6827.96 | 22.89 | 35.24 | SAFE |
| 70031 | 329156.66 | 6907.98 | 22.56 | 39.37 | 137302.65 | 3077.73 | 23.07 | 29.72 | SAFE |
| 716261 | 445078.75 | 5779.41 | 21.73 | 40.33 | 714255 | 5755.44 | 25.43 | 32.28 | |
| 194812 | 729966.13 | 9249.9 | 17.50 | 62.06 | 1072891.67 | 5862.55 | 21.56 | 27.05 | TOXIC |
| 521162 | 670745.67 | 4155.83 | 19.32 | 35.46 | 1167084.47 | 3350.72 | 32.09 | 42.70 | TOXIC |
| 777802 | 967269 | 9917.29 | 18.48 | 49.37 | 940655.93 | 9979.83 | 22.68 | 22.80 | TOXIC |
| 638908 | 340284.32 | 4605.96 | 17.22 | 47.89 | 101544.75 | 4562.02 | 23.46 | 23.11 | TOXIC |
| 325463 | 592462.33 | 11980.83 | 17.51 | 78.44 | 655642.4 | 4126.94 | 21.92 | 21.48 | SAFE |
| 208852 | 270231.05 | 5203.92 | 15.46 | 55.41 | 2823207.53 | 8152.25 | 23.17 | 30.31 | SAFE |
| 942598 | 269945.68 | 3924.39 | 15.93 | 26.02 | 1185968 | 3674.47 | 17.18 | 26.21 | SAFE |
| 832389 | 433373.67 | 10817.88 | — | 40.55 | dead | dead | dead | dead | TOXIC |

TABLE 14

Exemplary Step 2 active learning data - Day 4 and Day 7 Liver Function Tests (Batch 1)

| Experimental Group | Day 1 BW (g) | Day 5 BW (g) | Day 4 ALT (U/L) | Day 4 AST (U/L) | Day 4 GLDH (U/L) | Day 7 ALT (U/L) | Day 7 AST (U/L) | Day 7 GLDH (U/L) | Train |
|---|---|---|---|---|---|---|---|---|---|
| Saline Control | 25.67 | 25.77 | 48.12 | 73.36 | 26.36 | 40.45 | 84.64 | 27.58 | — |
| 993154 | 26.09 | 25.65 | 81.55 | 83.73 | 40.49 | 36.34 | 74.26 | 22.05 | SAFE |
| 519154 | 25.43 | 24.69 | 44.31 | 63.86 | 17.53 | 59.29 | 93.6 | 34.59 | TOXIC |
| 307838 | 54.54 | 22.16 | 540.75 | 859.16 | 311.87 | 6289.33 | 7910.27 | 2152.43 | TOXIC |
| 981380 | 24.88 | 24.25 | 29.63 | 59.62 | 19.44 | 36.84 | 99.83 | 28.55 | SAFE |
| 738296 | 25.05 | 25.14 | 31.05 | 60.08 | 17.89 | 135.51 | 311.73 | 209.37 | TOXIC |
| 118475 | 25.04 | dead | −10.48 | −26.55 | 381.52 | dead | dead | dead | TOXIC |
| 632914 | 25.05 | 25.48 | 52.01 | 82.63 | 32.96 | 41.36 | 85.19 | 29.07 | SAFE |
| 49609 | 25.07 | 25.29 | 55.61 | 113.73 | 24.18 | 23.31 | 62.86 | 15.78 | SAFE |
| 746474 | 25.15 | 24.46 | 38.87 | 57.02 | 21.41 | 35.26 | 67.67 | 86.66 | SAFE |
| 27749 | 25.45 | 25.22 | 42.35 | 72.19 | 23.57 | 3122.48 | 2582.87 | 908.36 | TOXIC |
| 304426 | 25.62 | 24.86 | 62.8 | 69.66 | 18.64 | 33 | 71.59 | 20.8 | SAFE |
| 8566 | 25.48 | 25.20 | 34.44 | 65.98 | 20.11 | 68.43 | 101.78 | 28.72 | |
| 443170 | 25.31 | 25.19 | 95.38 | 68.36 | 16.26 | 62.4 | 108.59 | 27.42 | |
| 873027 | 26.06 | 25.79 | 42.39 | 59.23 | 16.26 | 28.43 | 56.67 | 14.56 | SAFE |
| 603813 | 25.43 | 25.27 | 77.38 | 82.61 | 22.66 | 68.57 | 95.01 | 38.49 | |
| 741913 | 25.41 | 25.25 | 61.39 | 70.54 | 24.57 | 27.93 | 63.43 | 18.42 | SAFE |
| 238639 | 25.40 | 24.93 | 33.01 | 69.24 | 17.06 | 1001.08 | 917.46 | 529.3 | TOXIC |
| 747776 | 25.70 | 25.55 | 55.17 | 77.96 | 29.44 | 1089.15 | 1472.11 | 894.48 | TOXIC |
| 361474 | 25.41 | 25.30 | 45.17 | 59.94 | 18.69 | 28.37 | 57.74 | 20.36 | SAFE |
| 866975 | 24.96 | 25.38 | 41.38 | 71.86 | 14.1 | 43.05 | 60.95 | 14.87 | SAFE |
| 791282 | 25.21 | 25.22 | 42.24 | 64.36 | 16.26 | 20.34 | 39.69 | 15.54 | SAFE |
| 966623 | 26.09 | 25.53 | 86.04 | 70.4 | 39.77 | 35.63 | 56.29 | 15.09 | SAFE |
| 70031 | 25.48 | 25.52 | 47.5 | 66.31 | 28.69 | 24.39 | 61.01 | 13.43 | SAFE |
| 716261 | 24.82 | 25.78 | 61.83 | 90.23 | 31.46 | 99.62 | 94.03 | 23.68 | |
| 194812 | 25.62 | 25.37 | 50.95 | 77.03 | 27.14 | 107.2 | 147.63 | 124.63 | TOXIC |
| 521162 | 24.85 | 25.69 | 50.13 | 80.9 | 19.33 | 758 | 1194.95 | 343.39 | TOXIC |
| 777802 | 26.07 | 25.73 | 71.53 | 269.49 | 33.26 | 551.29 | 534.96 | 201.01 | TOXIC |
| 638908 | 25.62 | 25.59 | 39.02 | 83.66 | 19.99 | 364.7 | 248.1 | 112.33 | TOXIC |
| 325463 | 25.47 | 25.37 | 41.27 | 75.81 | 12.07 | 26.52 | 56.09 | 15.59 | SAFE |
| 208852 | 25.21 | 25.16 | 44.29 | 88.18 | 23.68 | 1757.65 | 1180.11 | 780.33 | SAFE |
| 942598 | 25.00 | 25.68 | 55.75 | 86.09 | 29.72 | 110.11 | 123.69 | 58.13 | SAFE |
| 832389 | 25.47 | dead | −5.89 | −22.18 | 255.43 | dead | dead | dead | TOXIC |

TABLE 15

Exemplary Step 2 active learning data - Day 2 and Day 5 Kidney Function Tests (Batch 2)

| Experimental Group | Day 2 Cystatin-C (pg/mL) | Day 2 Kim-1 (pg/mL) | Day 2 Urinary CREA (mg/dL) | Day 5 Cystatin-C (pg/mL) | Day 5 Kim-2 (pg/mL) | Day 5 Urinary CREA (mg/dL) | Train |
|---|---|---|---|---|---|---|---|
| Saline Control | 164523.75 | 5891.07 | 50.76 | 155519.11 | 2858.10 | 33.93 | — |
| 881203 | 513349.17 | 3768.06 | 34.16 | 2465814.60 | 2518.90 | 22.98 | TOXIC |
| 944156 | 926560.15 | 4080.82 | 34.24 | 524836.78 | 4716.98 | 28.29 | SAFE |
| 200150 | 373915.10 | 4543.03 | 28.24 | 1283689.91 | 4243.06 | 29.82 | SAFE |
| 938067 | 221015.85 | 3734.25 | 32.59 | 396179.46 | 3017.35 | 34.14 | TOXIC |
| 118948 | 287970.73 | 3020.57 | 19.60 | 796090.05 | 2766.67 | 20.09 | SAFE |
| 781955 | 408805.46 | 5736.60 | 38.87 | 1218251.46 | 2605.33 | 27.46 | SAFE |
| 665820 | 155475.10 | 1970.27 | 17.92 | 326068.44 | 1484.82 | 16.92 | SAFE |
| 72753 | 2321213.15 | 4521.09 | 9.60 | 3635846.93 | 24328.63 | 35.41 | TOXIC |
| 401556 | 504298.44 | 3640.51 | 25.75 | 173386.37 | 2035.10 | 23.48 | SAFE |
| 618163 | 107968.18 | 2965.15 | 23.58 | 83980.52 | 1372.94 | 20.77 | SAFE |
| 726259 | 155966.27 | 4973.45 | 26.59 | 614002.23 | 6711.40 | 52.48 | TOXIC |
| 570833 | 3066491.53 | 9313.84 | 44.10 | 9057371.21 | 5780.62 | 38.75 | TOXIC |
| 383196 | 501629.22 | 31544.32 | 64.33 | 274785.41 | 5629.36 | 22.32 | |
| 179548 | 388085.55 | 7628.96 | 53.68 | 525792.76 | 2884.60 | 29.17 | SAFE |
| 653495 | 916817.58 | 5324.17 | 59.58 | dead | dead | dead | TOXIC |
| 797688 | 941107.85 | 7831.34 | 52.99 | 1790584.81 | 14992.44 | 36.16 | TOXIC |
| 711766 | 350755.60 | 4242.10 | 44.23 | 210373.74 | 1333.62 | 22.28 | |
| 879866 | 988432.11 | 8953.57 | 53.17 | 782667.84 | 3995.45 | 34.81 | SAFE |
| 814738 | 615962.98 | 6663.63 | 42.30 | 727026.70 | 5108.78 | 34.85 | SAFE |
| 145937 | 739960.44 | 10314.10 | 70.19 | 486368.88 | 6058.86 | 34.88 | |
| 154401 | 662691.30 | 6723.92 | 41.27 | 386301.61 | 2843.94 | 27.54 | SAFE |
| 586734 | 510217.59 | 8889.21 | 50.52 | dead | dead | dead | TOXIC |
| 538044 | 486609.09 | 6791.24 | 62.72 | 1374166.92 | 9649.63 | 44.19 | TOXIC |
| 168576 | 775128.37 | 21559.68 | 78.32 | 1205692.89 | 8512.70 | 24.29 | |
| 734191 | 659826.41 | 8733.07 | 47.29 | 269004.47 | 2389.31 | 21.60 | SAFE |
| 771379 | 401119.56 | 5806.31 | 45.46 | 419092.23 | 18698.92 | 34.78 | TOXIC |
| 199181 | 2146503.90 | 9133.44 | 38.53 | 6280147.11 | 12158.54 | 31.74 | TOXIC |
| 375707 | 539522.43 | 10127.82 | 54.62 | 465346.57 | 2041.34 | 16.35 | SAFE |
| 156549 | 571628.08 | 6091.03 | 25.57 | 754430.60 | 3008.57 | 24.86 | TOXIC |
| 408449 | 501630.31 | 4521.32 | 25.99 | 697090.24 | 4576.08 | 37.09 | SAFE |
| 81243 | 824610.24 | 5787.19 | 23.66 | 906035.76 | 5245.13 | 29.79 | TOXIC |
| 541841 | 446072.24 | 15812.45 | 25.13 | 848295.10 | 3833.39 | 28.05 | TOXIC |

TABLE 16

Exemplary Step 2 active learning data - Day 4 and Day 7 Liver Function Tests (Batch 2)

| Experimental Group | Day 1 BW (g) | Day 5 BW (g) | Day 15 BW (g) | Day 4 ALT (U/L) | Day 4 AST (U/L) | Day 4 Serum CREA (mg/dL) | Day 7 ALT (U/L) | Day 7 AST (U/L) | Day 7 Serum CREA (mg/dL) | Train |
|---|---|---|---|---|---|---|---|---|---|---|
| Saline Control | 25.79 | 26.54 | 27.56 | 79.89 | 95.13 | 0.49 | 45.56 | 86.61 | 0.36 | — |
| 881203 | 27.08 | 26.92 | 27.43 | 91.66 | 100.29 | 0.48 | 2156.24 | 1273.83 | 0.41 | TOXIC |
| 944156 | 26.55 | 27.66 | 29.50 | 87.92 | 72.29 | 0.38 | 73.91 | 114.01 | 0.37 | SAFE |
| 200150 | 26.30 | 26.47 | 27.86 | 38.19 | 73.74 | 0.52 | 39.80 | 71.02 | 0.46 | SAFE |
| 938067 | 26.16 | 26.26 | 28.65 | 42.18 | 85.69 | 0.43 | 165.36 | 188.39 | 0.33 | TOXIC |
| 118948 | 26.84 | 27.22 | 28.95 | 83.59 | 88.81 | 0.41 | 27.48 | 63.57 | 0.40 | SAFE |
| 781955 | 26.09 | 26.14 | 27.90 | 66.73 | 90.20 | 0.40 | 53.11 | 76.82 | 0.35 | SAFE |
| 665820 | 25.86 | 26.37 | 27.62 | 28.13 | 67.32 | 0.42 | 190.21 | 243.09 | 0.30 | SAFE |
| 72753 | 26.63 | 25.53 | 18.45 | 648.92 | 1592.60 | 0.45 | 2640.12 | 5824.85 | 0.31 | TOXIC |
| 401556 | 25.98 | 26.39 | 27.54 | 33.44 | 74.92 | 0.46 | 28.39 | 61.90 | 0.38 | SAFE |
| 618163 | 26.05 | 26.52 | 27.70 | 61.66 | 95.64 | 0.41 | 39.94 | 67.86 | 0.35 | SAFE |
| 726259 | 25.49 | 26.13 | 27.02 | 73.40 | 115.40 | 0.46 | 161.32 | 192.56 | 0.41 | TOXIC |
| 570833 | 25.24 | 25.31 | 27.18 | 379.14 | 528.10 | 0.41 | 2146.71 | 2057.92 | 0.38 | TOXIC |
| 383196 | 26.34 | 27.03 | 29.25 | 49.72 | 77.70 | 0.42 | 229.21 | 154.16 | 0.35 | |
| 179548 | 26.01 | 26.24 | 28.04 | 83.79 | 85.68 | 0.36 | 51.21 | 83.11 | 0.25 | SAFE |
| 653495 | 26.10 | dead | dead | 13056.50 | 10151.86 | 0.50 | dead | dead | dead | TOXIC |
| 797688 | 26.13 | 25.66 | 24.80 | 88.94 | 171.14 | 0.37 | 848.33 | 930.82 | 0.35 | TOXIC |
| 711766 | 26.46 | 26.73 | 26.76 | 52.18 | 66.76 | 0.34 | 22.18 | 51.33 | 0.26 | |
| 879866 | 25.93 | 26.78 | 28.08 | 151.18 | 141.92 | 0.29 | 20.13 | 51.76 | 0.28 | SAFE |
| 814738 | 26.37 | 26.27 | 27.84 | 53.18 | 65.59 | 0.39 | 17.54 | 65.94 | 0.33 | SAFE |
| 145937 | 26.70 | 27.10 | 27.75 | 60.68 | 76.12 | 0.34 | 39.85 | 85.79 | 0.28 | |
| 154401 | 26.88 | 26.63 | 19.46 | 97.57 | 70.30 | 0.34 | 17.79 | 47.17 | 0.26 | SAFE |
| 586734 | 27.02 | dead | dead | 12614.00 | 11094.75 | 0.38 | dead | dead | dead | TOXIC |

TABLE 16-continued

Exemplary Step 2 active learning data - Day 4 and Day 7 Liver Function Tests (Batch 2)

| Experimental Group | Day 1 BW (g) | Day 5 BW (g) | Day 15 BW (g) | Day 4 ALT (U/L) | Day 4 AST (U/L) | Day 4 Serum CREA (mg/dL) | Day 7 ALT (U/L) | Day 7 AST (U/L) | Day 7 Serum CREA (mg/dL) | Train |
|---|---|---|---|---|---|---|---|---|---|---|
| 538044 | 26.49 | 25.19 | 24.06 | 227.56 | 249.13 | 0.38 | 8805.96 | 11128.89 | 0.38 | TOXIC |
| 168576 | 26.67 | 27.19 | 27.67 | 66.89 | 73.41 | 0.36 | 858.59 | 1109.81 | 0.34 | |
| 734191 | 25.79 | 27.01 | 27.89 | 37.67 | 70.54 | 0.33 | 14.15 | 89.72 | 0.30 | SAFE |
| 771379 | 26.59 | 27.28 | 27.76 | 41.79 | 83.73 | 0.38 | 438.49 | 179.35 | 0.32 | TOXIC |
| 199181 | 26.60 | 26.50 | 21.76 | 91.98 | 105.62 | 0.28 | 1192.75 | 1103.13 | 0.31 | TOXIC |
| 375707 | 26.56 | 27.27 | 27.75 | 29.75 | 64.37 | 0.31 | 26.17 | 58.00 | 0.33 | SAFE |
| 156549 | 26.26 | 26.02 | 27.11 | 57.90 | 114.87 | 0.23 | 192.50 | 271.25 | 0.29 | TOXIC |
| 408449 | 25.71 | 26.66 | 27.12 | 66.29 | 86.17 | 0.26 | 29.33 | 51.55 | 0.33 | SAFE |
| 81243 | 26.32 | 26.62 | 27.45 | 49.98 | 69.15 | 0.31 | 242.40 | 125.26 | 0.31 | TOXIC |
| 541841 | 26.30 | 25.58 | dead | 45.66 | 72.36 | 0.38 | 4467.70 | 3085.91 | 0.35 | TOXIC |

TABLE 17

Exemplary Step 2 active learning data - Day 2 and Day 5 Kidney Function Tests (Batch 3)

| Experimental Group | Day 2 Cystatin-C (pg/mL) | Day 2 Kim-1 (pg/mL) | Day 2 Urinary CREA (mg/dL) | Day 5 Cystatin-C (pg/mL) | Day 5 Kim-2 (pg/mL) | Day 5 Urinary CREA (mg/dL) | Train |
|---|---|---|---|---|---|---|---|
| Saline Control | 238758.21 | 4972.13 | 60.67 | 286055.06 | 4834.46 | 45.14 | — |
| 732514 | 260896.80 | 3152.16 | 30.98 | 721692.13 | 2008.02 | 18.85 | SAFE |
| 87575 | 930943.53 | 51460.84 | 65.82 | 643520.53 | 5124.79 | 18.43 | SAFE |
| 48388 | 71011.45 | 3025.90 | 14.65 | 295531.18 | 7376.62 | 40.96 | SAFE |
| 500494 | 3292786.53 | 12757.90 | 57.12 | 3172471.47 | 4561.93 | 27.22 | SAFE |
| 883656 | 1295204.47 | 4761.91 | 38.17 | 6886940.00 | 4629.12 | 23.62 | TOXIC |
| 539919 | 539761.40 | 3308.32 | 20.51 | 2121778.00 | 3688.30 | 20.34 | SAFE |
| 98818 | 742534.07 | 3877.60 | 33.31 | 2130835.60 | 3699.91 | 30.91 | SAFE |
| 764312 | 6607410.67 | 15077.94 | 99.66 | 5480822.67 | 6547.28 | 43.74 | SAFE |
| 731722 | 534844.53 | 12698.21 | 106.25 | 381681.00 | 3454.84 | 30.64 | SAFE |
| 485590 | 491913.47 | 4867.55 | 35.71 | 9277260.00 | 63019.26 | 20.50 | TOXIC |
| 834577 | 2589888.50 | 15723.40 | 54.93 | 3644999.33 | 11960.59 | 28.92 | SAFE |
| 801559 | 2225262.90 | 36067.46 | 56.27 | 3459124.00 | 18109.12 | 41.40 | SAFE |
| 352118 | 476729.57 | 3539.09 | 31.83 | 2801964.67 | 6223.87 | 41.14 | SAFE |
| 575833 | 1087197.00 | 4219.34 | 19.41 | 2996238.00 | 9697.15 | 28.81 | TOXIC |
| 984070 | 208308.75 | 1631.89 | 26.03 | 617289.20 | 2310.41 | 22.68 | SAFE |
| 519970 | 3902555.33 | 18998.46 | 79.66 | 5256790.67 | 20385.51 | 28.42 | TOXIC |
| 672471 | 2066235.07 | 1217.53 | 15.95 | 6554424.00 | 16476.40 | 32.83 | TOXIC |
| 373230 | 1201103.70 | 1344.78 | 23.49 | 3942965.87 | 3395.30 | 19.42 | |
| 567116 | 1391476.33 | 4536.76 | 29.21 | 2615064.00 | 5950.67 | 25.97 | SAFE |
| 68461 | 104880.24 | 530.06 | 18.06 | 957770.87 | 7405.26 | 47.00 | TOXIC |
| 474831 | 242401.90 | 3384.06 | 44.05 | 386873.22 | 17524.30 | 39.19 | SAFE |
| 171217 | 166365.04 | 761.76 | 37.08 | 119366.11 | 3491.39 | 24.61 | SAFE |
| 972466 | 460135.27 | 3907.07 | 48.39 | 461563.67 | 4585.89 | 40.75 | SAFE |
| 34573 | 1048882.53 | 1950.72 | 31.25 | 8721028.00 | 37359.63 | 77.46 | TOXIC |
| 948669 | 2829127.07 | 5079.42 | 48.23 | 5268642.00 | 3022.56 | 18.20 | TOXIC |
| 611192 | 1749360.47 | 7123.79 | 32.82 | 8997380.00 | 19629.60 | 26.35 | TOXIC |
| 39449 | 827785.60 | 9878.52 | 22.91 | 8302236.00 | 57203.99 | 16.96 | TOXIC |
| 825340 | 353552.16 | 3526.44 | 55.56 | 664796.27 | 2324.53 | 22.25 | SAFE |
| 205789 | 334009.20 | 1264.12 | 19.25 | 4294692.00 | 5868.36 | 50.07 | SAFE |

TABLE 18

Exemplary Step 2 active learning data - Day 4 and Day 7 Liver Function Tests (Batch 3)

| Experimental Group | Day 1 BW (g) | Day 5 BW (g) | Day 15 BW (g) | Day 4 ALT (U/L) | Day 4 AST (U/L) | Day 4 Serum CREA (mg/dL) | Day 7 ALT (U/L) | Day 7 AST (U/L) | Day 7 Serum CREA (mg/dL) | Train |
|---|---|---|---|---|---|---|---|---|---|---|
| Saline Control | 28.27 | 27.88 | 28.46 | 89.68 | 85.13 | 0.29 | 24.38 | 50.10 | 0.17 | — |
| 732514 | 26.94 | 26.63 | 27.42 | 116.83 | 82.94 | 0.31 | 48.69 | 58.05 | 0.16 | SAFE |
| 87575 | 25.36 | 26.15 | 26.88 | 116.81 | 105.04 | 0.24 | 19.32 | 50.44 | 0.21 | SAFE |

TABLE 18-continued

Exemplary Step 2 active learning data - Day 4 and Day 7 Liver Function Tests (Batch 3)

| Experimental Group | Day 1 BW (g) | Day 5 BW (g) | Day 15 BW (g) | Day 4 ALT (U/L) | Day 4 AST (U/L) | Day 4 Serum CREA (mg/dL) | Day 7 ALT (U/L) | Day 7 AST (U/L) | Day 7 Serum CREA (mg/dL) | Train |
|---|---|---|---|---|---|---|---|---|---|---|
| 48388 | 24.44 | 27.15 | 27.69 | 41.22 | 78.33 | 0.27 | 64.88 | 133.95 | 0.16 | SAFE |
| 500494 | 26.80 | 27.36 | 27.63 | 43.70 | 70.67 | 0.33 | 35.18 | 58.38 | 0.17 | SAFE |
| 883656 | 26.83 | 26.01 | 25.66 | 33.29 | 69.62 | 0.40 | 614.80 | 464.21 | 0.22 | TOXIC |
| 539919 | 25.63 | 26.02 | 27.05 | 66.60 | 77.45 | 0.37 | 23.88 | 57.25 | 0.21 | SAFE |
| 98818 | 27.34 | 26.18 | 26.98 | 30.04 | 60.25 | 0.34 | 19.86 | 69.33 | 0.20 | SAFE |
| 764312 | 23.44 | 25.53 | 26.05 | 46.89 | 73.13 | 0.33 | 46.74 | 79.41 | 0.20 | SAFE |
| 731722 | 22.62 | 25.27 | 25.55 | 34.71 | 70.54 | 0.29 | 55.49 | 62.57 | 0.16 | SAFE |
| 485590 | 26.44 | 23.64 | dead | 722.26 | 797.26 | 0.35 | dead | dead | dead | TOXIC |
| 834577 | 26.95 | 26.39 | 26.65 | 108.40 | 81.36 | 0.37 | 38.27 | 61.02 | 0.25 | SAFE |
| 801559 | 25.62 | 27.40 | 29.58 | 48.76 | 117.78 | 0.27 | 78.81 | 99.11 | 0.17 | SAFE |
| 352118 | 22.82 | 24.41 | 25.75 | 36.54 | 69.88 | 0.34 | 35.93 | 65.76 | 0.19 | SAFE |
| 575833 | 27.68 | 28.12 | 27.99 | 59.69 | 121.75 | 0.30 | 321.63 | 425.31 | 0.14 | TOXIC |
| 984070 | 26.15 | 24.71 | 26.39 | 53.39 | 74.64 | 0.42 | 19.41 | 41.87 | 0.24 | SAFE |
| 519970 | 26.48 | 25.26 | 21.45 | 166.13 | 278.04 | 0.34 | 720.35 | 988.92 | 0.19 | TOXIC |
| 672471 | 25.37 | 24.15 | dead | 1393.29 | 1383.50 | 0.36 | 12356.55 | 7554.34 | dead | TOXIC |
| 373230 | 26.36 | 25.34 | 26.75 | 46.03 | 104.14 | 0.33 | 101.97 | 155.83 | 0.14 | |
| 567116 | 26.87 | 26.23 | 27.02 | 82.56 | 106.90 | 0.31 | 12.81 | 54.92 | 0.16 | SAFE |
| 68461 | 27.07 | 25.95 | 25.04 | 42.28 | 85.52 | 0.32 | 819.18 | 1326.06 | 0.17 | TOXIC |
| 474831 | 25.34 | 22.80 | 25.70 | 42.77 | 90.33 | 0.36 | 13.29 | 42.16 | 0.13 | SAFE |
| 171217 | 24.79 | 24.64 | 25.93 | 42.55 | 71.73 | 0.27 | 23.00 | 52.86 | 0.20 | SAFE |
| 972466 | 25.99 | 25.12 | 25.89 | 64.41 | 83.01 | 0.29 | 19.18 | 44.62 | 0.18 | SAFE |
| 34573 | 26.79 | 23.41 | dead | 231.08 | 278.68 | 0.24 | 13507.02 | 10074.54 | 0.11 | TOXIC |
| 948669 | 26.32 | 25.60 | 27.10 | 207.10 | 214.74 | 0.27 | 12705.36 | 11758.45 | 0.26 | TOXIC |
| 611192 | 25.73 | 23.47 | dead | 1701.45 | 2965.18 | 0.24 | dead | dead | dead | TOXIC |
| 39449 | 27.37 | 26.66 | 27.70 | 3207.82 | 3861.79 | 0.27 | 2675.44 | 1250.84 | 0.28 | TOXIC |
| 825340 | 25.16 | 22.93 | 25.24 | 82.87 | 64.20 | 0.25 | 42.47 | 84.70 | 0.24 | SAFE |
| 205789 | 22.85 | 25.26 | 26.07 | 47.12 | 84.58 | 0.26 | 26.50 | 76.53 | 0.30 | SAFE |

TABLE 19

Exemplary Step 2 active learning data - Day 2 and Day 5 Kidney Function Tests (Batch 4)

| Experimental Group | Day 2 Cystatin-C (pg/mL) | Day 2 Kim-1 (pg/mL) | Day 2 Urinary CREA (mg/dL) | Day 5 Cystatin-C (pg/mL) | Day 5 Kim-2 (pg/mL) | Day 5 Urinary CREA (mg/dL) | Train |
|---|---|---|---|---|---|---|---|
| Saline Control | 260869.60 | 5955.54 | 63.12 | 88643.05 | 1209.21 | 22.89 | — |
| 403138 | 474242.20 | 5437.96 | 40.06 | 744446.00 | 2365.97 | 17.10 | TOXIC |
| 960688 | 1360967.13 | 11972.50 | 47.22 | 2058346.20 | 4883.93 | 20.41 | TOXIC |
| 209901 | 350910.13 | 4517.79 | 26.79 | 401606.00 | 2858.54 | 19.00 | TOXIC |
| 271224 | 2377972.67 | 3661.58 | 18.06 | 3297180.00 | 4791.12 | 22.06 | TOXIC |
| 424753 | 474861.53 | 5285.38 | 36.61 | 676750.53 | 4272.16 | 26.48 | |
| 347410 | 529883.40 | 4000.57 | 22.66 | 456599.76 | 1347.10 | 7.04 | TOXIC |
| 915019 | 991440.20 | 6447.03 | 42.34 | 4458235.00 | 7695.06 | 40.97 | TOXIC |
| 860444 | 2524640.90 | 25547.29 | 42.87 | 1466631.87 | 20894.73 | 51.44 | TOXIC |
| 770772 | 879996.20 | 1658.19 | 22.17 | 4324970.00 | 84304.21 | 19.74 | TOXIC |
| 347738 | 1506716.00 | 5589.58 | 32.37 | 1455349.70 | 2824.25 | 20.28 | SAFE |
| 605401 | 1897051.33 | 23989.88 | 42.30 | 453195.25 | 2502.17 | 29.24 | TOXIC |
| 870257 | 331480.27 | 3451.99 | 25.71 | 1971347.33 | 4502.89 | 20.88 | TOXIC |
| 571578 | 1757100.30 | 5557.19 | 38.73 | 2239937.00 | 4524.36 | 25.63 | TOXIC |
| 571326 | 901524.00 | 6608.68 | 62.65 | 220513.96 | 2612.63 | 28.97 | TOXIC |
| 537377 | 2407175.80 | 12955.24 | 45.50 | 4359576.00 | 6515.82 | 30.65 | TOXIC |
| 804768 | 161897.70 | 2055.13 | 24.52 | 4129850.00 | 4991.68 | 30.25 | TOXIC |
| 402461 | 860701.20 | 4986.68 | 34.29 | 855144.33 | 2783.29 | 18.30 | SAFE |
| 23699 | 206248.77 | 3669.04 | 23.17 | 396875.75 | 2873.74 | 25.98 | TOXIC |
| 868203 | 526293.00 | 1095.35 | 15.53 | 1733312.73 | 4426.87 | 29.61 | TOXIC |

TABLE 20

Exemplary Step 2 active learning data - Day 4 and Day 7 Liver Function Tests (Batch 4)

| Experimental Group | Day 1 BW (g) | Day 4 BW (g) | Day 15 BW (g) | Day 4 ALT (U/L) | Day 4 AST (U/L) | Day 4 Serum CREA (mg/dL) | Day 7 ALT (U/L) | Day 7 AST (U/L) | Day 7 Serum CREA (mg/dL) | Train |
|---|---|---|---|---|---|---|---|---|---|---|
| Saline Control | 25.15 | 26.51 | 27.28 | 68.09 | 191.06 | 0.31 | 31.75 | 76.14 | 0.29 | — |
| 403138 | 24.19 | 25.87 | dead | 115.46 | 159.06 | 0.36 | 19036.92 | 18438.13 | 0.09 | TOXIC |
| 960688 | 26.77 | 25.64 | 20.84 | 869.06 | 995.14 | 0.34 | 6268.70 | 6570.31 | 0.27 | TOXIC |
| 209901 | 25.48 | 26.56 | 26.70 | 47.91 | 80.98 | 0.43 | 99.25 | 183.09 | 0.35 | TOXIC |
| 271224 | 26.57 | 26.74 | 25.19 | 56.22 | 89.67 | 0.33 | 618.77 | 242.15 | 0.32 | TOXIC |
| 424753 | 25.36 | 25.94 | 27.65 | 50.18 | 72.29 | 0.31 | 40.10 | 76.72 | 0.30 | |
| 347410 | 23.68 | 24.63 | 24.02 | 3839.66 | 3669.03 | 0.23 | 7750.81 | 6080.74 | 0.24 | TOXIC |
| 915019 | 25.58 | 25.09 | 22.00 | 215.38 | 222.66 | 0.29 | 3770.16 | 2825.47 | 0.28 | TOXIC |
| 860444 | 24.81 | 23.18 | dead | 7210.53 | 6699.77 | 0.26 | 3795.62 | 7201.27 | 0.24 | TOXIC |
| 770772 | 24.80 | 22.37 | dead | 3100.36 | 5076.09 | 0.20 | dead | dead | dead | TOXIC |
| 347738 | 24.95 | 23.44 | 26.44 | 21.77 | 63.26 | 0.23 | 35.98 | 67.19 | 0.31 | SAFE |
| 605401 | 25.59 | 25.62 | 28.04 | 57.43 | 75.12 | 0.27 | 132.78 | 172.74 | 0.33 | TOXIC |
| 870257 | 26.26 | 26.61 | dead | 100.86 | 108.20 | 0.25 | 10341.86 | 6818.89 | 0.24 | TOXIC |
| 571578 | 23.47 | 25.67 | 26.10 | 31.87 | 66.00 | 0.31 | 29.62 | 67.61 | 0.32 | TOXIC |
| 571326 | 26.61 | 25.81 | 27.40 | 75.34 | 75.84 | 0.26 | 1026.84 | 1188.33 | 0.30 | TOXIC |
| 537377 | 25.52 | 24.11 | 23.63 | 473.17 | 378.37 | 0.23 | 9498.20 | 5176.81 | 0.17 | TOXIC |
| 804768 | 25.79 | 25.85 | 26.51 | 1090.28 | 1651.16 | 0.30 | 24081.78 | 18576.76 | 0.25 | TOXIC |
| 402461 | 25.91 | 25.67 | 25.75 | 49.24 | 64.94 | 0.24 | 40.35 | 71.41 | 0.29 | SAFE |
| 23699 | 25.42 | 25.96 | 25.96 | 87.37 | 106.31 | 0.24 | 2119.88 | 3021.48 | 0.33 | TOXIC |
| 868203 | 24.37 | 25.76 | 25.07 | 70.10 | 71.91 | 0.26 | 91.13 | 137.30 | 0.33 | TOXIC |

TABLE 21

Exemplary Step 2 active learning data - Terminal Liver Function Tests - Day 15 (Batch 1)

| Experimental Group | No. of mice | 15 Day Survival | ALT (U/L) | AST (U/L) | Serum CREA (mg/dL) | Liver (mg) | Kidney (mg) | Spleen (mg) | Train |
|---|---|---|---|---|---|---|---|---|---|
| Saline Control | 3 | 3 | 20.12 | 49.58 | 0.3 | 1489.67 | 335.33 | 88.67 | — |
| 993154 | 3 | 3 | 34.38 | 153.25 | 0.38 | 1514.33 | 336 | 104 | SAFE |
| 519154 | 3 | 2 | 823.93 | 380.33 | 0.38 | 1681 | 298.67 | 87.33 | TOXIC |
| 307838 | 3 | 1 | 2325.38 | 2337.89 | 0.35 | 1716 | 349 | 67 | TOXIC |
| 981380 | 3 | 3 | 57.21 | 118.46 | 0.40 | 1266.33 | 289.33 | 84 | SAFE |
| 738296 | 3 | 3 | 409.00 | 716.95 | 0.45 | 1192.33 | 316 | 160 | TOXIC |
| 118475 | 3 | 0 | — | — | — | — | — | — | TOXIC |
| 632914 | 3 | 2 | 42.77 | 76.28 | 0.41 | 1893.5 | 332.5 | 123 | SAFE |
| 49609 | 3 | 3 | 43.14 | 68.99 | 0.38 | 1754.67 | 311.67 | 133 | SAFE |
| 746474 | 3 | 3 | 88.73 | 117.71 | 0.36 | 1337.33 | 274 | 74.67 | SAFE |
| 27749 | 3 | 3 | 1356.56 | 510.07 | 0.39 | 1389.67 | 329.67 | 70 | TOXIC |
| 304426 | 3 | 3 | 19.23 | 56.05 | 0.34 | 1244.67 | 324.33 | 69.67 | SAFE |
| 8566 | 3 | 3 | 125.58 | 98.68 | 0.33 | 2222.33 | 318.33 | 83.67 | |
| 443170 | 3 | 3 | 120.48 | 128.25 | 0.50 | 1748.67 | 284.67 | 100 | |
| 873027 | 3 | 3 | 12.91 | 40.84 | 0.50 | 1326 | 324.67 | 87 | SAFE |
| 603813 | 3 | 3 | 134.10 | 135.31 | 0.49 | 1958 | 328.33 | 92 | |
| 741913 | 3 | 3 | 26.84 | 54.02 | 0.46 | 1517 | 333.33 | 87.67 | SAFE |
| 238639 | 3 | 3 | 2637.60 | 1479.03 | 0.36 | 1604 | 283.67 | 70.67 | TOXIC |
| 747776 | 3 | 3 | 1899.20 | 1960.89 | 0.45 | 2555.67 | 329 | 135.67 | TOXIC |
| 361474 | 3 | 3 | 29.14 | 112.54 | 0.33 | 1412 | 326.33 | 90.67 | SAFE |
| 866975 | 3 | 3 | 43.58 | 64.29 | 0.47 | 1335.33 | 308 | 77.67 | SAFE |
| 791282 | 3 | 3 | 20.52 | 57.96 | 0.46 | 1286 | 305 | 84.67 | SAFE |
| 966623 | 3 | 3 | 41.62 | 66.71 | 0.53 | 1554.33 | 311.33 | 96.33 | SAFE |
| 70031 | 3 | 3 | 39.52 | 65.25 | 0.34 | 1264.33 | 301.33 | 76.33 | SAFE |
| 716261 | 3 | 3 | 166.81 | 200.09 | 0.44 | 1399.67 | 336.67 | 86 | |
| 194812 | 3 | 3 | 264.44 | 231.87 | 0.39 | 1580.67 | 345.67 | 98 | TOXIC |
| 521162 | 3 | 2 | 2461.99 | 1351.90 | 0.40 | 1494 | 318 | 122.5 | TOXIC |
| 777802 | 3 | 3 | 1807.53 | 948.72 | 0.43 | 1818.5 | 300.67 | 85.33 | TOXIC |
| 638908 | 3 | 3 | 1500.47 | 1385.34 | 0.39 | 1870 | 326 | 78.33 | TOXIC |
| 325463 | 3 | 3 | 21.30 | 66.14 | 0.40 | 1132.33 | 308 | 84.67 | SAFE |
| 208852 | 3 | 3 | 98.61 | 108.59 | 0.37 | 1699 | 335.67 | 114.33 | SAFE |
| 942598 | 3 | 3 | 72.41 | 95.09 | 0.45 | 1663.33 | 295.33 | 74 | SAFE |
| 832389 | 3 | 0 | — | — | — | — | — | — | TOXIC |

TABLE 22

Exemplary Step 2 active learning data - Terminal Liver Function Tests - Day 15 (Batch 2)

| Experimental Group | No. of mice | 15 Day Survival | ALT (U/L) | AST (U/L) | Serum CREA (mg/dL) | Liver (mg) | Kidney (mg) | Spleen (mg) | Train |
|---|---|---|---|---|---|---|---|---|---|
| Saline Control | 3 | 3 | 35.93 | 71.64 | 0.38 | 1491.7 | 345.3 | 78.0 | — |
| 881203 | 3 | 3 | 2925.14 | 1346.58 | 0.43 | 2655.7 | 344.3 | 81.0 | TOXIC |
| 944156 | 3 | 3 | 62.09 | 101.02 | 0.42 | 2002.7 | 365.7 | 125.3 | SAFE |
| 200150 | 3 | 3 | 35.69 | 69.49 | 0.33 | 1687.3 | 321.0 | 87.7 | SAFE |
| 938067 | 3 | 3 | 341.23 | 389.88 | 0.36 | 2303.3 | 347.0 | 89.3 | TOXIC |
| 118948 | 3 | 3 | 36.76 | 75.73 | 0.34 | 1723.0 | 372.0 | 95.7 | SAFE |
| 781955 | 3 | 3 | 51.96 | 72.7 | 0.39 | 1531.3 | 325.3 | 95.3 | SAFE |
| 665820 | 3 | 3 | 60.64 | 88.72 | 0.36 | 1750.3 | 334.3 | 104.3 | SAFE |
| 72753 | 3 | 2 | 2799.56 | 3004.34 | 0.22 | 1258.5 | 292.0 | 41.5 | TOXIC |
| 401556 | 3 | 3 | 32.26 | 63.30 | 0.38 | 1441.0 | 348.0 | 85.3 | SAFE |
| 618163 | 3 | 3 | 63.96 | 130.81 | 0.34 | 1361.3 | 331.0 | 92.0 | SAFE |
| 726259 | 3 | 3 | 245.66 | 151.21 | 0.25 | 1801.7 | 340.3 | 89.7 | TOXIC |
| 570833 | 3 | 3 | 972.56 | 1006.99 | 0.36 | 1494.3 | 332.0 | 102.0 | TOXIC |
| 383196 | 3 | 3 | 118.96 | 150.72 | 0.35 | 2194.0 | 341.3 | 92.3 | |
| 179548 | 3 | 3 | 38.85 | 74.22 | 0.24 | 1769.3 | 323.7 | 103.3 | SAFE |
| 653495 | 3 | 0 | — | — | — | — | — | — | TOXIC |
| 797688 | 3 | 3 | 2151.42 | 1433.10 | 0.37 | 1281.3 | 312.0 | 88.3 | TOXIC |
| 711766 | 3 | 3 | 101.37 | 96.02 | 0.31 | 1455.0 | 305.0 | 76.7 | |
| 879866 | 3 | 3 | 39.05 | 82.8 | 0.38 | 1495.7 | 335.3 | 95.7 | SAFE |
| 814738 | 3 | 3 | 31.99 | 77.48 | 0.39 | 1528.7 | 315.7 | 88.7 | SAFE |
| 145937 | 3 | 3 | 195.60 | 246.49 | 0.34 | 1372.7 | 352.0 | 92.3 | |
| 154401 | 3 | 3 | 28.70 | 139.15 | 0.45 | 840.0 | 302.3 | 39.3 | SAFE |
| 586734 | 3 | 0 | — | — | — | — | — | — | TOXIC |
| 538044 | 3 | 3 | 1746.59 | 1474.30 | 0.23 | 1659.0 | 304.7 | 66.0 | TOXIC |
| 168576 | 3 | 3 | 102.45 | 99.40 | 0.25 | 1941.3 | 352.7 | 90.0 | |
| 734191 | 3 | 3 | 28.96 | 61.13 | 0.33 | 1658.7 | 336.3 | 111.3 | SAFE |
| 771379 | 3 | 3 | 2102.53 | 858.08 | 0.32 | 1386.3 | 343.0 | 98.0 | TOXIC |
| 199181 | 3 | 3 | 14610.40 | 13284.01 | 0.33 | 828.3 | 322.0 | 68.0 | TOXIC |
| 375707 | 3 | 3 | 24.96 | 69.77 | 0.31 | 1372.7 | 351.0 | 91.3 | SAFE |
| 156549 | 3 | 3 | 782.80 | 629.52 | 0.31 | 1797.3 | 316.0 | 107.7 | TOXIC |
| 408449 | 3 | 3 | 49.42 | 74.7 | 0.38 | 1291.3 | 306.0 | 81.3 | SAFE |
| 81243 | 3 | 3 | 1292.98 | 549.23 | 0.30 | 1991.0 | 309.0 | 80.0 | TOXIC |
| 541841 | 3 | 0 | — | — | — | — | — | — | TOXIC |

TABLE 23

Exemplary Step 2 active learning data - Terminal Liver Function Tests - Day 15 (Batch 3)

| Experimental Group | No. of mice | 15 Day Survival | ALT (U/L) | AST (U/L) | Serum CREA (mg/dL) | Liver (mg) | Kidney (mg) | Spleen (mg) | Train |
|---|---|---|---|---|---|---|---|---|---|
| Saline Control | 3 | 3 | 19.59 | 51.52 | 0.27 | 1410.7 | 332.0 | 87.0 | — |
| 732514 | 3 | 3 | 83.94 | 96.40 | 0.14 | 1665.3 | 293.3 | 125.7 | SAFE |
| 87575 | 3 | 3 | 42.81 | 82.57 | 0.24 | 1459.7 | 309.0 | 90.7 | SAFE |
| 48388 | 3 | 3 | 70.01 | 138.09 | 0.21 | 5058.3 | 341.3 | 360.3 | SAFE |
| 500494 | 3 | 3 | 93.21 | 119.9 | 0.25 | 1602.3 | 333.3 | 100.0 | SAFE |
| 883656 | 3 | 3 | 4009.14 | 1691.82 | 0.19 | 2107.0 | 326.3 | 117.7 | TOXIC |
| 539919 | 3 | 3 | 49.33 | 75.18 | 0.23 | 1620.3 | 306.0 | 77.0 | SAFE |
| 98818 | 3 | 3 | 23.11 | 55.40 | 0.18 | 1368.3 | 325.0 | 76.7 | SAFE |
| 764312 | 3 | 3 | 14.73 | 43.70 | .013 | 1339.0 | 294.3 | 91.0 | SAFE |
| 731722 | 3 | 3 | 42.32 | 60.11 | 0.15 | 1437.3 | 299.3 | 79.0 | SAFE |
| 485590 | 3 | 0 | — | — | — | — | — | — | TOXIC |
| 834577 | 3 | 3 | 23.69 | 58.11 | 0.17 | 1435.7 | 309.3 | 111.3 | SAFE |
| 801559 | 3 | 2 | 81.34 | 117 | 0.26 | 1713.5 | 353.5 | 101.0 | SAFE |
| 352118 | 3 | 3 | 57.47 | 70.56 | 0.21 | 1442.3 | 303.0 | 78.3 | SAFE |
| 575833 | 3 | 3 | 1253.74 | 2114.96 | 0.23 | 2405.7 | 331.3 | 99.7 | TOXIC |
| 984070 | 3 | 3 | 36.55 | 46.21 | 0.20 | 1304.3 | 296.3 | 71.0 | SAFE |
| 519970 | 3 | 3 | 3400.58 | 3000.28 | 0.11 | 1036.0 | 299.7 | 99.3 | TOXIC |
| 672471 | 3 | 0 | — | — | — | — | — | — | TOXIC |
| 373230 | 3 | 3 | 140.45 | 177.27 | 0.133 | 1657.3 | 306.3 | 91.3 | |
| 567116 | 3 | 3 | 34.13 | 65.01 | 0.16 | 1477.0 | 309.0 | 86.0 | SAFE |
| 68461 | 3 | 3 | 3281.26 | 2678.82 | 0.14 | 1655.3 | 308.0 | 85.0 | TOXIC |
| 474831 | 3 | 3 | 27.66 | 47.89 | 0.14 | 1292.0 | 275.7 | 71.0 | SAFE |
| 171217 | 3 | 3 | 57.78 | 101.16 | 0.20 | 1395.0 | 281.7 | 78.7 | SAFE |
| 972466 | 3 | 3 | 13.14 | 42.11 | 0.08 | 1356.0 | 285.3 | 70.3 | SAFE |
| 34573 | 3 | 0 | — | — | — | — | — | — | TOXIC |
| 948669 | 3 | 3 | 1884.40 | 1411.11 | 0.13 | 2374.7 | 316.3 | 106.3 | TOXIC |

TABLE 23-continued

Exemplary Step 2 active learning data - Terminal Liver Function Tests - Day 15 (Batch 3)

| Experimental Group | No. of mice | 15 Day Survival | ALT (U/L) | AST (U/L) | Serum CREA (mg/dL) | Liver (mg) | Kidney (mg) | Spleen (mg) | Train |
|---|---|---|---|---|---|---|---|---|---|
| 611192 | 3 | 0 | — | — | — | — | — | — | TOXIC |
| 39449 | 3 | 3 | 1225.90 | 878.65 | 0.17 | 2136.7 | 380.3 | 95.7 | TOXIC |
| 825340 | 3 | 3 | 91.59 | 162.19 | 0.19 | 1464.0 | 292.0 | 88.7 | SAFE |
| 205789 | 3 | 3 | 20.45 | 72.43 | 0.21 | 1263.0 | 300.7 | 81.0 | SAFE |

TABLE 24

Exemplary Step 2 active learning data - Terminal Liver Function Tests - Day 15 (Batch 4)

| Experimental Group | No. of mice | 15 Day Survival | ALT (U/L) | AST (U/L) | Serum CREA (mg/dL) | Liver (mg) | Kidney (mg) | Spleen (mg) | Train |
|---|---|---|---|---|---|---|---|---|---|
| Saline Control | 3 | 3 | 44.70 | 89.77 | 0.34 | 1342.00 | 345.33 | 84.00 | — |
| 403138 | 3 | 0 | — | — | — | — | — | — | TOXIC |
| 960688 | 3 | 3 | 3055.82 | 3310.02 | 0.20 | 1016.33 | 285.67 | 55.33 | TOXIC |
| 209901 | 3 | 3 | 844.15 | 601.84 | 0.33 | 1803.33 | 296.67 | 107.67 | TOXIC |
| 271224 | 3 | 3 | 5861.45 | 2691.55 | 0.23 | 1827.67 | 297.00 | 89.00 | TOXIC |
| 424753 | 3 | 3 | 142.04 | 210.18 | 0.33 | 1936.67 | 343.00 | 118.33 | |
| 347410 | 3 | 3 | 766.64 | 815.30 | 0.20 | 1215.33 | 318.67 | 104.67 | TOXIC |
| 915019 | 3 | 3 | 2861.24 | 2268.85 | 0.20 | 1766.67 | 294.00 | 83.00 | TOXIC |
| 860444 | 3 | 0 | — | — | — | — | — | — | TOXIC |
| 770772 | 3 | 0 | — | — | — | — | — | — | TOXIC |
| 347738 | 3 | 3 | 45.39 | 88.50 | 0.28 | 1551.00 | 301.33 | 91.00 | SAFE |
| 605401 | 3 | 3 | 468.45 | 486.82 | 0.27 | 3560.67 | 338.00 | 81.67 | TOXIC |
| 870257 | 3 | 0 | — | — | — | — | — | — | TOXIC |
| 571578 | 3 | 3 | 871.96 | 484.64 | 0.22 | 1574.33 | 289.00 | 97.33 | TOXIC |
| 571326 | 3 | 3 | 324.71 | 295.28 | 0.24 | 1312.00 | 346.67 | 101.67 | TOXIC |
| 537377 | 3 | 3 | 1167.79 | 701.29 | 0.34 | 1494.33 | 292.67 | 90.33 | TOXIC |
| 804768 | 3 | 2 | 2820.05 | 2265.31 | 0.35 | 2647.00 | 317.50 | 85.00 | TOXIC |
| 402461 | 3 | 3 | 58.96 | 92.70 | 0.21 | 1336.67 | 297.33 | 77.00 | SAFE |
| 23699 | 3 | 3 | 311.93 | 358.85 | 0.26 | 1543.67 | 336.33 | 89.67 | TOXIC |
| 868203 | 3 | 3 | 1263.76 | 946.59 | 0.24 | 1699.00 | 287.33 | 76.67 | TOXIC |

Figure 10B:
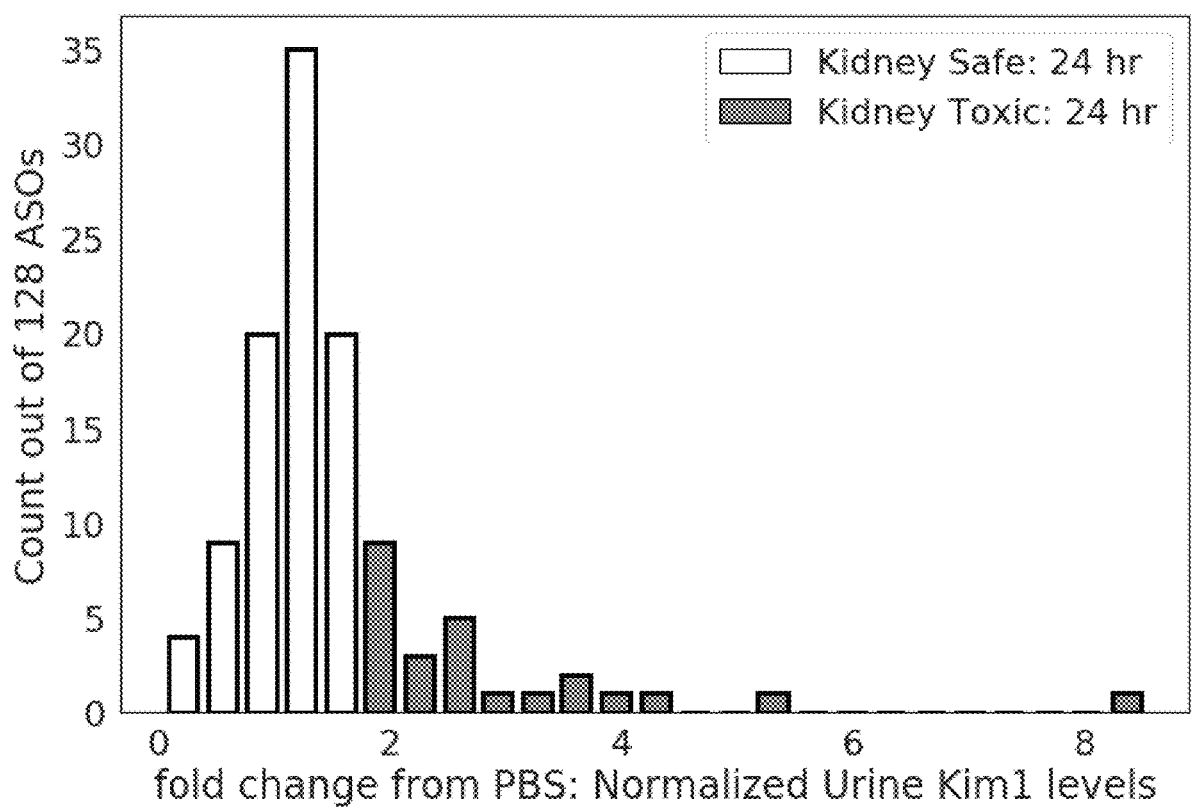
FIG. 10B is an exemplary depiction of Urinary Kim1 concentration of mice at 24 hours after dose 1 (75 mg/kg), normalized to urinary creatinine concentration, and plotted as fold change to PBS treated (median over 3 animals). Fold change of over 2 is potentially kidney toxic.
Figure 11:
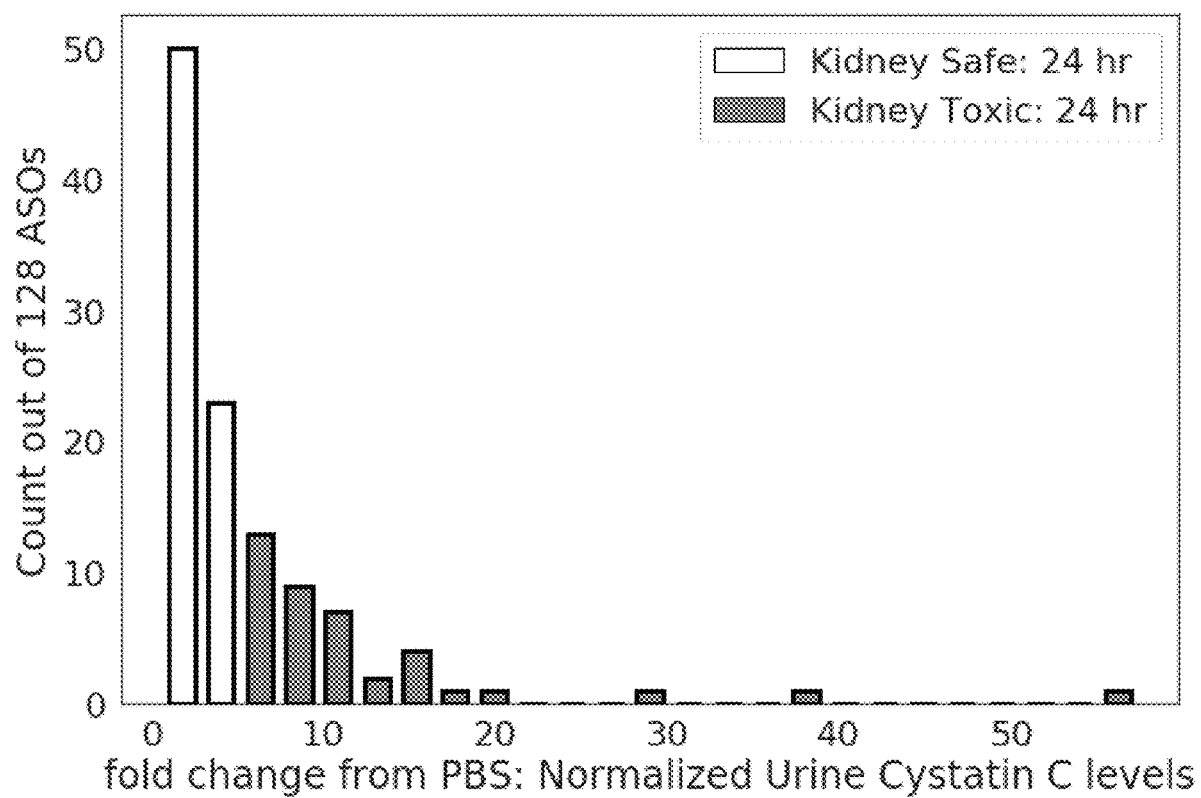
FIG. 11 is an exemplary depiction of Urinary Cystatin C concentration of mice at 24 hours after dose 1 (75 mg/kg), normalized to urinary creatinine concentration, and plotted as fold change to PBS treated (median over 3 animals).

The Step 2 active learning data were used to further refine the Step 1 regression model of hepatotoxicity described in Example 6 to include kidney toxicity. As part of the model refinement, urinary Kim-1 concentration at 24 hour after dose 1 (75 mg/kg) was normalized to urinary creatinine concentration, and plotted as fold change to PBS treated (median over 3 animals) where fold change of over 2 is potentially kidney toxic (FIG. 10B). Additionally, urinary cystatin-c concentration at 24 hour after dose 1 (75 mg/kg) was normalized to urinary creatinine concentration and plotted as fold change to PBS treated (median over 3 animals) (FIG. 11).

IV.F. Example 7—Second Active Learning Step of 48 Platform-Engineered OBMs: Acute In Vitro Cytotoxicity Analysis of OBMs in Human Cell Lines to Refine Predictive Model of Tolerability and Validate Cytotoxicity This example details an active learning survey step of engineered OBMs interrogated in highly predictive in vitro assays to analyze cytotoxicity driven OBM induced pathologies.

The Step 1 in vivo regression model that was developed with the in vivo mouse data described above was used to engineer 48 additional OBMs (16 nucleotide long ASOs with fixed 3-10-3 LNA gapmer chemical scaffold) for testing in an in vitro cytotoxicity active learning step.

Engineered OBMs were then tested in a human hepatocyte carcinoma cell line (HepG2) for various measures of cell viability and cell death in a series of experiments with similar culture conditions and varying cell densities.

Several types of cell death were assayed including apoptosis, necroptosis and pyroptosis. Apoptosis is programmed cell death leading to cell shrinkage, membrane blebbing, chromatin condensation, and DNA fragmentation. Causes of apoptosis include loss of growth signals, presence of cellular stressors, detection of intracellular events that may compromise the whole organism (including DNA replication errors and misfolded proteins) induced by caspases.

Necroptosis presents as different from apoptosis in morphology. Cells undergoing necroptosis exhibit mitochondrial membrane damage, cell swelling, vacuolization, and membrane rupture. Pyroptosis is an inflammatory form of lytic cell death most frequently associated with intracellular pathogens, and is part of the antimicrobial response. Pyroptosis destroys integrity of cell membranes by punching pores through them.

A POSITA is familiar with standard cell viability and cell death assays, any of which can be used with the provided methods. Cell viability assays included, but are not limited to, Alamar Blue (measures metabolic activity of cell by reducing resazurin to resorufin), MTT (MTT is reduced to formazan), MT (MT substrate is reduced in a viable cell which then binds with the NanoLuc luciferase to generate a signal), MitoView (measures cell viability by its ability to accumulate in active mitochondria), CellTiter-Fluor Cell Viability Assay (a Gly-Phe-AFC peptide that enters the cells and is cleaved to produce the fluorescent AFC), and Calcein AM (non-fluorescent membrane permeable compound; cytoplasmic esterases convert to green fluorescence retained in cells with intact plasma membrane). Cell death assays included, but are not limited to various caspase assays, Annexin V (which measures phosphatidylserine exposure on outer cell membranes during apoptosis in a calcium dependent manner), CellTox (cyanine dye excluded from viable cells but binds DNA of dead cells, enhancing the fluorescent properties), Propidium Iodide (membrane impermeant nucleic acid intercalator used to stain dead cells, and 7-AAD (7-aminoactinomycin D which is a membrane impermeant fluorescent DNA binding dye commonly used for FACS).

In a specific embodiment, a time-course collection of four dose-response readouts (viability, necrosis, caspase activity, and annexin exposure) was performed.

Preparation of HepG2 cells. Briefly, HepG2 cells were cultured in MEM-alpha with 10% FBS (complete medium). Cell counts were performed with trypan blue to determine average cell number and to verify that the cells were healthy.

Electroporation of ASOs. Standard cell culture protocols were used. Briefly, cell collection was always performed in the morning. Cells were washed with dPBS and detached from the cell plate by applying trypsin for 5 minutes at 37 degrees C. Once the cells detached, the trypsin was neutralized by adding 8 mL complete medium and resuspending the cells. Cell suspensions were centrifuged at 300×g for 5 minutes. Supernatant was removed and cells resuspended in 1 mL of complete medium. Cell counts were performed using serial dilutions and used to calculate a 20 mL final cell suspension with a total 6.75×10^6/total cell count.

A total of four serial (1:2) dilutions were performed such that each OBM was prepared at 5 different cell densities and OBM concentrations.

OBM/HepG2 cell preparations were transferred to an electroporation plate and electroporated using a BTX ECM 830 square wave plate electroporator and a Plate Handler BTX HT 96 well system. The electroporated cells were pipetted up and down to ensure a homogenous cell suspension for seeding. Electroporated cells were transferred to a 384-well plate and incubated at 37 C, 5% CO2 for 5-6 hours.

Cytotoxic Assays. Cytotoxicity of OBM's was determined using various dye-based assays to assess real-time cell viability and apoptosis/necrosis onset. Assays included, but were not limited to, RealTime-Glo MT Viability Assay, CellEvent Caspase-3-7 Assay and RealTime-Glo Annexin V Apoptosis and Necrosis assay. Plates were imaged using a Cytation 5 imaging reader pre-warmed to 37 C. Wells were imaged under brightfield using the 4× objective, followed by a plate read of the green channel and then of the luminescence. Data were observed over 3 days and plates were imaged seven (7) times post-electroporation at time 6, 23, 26, 29, 47, 50, and 53 hours.

Figure 12:
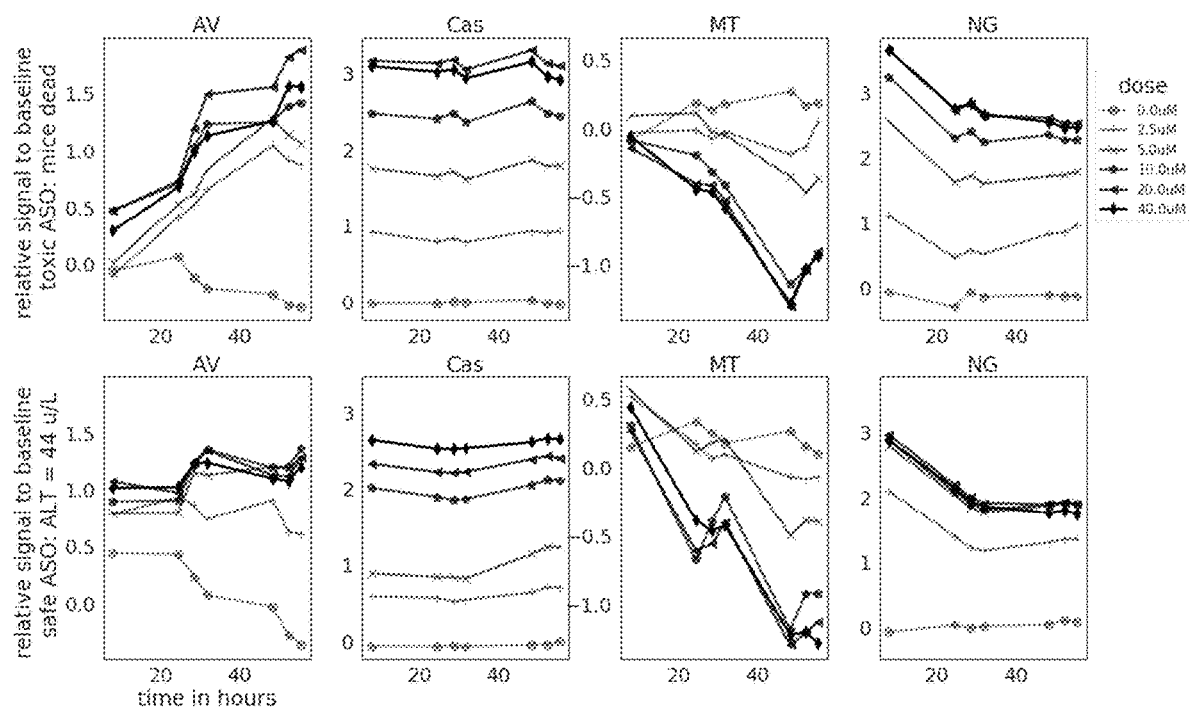
FIG. 12 is an exemplary depiction of in vitro Necrosis (NG), Caspase Cas), Annexin V (AV) and Cell viability (MT) signals for two engineered OBMs, with top row for an in vivo toxic OBM, and bottom row for in vivo safe OBM. Dose of OBM is in caption (0, 2.5, 5.0, 10, 20, 40 µM concentrations), with darker colors representing higher doses. The signal plotted is log 2 fold change relative to untreated samples, matched by times in hours (8, 22, 24, 28, 32, 48, 52 and 56 hours).

Cytotoxic Results. In vitro Necrosis, Caspase, Annexin V and Cell viability signals for the engineered OBMs aligned with the in vivo ALT (U/L) data. Exemplary cytotox results are shown in FIG. 12.

IV.G. Example 8—Validation Step of 80 OBMs Using Refined Predictive Model: In Silico Toxicity Analysis of 80 Published 3-8-3 LNA Vs Predicted 3-10-3 LNA OBMs to Validate Step 1 and Step 2 Toxicity Models For the sake of clarity, the methods described herein are now described in the context of a particular example.

To validate provided methods and demonstrate accuracy of the Step 1 and Step 2 models produced, 80 OBM sequences were selected that had publicly available toxicity measures (ALT, Cdkn1a, and Caspase levels) for 3-8-3 LNAs (3 nt with an extra methylene bridge fixed to the ribose moiety, an 8 nt "gap", followed by another 3 LNA) bridged-nucleic acid architecture. The dosing regimen for the test 3-8-3 LNA data was significantly lower at total dosage of only 100 mg/kg, versus our 150 mg/kg total dose. Therefore, the test data was filtered for ALT levels that were greater than 500 (U/L) (or log 26(500) is 2.69897000434) which resulted in 26 toxic sequences against which to test the predictive accuracy of the Step 1 and Step 2 models (Table 20).

Figure 13:
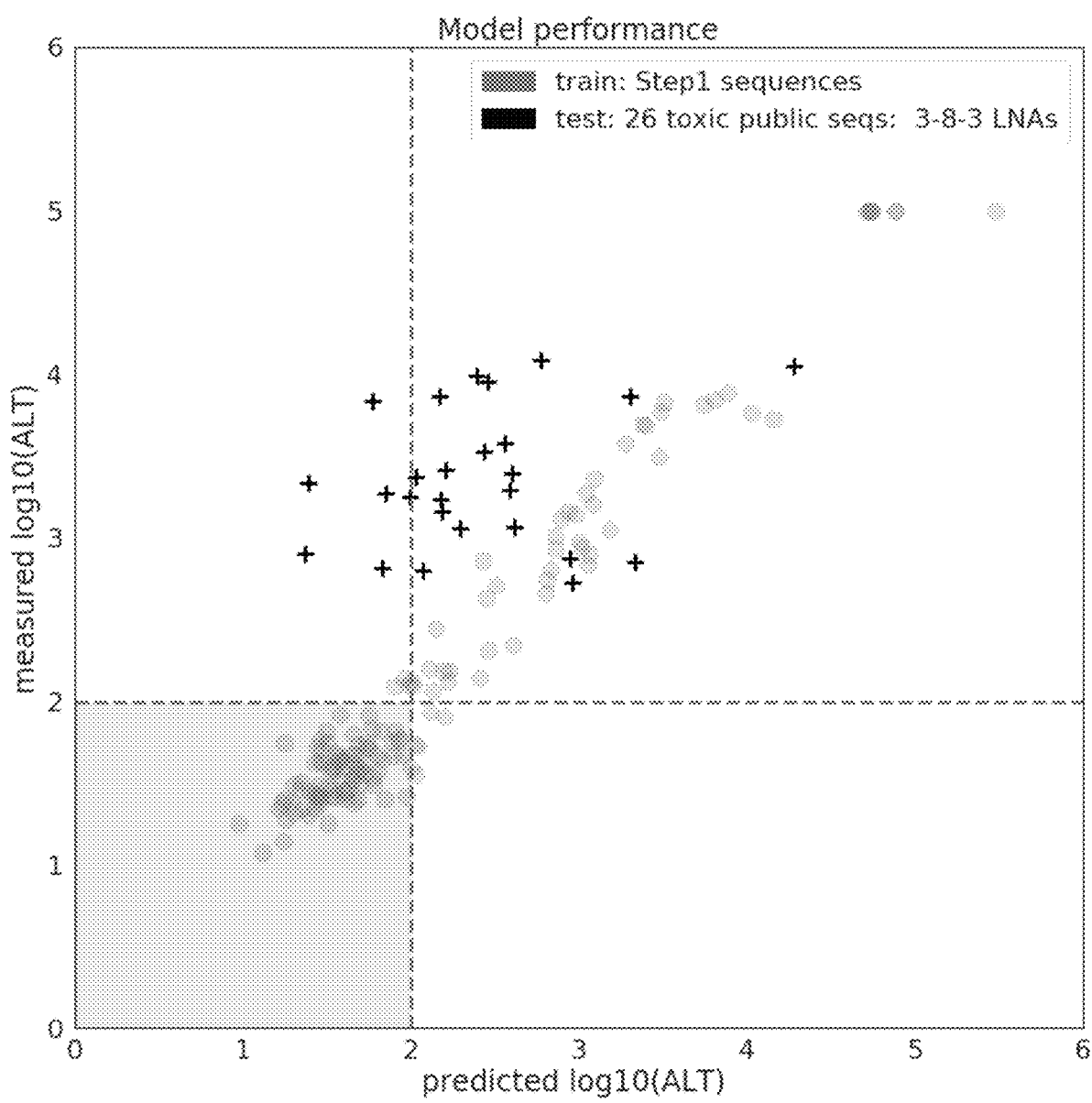
FIG. 13 is an exemplary depiction of model performance of 26 toxic 3-8-3 LNAs tested against 128 training sequences 3-10-3 LNAs designed in Step 1 (128). 3-10-3 LNA dosing scheme: 75 mg/kg per week, 2-week study, C57BL/6 mice, ALT, AST measured at 72 hours after second dose. Test sequences are 3-8-3 LNA dosed at 100 mg/kg (lower dose than training set) and therefore only toxic sequences are considered.

First, the 26 test 3-8-3 sequences were run through the Step 1 model (trained on 128 in vivo sequences) to predict toxicity as a 3-10-3 OBM. The Step 1 model performed exceptionally well correctly predicting 21 sequences as having toxic ALT levels (FIG. 13). This was an unexpectedly high level of accuracy after having trained on only 128 sequences.

Figure 14:
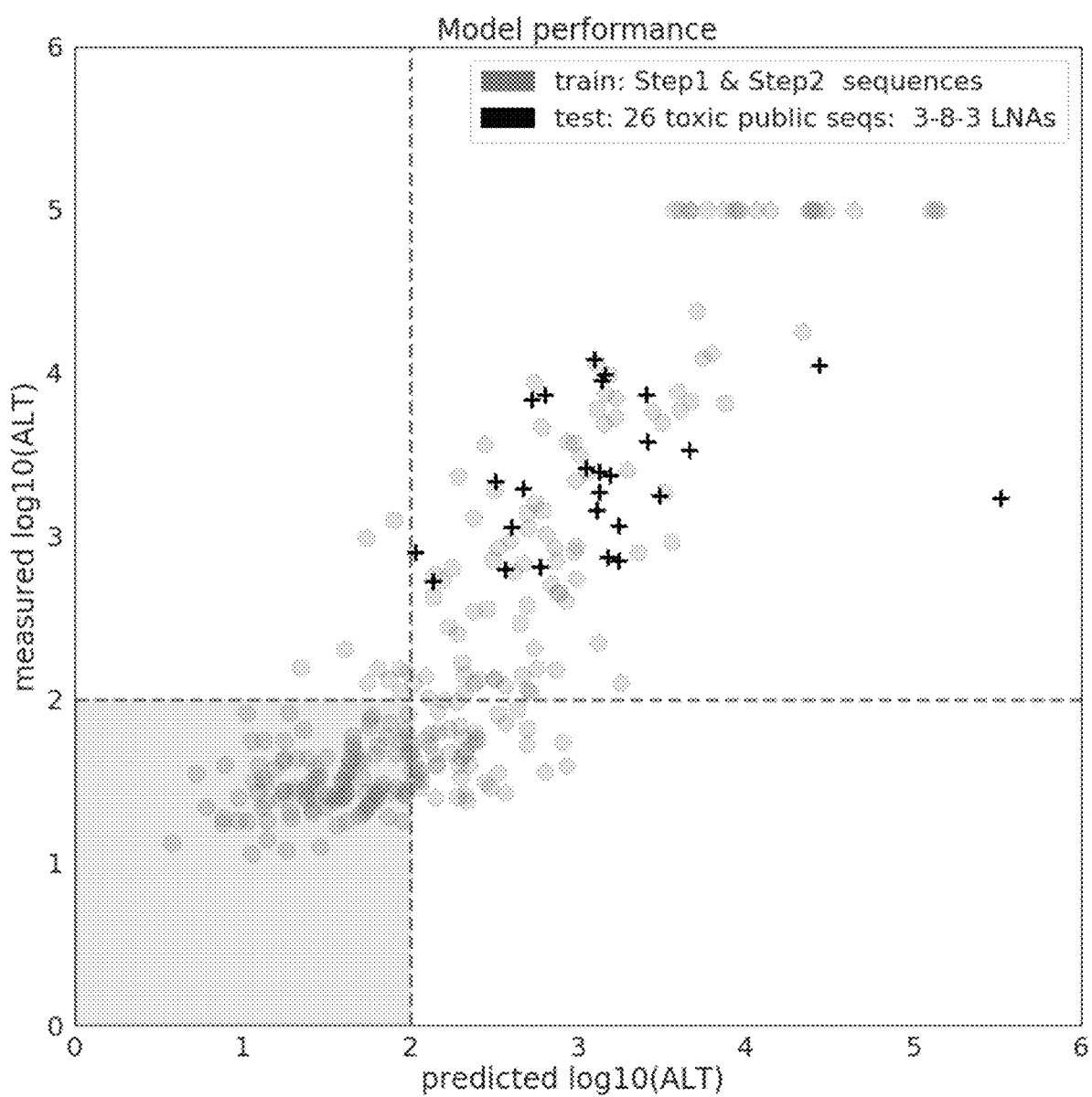
FIG. 14 is an exemplary depiction of model performance of 26 toxic 3-8-3 LNAs tested against 256 training sequences 3-10-3 LNAs designed in Step 1 & Step 2 (128+128). 3-10-3 LNA dosing scheme: 75 mg/kg per week, 2 week study, C57BL/6 mice, ALT, AST measured at 72 hours after second dose. Test sequences are 3-8-3 LNA dosed at 100 mg/kg (lower dose than training sets) and therefore only toxic sequences are considered.

Next, the 26 test 3-8-3 sequences were run through the refined model trained on both the Step 1 and Step 2 sequences (256 in vivo sequences) to predict toxicity as a 3-10-3 OBM. Remarkably, after training on only 256 sequences the refined model was able to accurately predict all 26 sequences as toxic in a 3-10-3 LNA architecture (FIG. 14).

TABLE 20

Publicly available 38-3 LNA ASO sequences and measured and predicted ALT (U/L) levels

| SEQ ID NO. | Sequence | Target | Measured 3-8-3 LNA ALT (U/L) | Measured 3-8-3 LNA ALT log10 | Refined Model Predicted 3-10-3 LNA ALT log10 | Validate |
|---|---|---|---|---|---|---|
| 1 | AAGTCTGTTACCCC | GR | 1943 | 3.29 | 2.68 | Validated |
| 2 | CAGTAGTCTTTCAG | ApoC3 | 646 | 2.81 | 2.77 | Validated |
| 3 | GGTATTCAGTGTGATG | ApoC3 | 705 | 2.85 | 3.24 | Validated |
| 4 | GTAGTCTTTCAGGG | ApoC3 | 742 | 2.87 | 3.18 | Validated |
| 5 | GTATTGAGGTCTCA | ApoC3 | 794 | 2.90 | 2.03 | Validated |
| 6 | AGTCTTGGCCCTCT | GR | 1764 | 3.25 | 3.49 | Validated |

TABLE 20-continued

Publicly available 38-3 LNA ASO sequences and measured and predicted ALT (U/L) levels

| SEQ ID NO. | Sequence | Target | Measured 3-8-3 LNA ALT (U/L) | Measured 3-8-3 LNA ALT log10 | Refined Model Predicted 3-10-3 LNA ALT log10 | Validate |
|---|---|---|---|---|---|---|
| 7 | GCATTGGTATTCA | ApoB | 2154 | 3.33 | 2.51 | Validated |
| 8 | GTCTCTTTACCTGG | GR | 8979 | 3.95 | 3.14 | Validated |
| 9 | TAATGCTCGATCCC | None | 3369 | 3.53 | 3.66 | Validated |
| 10 | AAGTCTGTTTCCCC | GR | 12186 | 4.09 | 3.10 | Validated |
| 11 | TCATGGCTGCAGCT | ApoC3 | 532 | 2.73 | 2.14 | Validated |
| 12 | TGCCTCTAGGGATG | ApoC3 | 627 | 2.80 | 2.57 | Validated |
| 13 | AGCAGCTGCCTCTA | ApoC3 | 1129 | 3.05 | 2.61 | Validated |
| 14 | GTGCTCCAGTAGTC | ApoC3 | 1157 | 3.06 | 3.24 | Validated |
| 15 | TGCTCCAGTAGTCT | ApoC3 | 1436 | 3.16 | 3.11 | Validated |
| 16 | AGTGCATCCTTGGC | ApoC3 | 1706 | 3.23 | 5.52 | Validated |
| 17 | CCTGCTGGGCCACC | ApoC3 | 1868 | 3.27 | 3.13 | Validated |
| 18 | GCTCCAGTAGTCTT | ApoC3 | 2369 | 3.37 | 3.19 | Validated |
| 19 | ACTCCAAATCCTGC | GR | 2461 | 3.39 | 3.13 | Validated |
| 20 | TCCAAGGACTCTCA | GR | 2630 | 3.42 | 3.05 | Validated |
| 21 | ACCTGGGACTCCTG | ApoC3 | 3796.7 | 3.58 | 3.41 | Validated |
| 22 | GGTTTGCAATGCTT | GR | 6894 | 3.84 | 2.72 | Validated |
| 23 | TGGCCCTGCTGTGG | GR | 7376 | 3.87 | 3.41 | Validated |
| 24 | CCGTTGGTGCCAGT | GR | 7376 | 3.87 | 2.81 | Validated |
| 25 | GTCTTCTCCCGCCA | GR | 9781 | 3.99 | 3.16 | Validated |
| 26 | AGGTGCTTTGGTCT | GR | 11155 | 4.05 | 4.44 | Validated |

Unexpectedly, after only training on only 256 sequences the model was able to correctly predict toxicity for 26 test sequences demonstrating that performing n-gram mutations (including single, multiple or correlated mutations) on an initial set or set of initial oligonucleotides facilitated the creation of an orders-of-magnitude faster first training set for training a machine-learned model in a first stage. Likewise, these results also confirmed that generating a second set of oligonucleotides (either randomly, or by design, e.g. non-random), using identical or new n-gram mutation types, in single, multiple or a correlated manner from the first set, facilitated the creation of an orders-of-magnitude faster second training set for training a machine-learned model in a second stage. Creating data sets that are optimal for machine learning have significant economic costs.

Among other things, one surprising and unexpected aspect of the provided methods is that they allow for incredibly efficient exploration of an almost infinite space of sequence X chemistry X architecture that was previously impossible to do (FIG. 14). The current paradigm for creating new OBMs, enabling new nucleic acid chemistries, or leveraging new mechanisms of action are through edisonian trial-and-error screening campaigns that come at a huge economic cost (of both money and time). For example, in one embodiment imagine the length of a single target sequence of interest is 16 nt and, quite conservatively, the n-gram size of interest is 4. Considering only standard nucleotides of A, T, C or G there are 256 possible 4 n-grams for a contiguous k-mer and 12 possible positions in the sequence for each n-gram (16−4=12). To explore the full diversity of n-grams at every position, a POSITA would need 3072 sequences (12*256). This space increases rapidly when non-standard nucleotides and/or additional chemistries/architectures are added. Moreover, OBMs work via multiple complex mechanisms including engaging enzymes (RNase H, RNAi, ADAR, etc.) and by steric blocking via modulation of splicing, RBP binding, secondary structure, co- & post-transcriptional modification of coding/non-coding RNA processing, etc. Traditional screening campaigns fail to optimize safety, efficacy or discover optimal design because the design space of sequence and chemistry is huge.

Surprisingly, the methods provided herein engineer and optimize all OBM classes by rapidly creating highly informative datasets for building machine learning (ML) and artificial intelligence (AI) models for predictive pharmacology.

IV.H. Example 9—Validation Step of 16 OBMs Using Refined Predictive Model: In Vivo Analysis of 16 cEt Vs LNA OBMs in Mice to Confirm Predictive Model of Systemic Tolerability To validate provided methods and demonstrate predictive accuracy of the Step 1 and Step 2 models with real-world measured in vivo data, sixteen (16) 3-10-3 cEt test sequences were selected with publicly available toxicity measures (ALT, Cdkn1a, and Caspase levels) for a cEt (S-constrained ethyl) bridged-nucleic acid architecture (Table 21). In general, ALT levels below 100 (U/L) are considered safe and the cEt antisense oligo architecture has been described as a "safer" (less toxic) chemistry than locked nucleic acid (LNA) chemistries. Validation against the 16 test sequences was first performed in silico against the two model versions and then in vivo testing actual OBM toxicity in mice.

Figure 15:
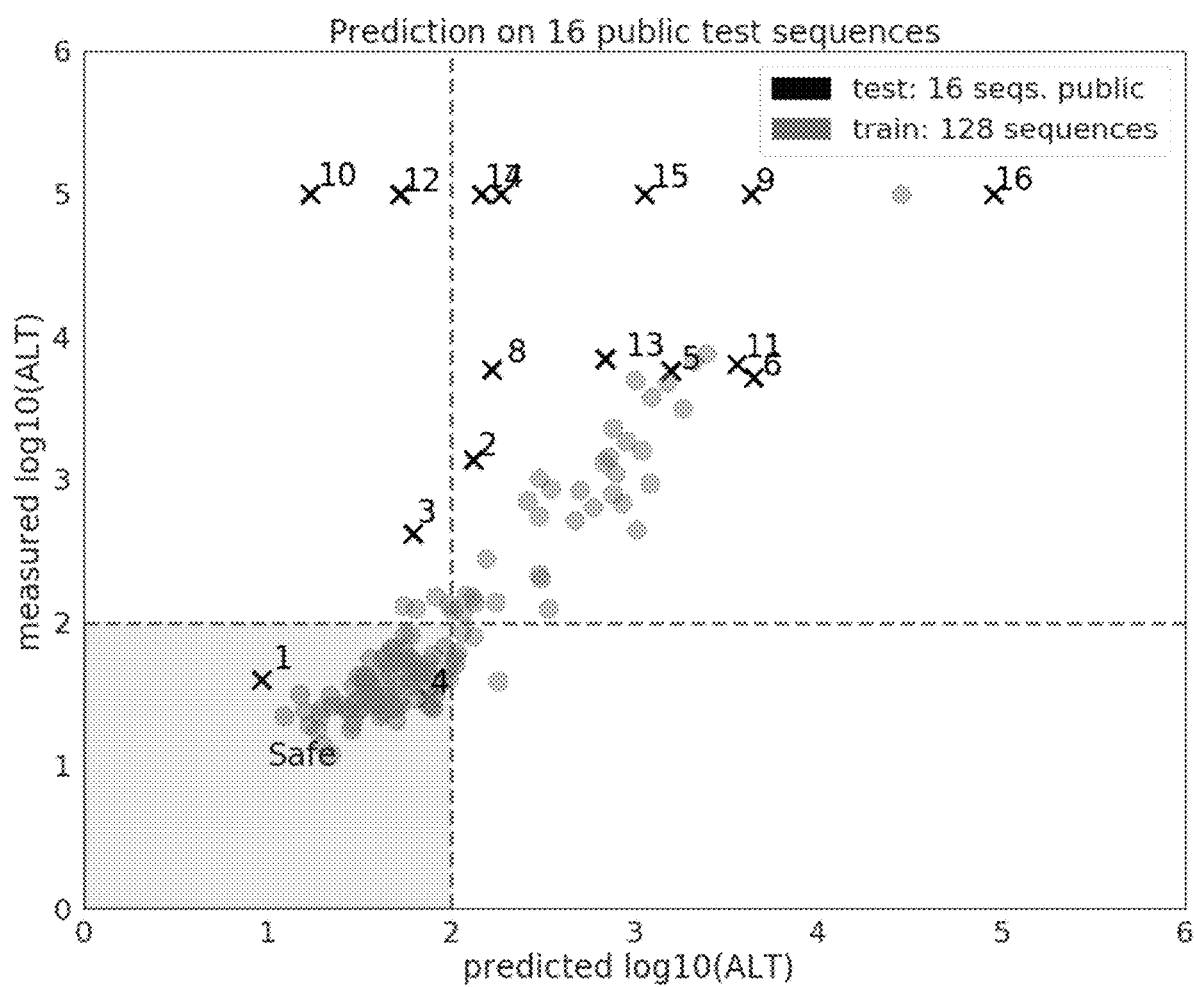
FIG. 15 is an exemplary depiction of model performance of 16 cEts tested against 128 training sequences 3-10-3 LNAs designed in Step 1 (128). 3-10-3 LNA dosing scheme: 75 mg/kg per week, 2-week study, C57BL/6 mice, ALT, AST measured at 72 hours after second dose. Test sequences are 3-10-3 LNA versions of 3-10-3 cEts, which were tested in vivo using animal studies, same design as above.
Figure 16:
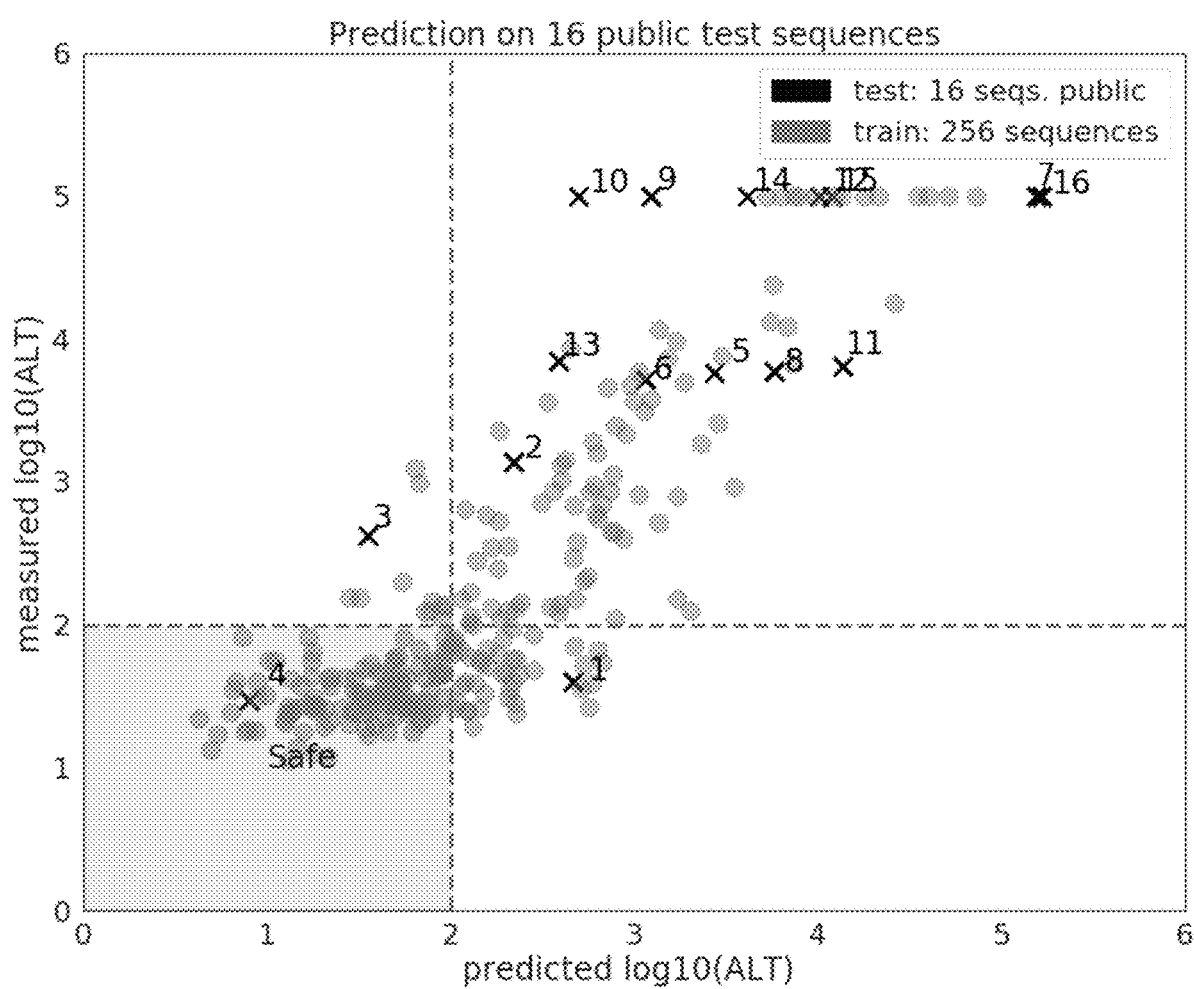
FIG. 16 is an exemplary depiction of model performance of 16 cEts tested against 256 training sequences 3-10-3 LNAs designed in Step 1 and Step 2 (128 and 128). 3-10-3 LNA dosing scheme: 75 mg/kg per week, 2-week study, C57BL/6 mice, ALT, AST measured at 72 hours after second dose. Test sequences are 3-10-3 LNA versions of 3-10-3 cEts, which were tested in vivo using animal studies, same design as above.

First, the 16 test 3-10-3 cEt sequences were run through the Step 1 model (trained on 128 in vivo sequences) to predict toxicity in a 3-10-3 LNA architecture (FIG. 15). The Step 1 model predicted 12/16 sequences as having toxic ALT levels. Next, the 16 test 3-10-3 cEt sequences were run through the refined model trained on both the Step 1 and Step 2 sequences (256 in vivo sequences) to predict toxicity as a 3-10-3 OBM (FIG. 16). Remarkable, after training on only 256 sequences the refined model was able to predict SEQ ID NO. 4 as a non-toxic 3-10-3 LNA alternative to the published toxic 3-10-3 cEt architecture.

Next, to confirm the model predictions and provide in vivo validation of the provided methods, each published cEt sequence was synthesized as a 3-10-3 gapmer LNA OBM and dosed in vivo in mice in a 5 week systemic tolerability study.

Mice. Male C57BL/6 mice aged 9-12 weeks were maintained on a 12-hour light/dark cycle and were fed ad libitum normal mouse chow. Animals were acclimated for at least 7 days in the research facility before initiation of the experiment. Oligonucleotide-based medicines (OBMs) were prepared in buffered saline (PBS) and sterilized by filtering through a 0.2 micron filter. OBMs were dissolved in PBS for subcutaneous injection.

Study Design. Total Study Design was 5 weeks. On Day −1 (before the study started) body weight was recorded and mice were randomized into 17 total groups of 5 mice each per treatment (16 OBM groups and 1 saline control group). Groups received subcutaneous injections of an OBM at a dose of 75 mg/kg at the start of Week 2, Week 3, Week 4, for 3 total doses. No dose was administered during Week 1 (observation period) or Week 4 (washout period).

Blood draws (via eye bleed, tail bleed or cardiac bleed) were administered 72 hours after each dosing or 72 hours after the start of Week 4 during the washout period. Observations and read-outs included body weight (BW), temperature, ALT, AST, BUN, creatinine, CRP and total bilirubin (TBILI). On Week 5 animals were sacrificed and wet tissue weight measured for liver, kidney and spleen.

TABLE 21

Public test 3-10-3 cEt sequences and predicted and measured ALT (U/L) levels

| SEQ ID NO: | CBID | Sequence | Pub. ALT (U/L) [cEt] | cEt bin ≤100 (safe) ≥200 (toxic) | Model Prediction for 3-10-3 LNA | Measured ALT (U/L) [3-10-3 LNA] | Mouse Target | Human Target |
|---|---|---|---|---|---|---|---|---|
| | Saline Control | — | — | — | — | 21.6 | — | — |
| 27 | 838280 | CAAAGTGATACCAGTT | 21 | SAFE | SAFE | 40 | Grm7, F11, Cdh20 | NELL1 |
| 28 | 982655 | GAATCTCCTTTTCCAG | 98 | SAFE | TOXIC | 434 (4/5 dead) | Mtdh | GSG1L, CLASP1, TECTA, MTDH |
| 29 | 416562 | GAGGATGGCAAGCACA | 131 | | TOXIC | 114 (3/5 mice dead) | Hdac2, Ank2 | SH3TC1, CREBBP, TRAK1 |
| 30 | 516166 | GTACCTATAGTCTCTG | 182 | | SAFE | 35.2 | Hdac2 | FBXL7, TMTC2 |
| 31 | 801663 | CTTCTTGATGTCTTTC | 533 | TOXIC | TOXIC | 2054 (1/5 dead) | Atp6v1g1, Ankrd6, Usp37, Wwtr1, Dpyd | ABCC9, NEXMIF |
| 32 | 999945 | CTTTTCTATCAGTCTC | 608 | TOXIC | TOXIC | 138 | Usp12, Nes, Nes, Adamts20 | USP12, TCERG1L, RANBP17, DNAAF5, ARHGAP15, CNTN1 |
| 33 | 392108 | TTTTGTGTCTTCTGTA | 2347 | TOXIC | TOXIC | (5/5 dead) | F11, Psmb3, Nrxn1, Gli3, Atrnl1, Lrp6 | ARID5B, YIPF1, SYT14 |

TABLE 21-continued

Public test 3-10-3 cEt sequences and predicted and measured ALT (U/L) levels

| SEQ ID NO: | CBID | Sequence | Pub. ALT (U/L) [cEt] | cEt bin ≤100 (safe) ≥200 (toxic) | Model Prediction for 3-10-3 LNA | Measured ALT (U/L) [3-10-3 LNA] | Mouse Target | Human Target |
|---|---|---|---|---|---|---|---|---|
| 34 | 567908 | ACCCTCAAGTCTCCTG | 3894 | TOXIC | TOXIC | 510 | Tmem126b, Ephb2, Hdac2, Stxbp5 | MAK16, TTI2, HDAC2 |
| 35 | 790763 | TCTCCTTGCTGTATTT | 11752 | TOXIC | TOXIC | (5/5 dead) | Nek10, Gm11639, F11 | ASTN2, LDB2, DCLK2, RAB11FIP1, FER1L6, CDKAL1, SOS1 |
| 36 | 765307 | GTCAGTATCCCAGTGT | 13168 | TOXIC | TOXIC | (5/5 dead) | F11 | |
| 37 | 810069 | GACTCTCTGATGATAC | 14907 | TOXIC | TOXIC | 2054 | Hdac2 | HDAC2 |
| 38 | 875287 | ATTCTGTGTGCACTGC | 24858 | TOXIC | TOXIC | (5/5 dead) | Mapk4, F11, Katnb1 | ARMC3 |
| 39 | 773959 | TTGCCAATATCACCAT | 37277 | TOXIC | TOXIC | 514 | Zfpm1, Galnt21 | SNX29, PLCB1, SLIT3, PDE9A |
| 40 | 453801 | GTCTGTGCATCTCTCC | dead | TOXIC | TOXIC | (5/5 dead) | F11, Atp1a3 | HDAC9 |
| 41 | 985738 | TCTTGTCTGACATTCT | dead | TOXIC | TOXIC | (5/5 dead) | F11, Hs3st2 | |
| 42 | 487997 | TAGTCTCTGTCAGTTA | dead | TOXIC | TOXIC | (5/5 dead) | Hdac2 | |

Results. Public data for cEt architecture, evaluating ALT as a measure of toxicity, reported that SEQ ID NO. 1 was safe, SEQ ID NO. 2 borderline, and SEQ ID NOs. 3-16 were toxic. The model non-toxic prediction for SEQ ID NO. 4 was confirmed in vivo with an average ALT of 35.2 (U/L) (compared to ALT level of 182 of test sequence cEt). Similarly, methods described herein surprisingly predicted SEQ ID NO. 6 would reduce ALT levels when prepared in an LNA architecture as compared to published data reporting the equivalent cEt chemistry with toxic ALT levels thus validating the models and methods described herein. In vivo results confirmed the model prediction for SEQ ID NO. 6 with average ALT levels of 138 (U/L) compared to ALT level of 608 (U/L) of the test sequence cEt.

Most unexpectedly, the provided methods built an accurate and predictive toxicity model using a minimal 256 survey compounds. In addition, when using the same chemistry but different sequences, there was an order of magnitude range in maximum tolerated dose. Traditional OBM screening paradigms cost millions of dollars and take a minimum of 2-3 years from target identification to lead OBM identification. A typical OBM screening paradigm will screen ~100-1000 sequences in vitro for activity and cytotoxicity, ~10-100s for in vivo toxicity and activity screening, resulting in ~5-10 leads.

In contrast, the methods of the present disclosure provide for OBMs to be directly engineered with optimal chemical design (maxima efficacy/avoid toxicity) at a fraction of the cost and time and avoid the inefficiencies of a traditional OBM screen. One surprising aspect of the methods described in the present disclosure is the orders-of-magnitude leaner in data requirements for building robust predictive models as demonstrated in this (and previous) examples.

IV.I. Example 10—Active Learning Survey to Refine Neurotoxicity Model—In Vitro FLIPR Calcium Channel Assay Analysis of OBMs in Primary Neuronal Cultures OBM-induced neurotoxicity presents as acute, delayed neurotoxicity or combinations thereof. A challenge of centrally delivered OBMs is often acute neuronal toxicities. Without wishing to be bound to a particular theory, evidence supports that acute neuronal toxicities are caused by OBM interactions at the neuronal membrane, and that these OBM/membrane interactions ultimately lead to dysfunction of the neuronal membrane which results in death of the neuron.

This example describes assays developed to monitor membrane potentials, and to specifically measure and monitor calcium influx into neurons after treatment with an OBM. In a specific embodiment, the effects of OBM on calcium flux in rat cortical neuron (RCN) cells was measured using ionomycin as a calcium agonist. These data were used to create a training set comprising a correlation between an OBM (each OBM comprising a sequence, e.g., 16-mer, a chemistry, e.g., LNA, and a specific architecture, e.g., 3-10-3) and a specific biophysical effect on neurotoxicity. In some embodiments, neurotoxicity was measured by monitoring neuronal membrane potentials. In some embodiments, membrane potentials included measuring calcium concentrations. In some embodiments, membrane potentials included measuring potassium concentrations. In some embodiments, membrane potentials were measured using a fluorescent dye-based assay. In some embodiments, the fluorescent dye was Fluo-6AM (Fluo-6-penta acetoxymethyl ester). Fluo-6AM is a calcium indicator that exhibits an increase in fluorescence upon binding Ca2+ and is particularly useful to image the spatial dynamics of Ca2+ signaling, in flow cytometry experiments involving photoactivation of caged chelators, second messengers, neurotransmitters, and for cell-based pharmacological screening. In some embodiments, a FLIPR calcium channel assay is used to monitor membrane potentials after OBM treatment.

Any type of cell can be used to monitor membrane potential after OBM treatment. In some embodiments, cells comprised SH-SY5Y cells or primary rat cortical neurons. In a specific embodiment, neuronal cells were primary rat cortical neurons. In some embodiments, calcium influx in primary rat cortical neurons (RCN) was measured via a FLIPR assay after in vitro treatment of OBM.

Cell preparation and culture. Fresh primary rat cortical neurons were isolated according to standard laboratory procedures and seeded as per Thermo B-27 Plus Neuronal Culture System guidelines. Briefly, 4,000 cells/well were seeded on seven (7) PDL-coated 384-well plates with a total volume of 25 µL of cells/well. In some embodiments, 20,000 cells/well were seeded in 96-well plates with a total volume of 100 µL of cells/well. Culture dishes were incubated at 37° C. in a humidified atmosphere at 5% CO2. Every two to three days half of the medium from each well was aspirated and replaced with the same volume of fresh media. The same plating and culture procedures were also used for commercial RCN and SH-SY5Y cells purchased from vendors.

FLIPR assay conditions. Assay volume for the agonist study was as follows: 25 µL cells +25 µL Fluo-6AM dye+10 µL (6×) OBMs (first addition).

Assay volume for the antagonist study was as follows: 25 µL cells +25 µL Fluo-6AM dye+10 µL (6×) OBMs (first addition)+10 µL (7×) ionomycin (ionomycin is an ionophore and an antibiotic that binds calcium ions in a 1:1 ratio).

OBMs were administered at 4 concentrations (30 µM, 15 µM, 7.5 µM and 3.75 µM) to determine how calcium flux was affected by OBM dosing. The calcium agonist, ionomycin, was administered in the same well after ASO dosing at 1 µM for every OBM concentration. HBTS buffer was used as a negative control. Standard FLIPR assay protocols were used, which are familiar to a POSITA. Briefly, 20 thousand cells were seeded per well in a 384-well flat, clear bottom, black walled plat, quadrant wise coated with PDL. Seeded plates were incubated for 48 hours at 37° C. and 5% CO2. On the day of experiment (21st day) media was completely removed and replenished by PSS buffer solution. Fluo-6AM dye was loaded on the day of the assay and the plate incubated for 30 minutes at 37° C. and 5% CO2 and then kept at room temperature (RT) for 5 minutes. A signal test was done prior to starting the FLIPR assay to confirm the uniformity of cell seeding. Thirty-four (34) second baseline fluorescence readings were taken prior to treating with OBMs (first addition). OBM compounds and agonists were added by FLIPR and the data recorded through FLIPR. The machine was a FLIPR Tetra with 96-well head and baseline fluorescence and Ca2+ responses were measured using a cooled CCD camera with excitation at 470-495 nM and emission at 515-575 nM. Data was expired and standard analysis performed.

A subset of OBMs from Group 2 and Group 3 of the in vivo 72-hour acute study were assayed. OBMs were assayed as follow: Plate 1—CR-AA-0079 through CR-AA-0088; Plate 2—CR-AA-0089 through CR-AA-0099; Plate 3—CR-AA-00100 through CR-AA-00109; Plate 4—CR-AA-00110 through CR-AA-00119; Plate 5—DR-AA-00120 through CR-AA-00132. A second FLIPR batch included Plate 1—CR-AA-00133 through CR-AA-00141; Plate 2—CR-AA-00142 through CR-AA-00150.

Figure 17:
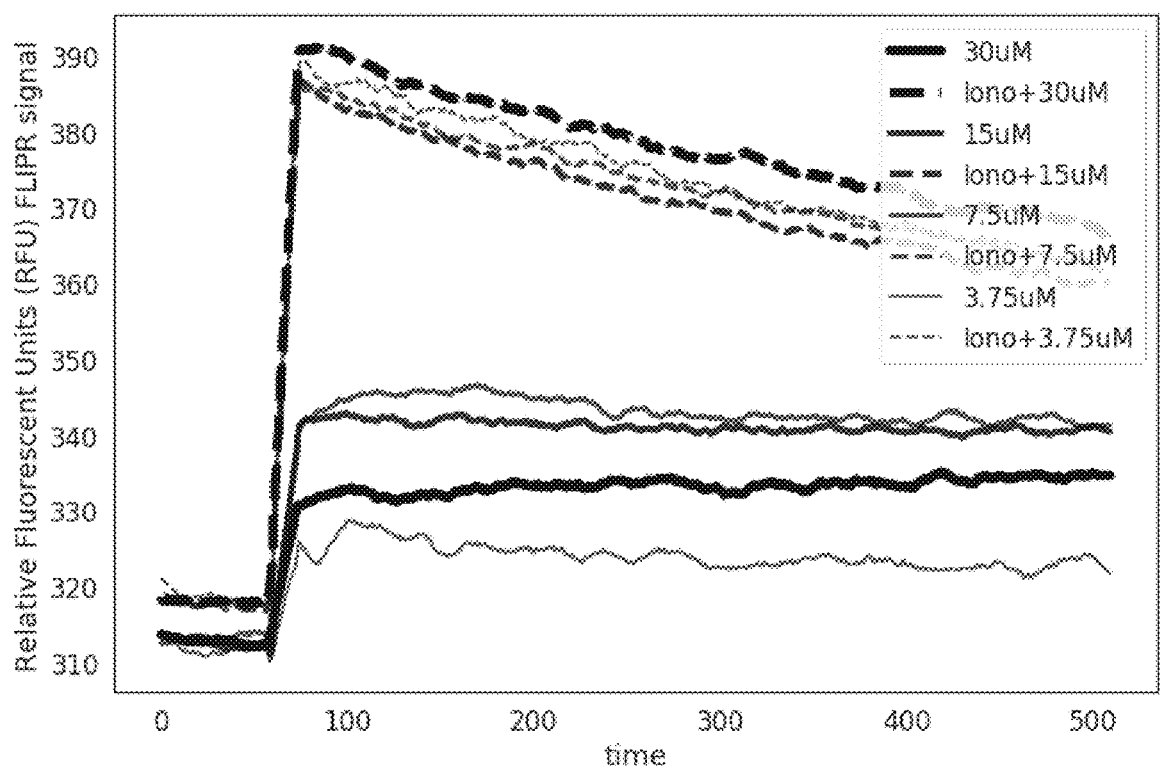
FIG. 17 is an exemplary depiction of an in vitro neurotoxicity assay (exemplary ASO Experimental Group 155024). OBMs were administered at 4 concentrations (30 µM, 15 µM, 7.5 µM and 3.75 µM) to determine how calcium flux was affected by OBM dosing. The calcium agonist, ionomycin, was administered in the same well after ASO dosing at 1 µM for every OBM concentration. HBTS buffer was used as a negative control.

The effect of an exemplary OBM (155024) on calcium influx in rat cortical neurons is shown in FIG. 17.

V. Additional Considerations

The foregoing description of the embodiments of the disclosure has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the disclosure in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules can be embodied in software, firmware, hardware, or any combinations thereof.

Any of the steps, operations, or processes described herein can be performed or implemented with one or more hardware or software modules, alone or in combination with other devices. In some embodiments, a software module is implemented with a computer program product including a computer-readable non-transitory medium containing computer program code, which can be executed by a computer processor for performing any or all of the steps, operations, or processes described.

Embodiments can also relate to a product that is produced by a computing process described herein. Such a product can include information resulting from a computing process, where the information is stored on a non-transitory, tangible computer readable storage medium and can include any embodiment of a computer program product or other data combination described herein.

Finally, the language used in the specification has been principally selected for readability and instructional purposes, and it cannot have been selected to delineate or circumscribe the inventive subject matter. It is therefore intended that the scope of the invention be limited not by this detailed description, but rather by any claims that issue on an application based hereon. Accordingly, the disclosure of the embodiments herein is intended to be illustrative, but not limiting, of the scope of the invention, which is set forth in the following claims.

What is claimed is:

1. A method for training a machine-learned model, comprising:
generating a first set of oligonucleotides by performing all possible single n-gram mutations of an initial oligonucleotide to obtain oligonucleotides mapped to a distributed range of measures of having a biophysical effect such that each n-gram of the initial oligonucleotide is represented at least once by the first set of oligonucleotides;
synthesizing a subset of the first set of oligonucleotides;
administering the synthesized subset of the first set of oligonucleotides to one or more cells;
measuring, for each oligonucleotide of the subset of the first set of oligonucleotides, the biophysical effect on the one or more cells;
creating a first training set based, at least in part, on the synthesized subset of the first set of oligonucleotides and the measures of the biophysical effect;
training a machine-learned model in a first stage using the first training set, the machine-learned model configured to map an oligonucleotide sequence to a measure of the biophysical effect;
after training the machine-learned model in the first stage, generating a second set of oligonucleotides such that each n-gram of the first set of oligonucleotides is represented at least once by the second set of oligonucleotides, the second set of oligonucleotides selected based on an output of the machine-learned model such that the second set of oligonucleotides corresponds to a distributed range of measures of the biophysical effect, the second set of oligonucleotides including an approximately equal number of oligonucleotides that correspond to the biophysical effect and that do not correspond to the biophysical effect;
creating a second training set comprising, for each oligonucleotide of the second set of oligonucleotides, a sequence of the oligonucleotide and a measure of the biophysical effect of the oligonucleotide determined based on real-world experimental determination;
training the machine-learned model in a second stage using the second training set;
receiving a desired measure of the biophysical effect;
using the machine-learned model to generate an oligonucleotide based on the desired measure of the biophysical effect, and
synthesizing the generated oligonucleotide to produce an oligonucleotide-based medicine.

2. The method of claim 1, further comprising:
generating a final set of oligonucleotides using the trained machine-learned model.

3. The method of claim 2, further comprising:
accessing a set of biophysical requirements for the oligonucleotide-based medicine; and
selecting a subset of the generated final set of oligonucleotides that satisfy the set of biophysical requirements, the selected subset include the generated oligonucleotide.

4. The method of claim 2, wherein the final set of oligonucleotides comprises one or more of: a set of aptamers, a set of oligonucleotide-aptamer conjugates, a set of antisense oligonucleotides (ASO), a set of anti-gene oligonucleotides, a set of CpG oligonucleotides, a set of single-guide RNAs, a set of dual-guide RNAs, a set of targeter RNAs, a set of activator RNAs, a set of LNA oligonucleotides, a set of constrained ethyl (cEt) oligonucleotides, a set of adenosine deaminase acting on RNA (ADAR)-guiding RNA (AD-gRNAs), a set of steric-blocking oligonucleotides (SBOs), a set of antisense oligonucleotides that recruit endogenously expressed ADARs, a set of antisense oligonucleotides that harness RNase H, a set of intron-targeted ASOs, and a set of exon-targeted ASOs.

5. The method of claim 2, wherein generating the final set of oligonucleotides using the trained machine-learned model comprises:
receiving an identification of a biophysical function to be performed by the oligonucleotide-based medicine (OBM) and an identification of the desired measure of the biophysical effect;
identifying a set of characteristics of an oligonucleotide associated with the biophysical function; and generating, using the trained machine-learned model, a set of oligonucleotides having one or more of the identified set of characteristics and corresponding to the desired measure of the biophysical effect.

6. The method of claim 5, wherein the biophysical function comprises one or more of: a reduction of immune-mediated inflammation, an increase in immune-mediated response, and an on-target engagement of the oligonucleotide to a target.

7. The method of claim 6, wherein the on-target engagement causes the oligonucleotide to perform an effective amount of one or more of: gene expression knock-down, RNA splicing modulatory behavior, gene expression upregulation, gene-editing, RNA-editing, protein specific targeting, receptor specific targeting, enzymatic substrate specific targeting, and distribution and uptake into tissues or cells.

8. The method of claim 7, wherein the target is an mRNA, a splicing site on a pre-mRNA, a truncated transcript, an aborted transcription product, or an antisense transcript.

9. The method of claim 5, further comprising identifying a dose for the OBM based on a relationship between a quantity of one or more of the final set of oligonucleotides and the measure of the biophysical effect.

10. The method of claim 1, wherein the biophysical effect comprises one or more of: a biological effect, a chemical effect, and a pharmacological effect.

11. The method of claim 1, wherein the biophysical effect comprises one or more of: cytotoxicity, membrane toxicity, immunotoxicity, an effect that inhibits membrane fluidity, a membrane fusion and fission event, and an immune response.

12. The method of claim 1, wherein the biophysical effect is a biological activity of the oligonucleotide, and comprises one of an on-target engagement of the oligonucleotide to a target molecule or an off-target engagement of the oligonucleotide to a target molecule.

13. The method of claim 1, wherein the biophysical effect comprises an inactivity of the oligonucleotide.

14. The method of claim 1, wherein the biophysical effect comprises a measure of one or more of: absorption, distribution, metabolism, excretion, pharmacokinetics or pharmacodynamics, substrate-target processing, dynamics, accessibility, inter-cellular distribution, intra-cellular distribution, and time-dependent availability.

15. The method of claim 1, wherein the machine-learned model is initialized by initializing a set of coefficients each representative of a correlation between n-grams of an oligonucleotide sequence and a presence of the biophysical effect.

16. The method of claim 15, wherein at least one coefficient of the set of coefficients is representative of a correlation between consecutive n-grams within the oligonucleotide and the presence of the biophysical effect.

17. The method of claim 1, wherein the machine-learned model comprises one of: an Ising model, a Potts model, a hidden Markov model, a continuous random field model, a directed acyclic graphical model, a random forest classifier, a logistic regression, a linear regression, a neural network, a sparsity-driven convex optimization fit, and a support vector machine.

18. The method of claim 1, wherein the n-gram mutations further comprise multiple n-gram mutations, gapped n-gram mutations, or correlated n-gram mutations on a set of one or more initial oligonucleotides.

19. The method of claim 1, wherein the second set of oligonucleotides are generated by design using identical or new n-gram mutation types in a single, multiple or correlated manner from the first set of oligonucleotides.

20. The method of claim 1, wherein the second set of oligonucleotides are generated randomly using identical or new n-gram mutation types in a single, multiple or correlated manner from the first set of oligonucleotides.

21. The method of claim 1, wherein training the machine-learned model in the first stage comprises performing a sparsity-constrained fit on the first set of oligonucleotides and whether each of the first set of oligonucleotides corresponds to the biophysical effect.

22. The method of claim 1, further comprising:
generating a third set of oligonucleotides;
determining, for each oligonucleotide of the third set of oligonucleotides, whether the oligonucleotide corresponds to the biophysical effect;
modifying the machine-learned model using the third set of oligonucleotides and whether each of the third set of oligonucleotides corresponds to the biophysical effect.

23. The method of claim 22, wherein the third set of oligonucleotides comprises approximately equal portions of oligonucleotides predicted to correspond to the biophysical effect and predicted to not correspond to the biophysical effect by the machine-learned model.

24. The method of claim 1, further comprising iteratively training the machine-learned model in subsequent stages until a stop condition is satisfied.

25. The method of claim 24, wherein the stop condition comprises one or more of: a number of iterations, a threshold predictive performance of the machine-learned model, and a below-threshold increase in predictive performance of the machine-learned model after an iteration.

26. The method of claim 2, wherein the subset of the first set of oligonucleotides comprises synthesizing no more than 32 or 256 oligonucleotides.

27. A method for training a machine-learned model, comprising:
generating a first set of oligonucleotides by performing all possible single n-gram mutations of an initial oligonucleotide to obtain oligonucleotides mapped to a distributed range of measures of having a biophysical effect such that each n-gram of the initial oligonucleotide is represented at least once by the first set of oligonucleotides;
creating a first training set comprising, for each oligonucleotide of the first set of oligonucleotides, a sequence of the oligonucleotide and a measure of the biophysical effect of the oligonucleotide determined based on real-world experimental determination;
training a machine-learned model in a first stage using the first training set, the machine-learned model configured to map an oligonucleotide sequence to a measure of the biophysical effect;
after training the machine-learned model in the first stage, generating a second set of oligonucleotides such that each n-gram of the first set of oligonucleotides is represented at least once by the second set of oligonucleotides, the second set of oligonucleotides selected based on an output of the machine-learned model such that the second set of oligonucleotides corresponds to a distributed range of measures of the biophysical effect, the second set of oligonucleotides including an approximately equal number of oligonucleotides that correspond to the biophysical effect and that do not correspond to the biophysical effect;
synthesizing a subset of the second set of oligonucleotides;

administering the synthesized subset of the second set of oligonucleotides to one or more cells;

measuring, for each oligonucleotide of the subset of the second set of oligonucleotides, the biophysical effect on the one or more cells;

creating a second training set based, at least in part, on the synthesized subset of the second set of oligonucleotides and the measures of the biophysical effect; and training the machine-learned model in a second stage using the second training set.

28. The method of claim 27, wherein the subset of the second set of oligonucleotides comprises synthesizing no more than 256 oligonucleotides.

29. A method for training a machine-learned model, comprising:

generating a first set of oligonucleotides by performing all possible single n-gram mutations of an initial oligonucleotide to obtain oligonucleotides mapped to a distributed range of measures of having a biophysical effect such that each n-gram of the initial oligonucleotide is represented at least once by the first set of oligonucleotides;

creating a first training set comprising, for each oligonucleotide of the first set of oligonucleotides, a sequence of the oligonucleotide and a measure of the biophysical effect of the oligonucleotide determined based on real-world experimental determination;

training a machine-learned model in a first stage using the first training set, the machine-learned model configured to map an oligonucleotide sequence to a measure of the biophysical effect;

after training the machine-learned model in the first stage, generating a second set of oligonucleotides such that each n-gram of the first set of oligonucleotides is represented at least once by the second set of oligonucleotides, the second set of oligonucleotides selected based on an output of the machine-learned model such that the second set of oligonucleotides corresponds to a distributed range of measures of the biophysical effect, the second set of oligonucleotides including an approximately equal number of oligonucleotides that correspond to the biophysical effect and that do not correspond to the biophysical effect;

creating a second training set comprising, for each oligonucleotide of the second set of oligonucleotides, a sequence of the oligonucleotide and a measure of the biophysical effect of the oligonucleotide determined based on real-world experimental determination;

training the machine-learned model in a second stage using the second training set; and synthesizing an oligonucleotide selected based on an output of the machine-learned model to produce an oligonucleotide-based medicine.

* * * * *

SEQUENCE LISTING

```
Sequence total quantity: 42
SEQ ID NO: 1              moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 1
aagtctgtta cccc                                                              14

SEQ ID NO: 2              moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 2
cagtagtctt tcag                                                              14

SEQ ID NO: 3              moltype = DNA  length = 16
FEATURE                   Location/Qualifiers
misc_feature              1..16
                          note = Synthetic Sequence
source                    1..16
                          mol_type = other DNA
                          organism = synthetic construct
SEQUENCE: 3
ggtattcagt gtgatg                                                            16

SEQ ID NO: 4              moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 4
gtagtctttc aggg                                                              14

SEQ ID NO: 5              moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 5
gtattgaggt ctca                                                              14

SEQ ID NO: 6              moltype = DNA  length = 14
FEATURE                   Location/Qualifiers
misc_feature              1..14
                          note = Synthetic Sequence
source                    1..14
                          mol_type = other DNA
                          organism = synthetic construct
SEQUENCE: 6
agtcttggcc ctct                                                              14

SEQ ID NO: 7              moltype = DNA  length = 13
FEATURE                   Location/Qualifiers
misc_feature              1..13
                          note = Synthetic Sequence
source                    1..13
                          mol_type = other DNA
                          organism = synthetic construct
SEQUENCE: 7
gcattggtat tca                                                               13

SEQ ID NO: 8              moltype = DNA  length = 14
FEATURE                   Location/Qualifiers
misc_feature              1..14
                          note = Synthetic Sequence
source                    1..14
                          mol_type = other DNA
                          organism = synthetic construct
```

```
SEQUENCE: 8
gtctctttac ctgg                                                              14

SEQ ID NO: 9            moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 9
taatgctcga tccc                                                              14

SEQ ID NO: 10           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 10
aagtctgttt cccc                                                              14

SEQ ID NO: 11           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 11
tcatggctgc agct                                                              14

SEQ ID NO: 12           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 12
tgcctctagg gatg                                                              14

SEQ ID NO: 13           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 13
agcagctgcc tcta                                                              14

SEQ ID NO: 14           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 14
gtgctccagt agtc                                                              14

SEQ ID NO: 15           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 15
tgctccagta gtct                                                              14

SEQ ID NO: 16           moltype = DNA   length = 14
FEATURE                 Location/Qualifiers
misc_feature            1..14
                        note = Synthetic Sequence
source                  1..14
                        mol_type = other DNA
```

```
                        organism = synthetic construct
SEQUENCE: 16
agtgcatcct tggc                                                              14

SEQ ID NO: 17           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 17
cctgctgggc cacc                                                              14

SEQ ID NO: 18           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 18
gctccagtag tctt                                                              14

SEQ ID NO: 19           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 19
actccaaatc ctgc                                                              14

SEQ ID NO: 20           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 20
tccaaggact ctca                                                              14

SEQ ID NO: 21           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 21
acctgggact cctg                                                              14

SEQ ID NO: 22           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 22
ggtttgcaat gctt                                                              14

SEQ ID NO: 23           moltype = DNA  length = 14
FEATURE                 Location/Qualifiers
misc_feature            1..14
                        note = Synthetic Sequence
source                  1..14
                        mol_type = other DNA
                        organism = synthetic construct
SEQUENCE: 23
tggccctgct gtgg                                                              14

SEQ ID NO: 24           moltype = DNA  length = 14
FEATURE                 Location/Qualifiers
misc_feature            1..14
                        note = Synthetic Sequence
source                  1..14
```

```
                        mol_type = other DNA
                        organism = synthetic construct
SEQUENCE: 24
ccgttggtgc cagt                                                              14

SEQ ID NO: 25           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 25
gtcttctccc gcca                                                              14

SEQ ID NO: 26           moltype = DNA   length = 14
FEATURE                 Location/Qualifiers
misc_feature            1..14
                        note = Synthetic Sequence
source                  1..14
                        mol_type = other DNA
                        organism = synthetic construct
SEQUENCE: 26
aggtgctttg gtct                                                              14

SEQ ID NO: 27           moltype = DNA   length = 16
FEATURE                 Location/Qualifiers
misc_feature            1..16
                        note = Synthetic Sequence
source                  1..16
                        mol_type = other DNA
                        organism = synthetic construct
SEQUENCE: 27
caaagtgata ccagtt                                                            16

SEQ ID NO: 28           moltype = DNA   length = 16
FEATURE                 Location/Qualifiers
misc_feature            1..16
                        note = Synthetic Sequence
source                  1..16
                        mol_type = other DNA
                        organism = synthetic construct
SEQUENCE: 28
gaatctcctt ttccag                                                            16

SEQ ID NO: 29           moltype = DNA   length = 16
FEATURE                 Location/Qualifiers
misc_feature            1..16
                        note = Synthetic Sequence
source                  1..16
                        mol_type = other DNA
                        organism = synthetic construct
SEQUENCE: 29
gaggatggca agcaca                                                            16

SEQ ID NO: 30           moltype = DNA   length = 16
FEATURE                 Location/Qualifiers
misc_feature            1..16
                        note = Synthetic Sequence
source                  1..16
                        mol_type = other DNA
                        organism = synthetic construct
SEQUENCE: 30
gtacctatag tctctg                                                            16

SEQ ID NO: 31           moltype = DNA   length = 16
FEATURE                 Location/Qualifiers
misc_feature            1..16
                        note = Synthetic Sequence
source                  1..16
                        mol_type = other DNA
                        organism = synthetic construct
SEQUENCE: 31
cttcttgatg tctttc                                                            16

SEQ ID NO: 32           moltype = DNA   length = 16
FEATURE                 Location/Qualifiers
misc_feature            1..16
                        note = Synthetic Sequence
```

```
source                        1..16
                              mol_type = other DNA
                              organism = synthetic construct
SEQUENCE: 32
cttttctatc agtctc                                                           16

SEQ ID NO: 33                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 33
ttttgtgtct tctgta                                                           16

SEQ ID NO: 34                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 34
accctcaagt ctcctg                                                           16

SEQ ID NO: 35                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 35
tctccttgct gtattt                                                           16

SEQ ID NO: 36                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 36
gtcagtatcc cagtgt                                                           16

SEQ ID NO: 37                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 37
gactctctga tgatac                                                           16

SEQ ID NO: 38                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 38
attctgtgtg cactgc                                                           16

SEQ ID NO: 39                 moltype = DNA   length = 16
FEATURE                       Location/Qualifiers
misc_feature                  1..16
                              note = Synthetic Sequence
source                        1..16
                              mol_type = other DNA
                              organism = synthetic construct
SEQUENCE: 39
ttgccaatat caccat                                                           16

SEQ ID NO: 40                 moltype = DNA   length = 16
FEATURE                       Location/Qualifiers
misc_feature                  1..16
```

```
                    note = Synthetic Sequence
source              1..16
                    mol_type = other DNA
                    organism = synthetic construct
SEQUENCE: 40
gtctgtgcat ctctcc                                                      16

SEQ ID NO: 41       moltype = DNA  length = 16
FEATURE             Location/Qualifiers
misc_feature        1..16
                    note = Synthetic Sequence
source              1..16
                    mol_type = other DNA
                    organism = synthetic construct
SEQUENCE: 41
tcttgtctga cattct                                                      16

SEQ ID NO: 42       moltype = DNA  length = 16
FEATURE             Location/Qualifiers
misc_feature        1..16
                    note = Synthetic Sequence
source              1..16
                    mol_type = other DNA
                    organism = synthetic construct
SEQUENCE: 42
tagtctctgt cagtta                                                      16
```